United States Patent
Page et al.

(10) Patent No.: US 11,491,105 B2
(45) Date of Patent: *Nov. 8, 2022

(54) METHODS OF TREATING MICROBIAL INFECTIONS, INCLUDING MASTITIS

(71) Applicants: Luoda Pharma Pty Ltd, Dublin (IE); Stephen Page, Newtown (AU); Sanjay Garg, Myrtle Bank (AU)

(72) Inventors: Stephen Page, Newtown (AU); Sanjay Garg, Myrtle Bank (AU)

(73) Assignee: LUODA PHARMA LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/766,233

(22) PCT Filed: Feb. 10, 2014

(86) PCT No.: PCT/AU2014/000102
§ 371 (c)(1),
(2) Date: Aug. 6, 2015

(87) PCT Pub. No.: WO2014/121343
PCT Pub. Date: Aug. 14, 2014

(65) Prior Publication Data
US 2015/0366797 A1    Dec. 24, 2015

(30) Foreign Application Priority Data

Feb. 8, 2013   (AU) ................................ 2013900411

(51) Int. Cl.
| | | |
|---|---|---|
| *A61K 9/00* | (2006.01) | |
| *A61K 31/35* | (2006.01) | |
| *A61K 31/352* | (2006.01) | |
| *A61K 45/06* | (2006.01) | |

(52) U.S. Cl.
CPC ............ *A61K 9/0041* (2013.01); *A61K 31/35* (2013.01); *A61K 31/352* (2013.01); *A61K 45/06* (2013.01)

(58) Field of Classification Search
CPC .............................. A61K 9/0041; A61K 31/35
See application file for complete search history.

(56) References Cited

U.S. PATENT DOCUMENTS

| | | | | |
|---|---|---|---|---|
| 3,920,847 A | * | 11/1975 | Chalaust | A61K 9/0014 514/512 |
| 2013/0189368 A1 | | 7/2013 | Mosqueira et al. | |
| 2015/0164926 A1 | * | 6/2015 | Froyman | A61K 31/665 514/23 |

FOREIGN PATENT DOCUMENTS

WO    WO-2011/150481 A1    12/2011

OTHER PUBLICATIONS

Liu, Polyether Antibiotics Naturally Occurring Acid Ionophores vol. 1: Biology, pp. 43-102, publ. 1982.*
Brindle, Encyclopedia of Chemical Technology. Polyether antibiotics, Nov. 2013, Wiley, Abstract and pp. 1-30.*
Huczynski et al., Journal of Molecular Structure, 2008, Elsevier, vol. 891, pp. 481-490.*
Chen et al., Journal of Medicinal Chemistry, 2001, American Chemical Society, vol. 44, pp. 2374-2377.*
Dykhuizen, Antonie van Leeuwenhoek, 1998, Kluwer Academic Publishers, vol. 73, pp. 25-33.*
Foroumadi et al., European Journal of Medicinal Chemistry, 2003, Elsevier, vol. 38, pp. 851-854.*
Duffield et al., A meta-analysis of the impact of monenism in lactating dairy cattle. Part 3. Health and reproduction. *J. Dairy Sci.* 91(6):2328-41 (2008).
Gilbert et al., The 10 x '20 Initiative: Pursuing a global commitment to develop 10 new antibacterial drugs by 2020. *Clin. Infect. Dis.* 50(8):1081-3 (2010).
Heuer et al., Effect of monensin on blood ketone bodies, incidence and recurrence of disease and fertility in dairy cows. *J. Dairy Sci.* 84(5): 1085-97 (2001).
International Search Report and Written Opinion of the International Searching Authority in connection with International Application No. PCT/AU2014/00102, United States Patent Office, dated Feb. 10, 2014.
Laven et al., Clinical forum: Choosing mastitis treatment in the lactating cow: selling or science? *UK Vet: Livestock*, 13(4):29-36 (2008).
McDougall et al., Clinical and bacteriological response to treatment of clinical mastitis with one of three intramammary antibiotics. *N. Z. Vet. J.* 55(4): 161-70 (2007).
McDougall et al., Parenteral treatment of clinical mastitis with tylosin base or penethamate hydriodide in dairy cattle. *J. Dairy Sci.* 90(2):779-89 (2007).
McDougall et al., Production and health of pasture-fed dairy cattle following oral treatment with the ionophore lasalocid. *J. Dairy Sci.* 87(9): 2967-76 (2004).
McDougall, Efficacy of two antibiotic treatments in curing clinical and subclinical mastitis in lactating dairy cows. *N. Z. Vet. J.* 46(6):226-32 (1998).
McDougall, Prevalence of clinical mastitis in 38 Waikato dairy herds in early lactation. *N. Z. Vet. J.* 47(4): 143-9 (1999).
Meaney et al., Dry period teat seal. *Vet. Rec.* 99(2):30 (1976).
Naujokat et al., Salinomycin as a drug for targeting human cancer stem cells. *J. Biomed. Biotechnol.* 2012:950658 (2012).

(Continued)

*Primary Examiner* — Shobha Kantamneni
(74) *Attorney, Agent, or Firm* — Marshall, Gerstein & Borun LLP

(57) ABSTRACT

The invention includes methods and compositions for treating mastitis in a subject. The method includes the step of administering, by intramammary delivery, a therapeutically effective amount of a polyether ionophore, or a therapeutically acceptable salt thereof, to the mammary gland of the subject.

15 Claims, 28 Drawing Sheets

(56) References Cited

OTHER PUBLICATIONS

Petrovski et al., The incidence and aetiology of clinical bovine mastitis on 14 farms in Northland, New Zealand. *N. Z. Vet. J.* 57(2):109-15 (2009).
Shum et al., Environmental mastitis in intensive high-producing dairy herds in New South Wales. *Aust. Vet. J.* 87(12): 469-75 (2009).
Smith et al., The persistence of penicillin G in the mammary gland when infused immediately after the last milking of lactation. *J. Dairy Res.* 34: 47-57 (1967).

\* cited by examiner

| Strain ID # | Source | Species | Resistance Profile |
|---|---|---|---|
| ATCC 49775 | Human | S. aureus | |
| MSS 1 | Cow | S. aureus | |
| MSS 2 | Cat | S. intermedius | P |
| MSS 3 | Cat | S. aureus | P |
| MSS 4 | Unknown | S. pseudintermedius | |
| MSS 5 | Dog | S. intermedius | P |
| MSS 6 | Human | S. pseudintermedius | |
| MSS 7 | Dog | S. pseudintermedius | P |
| MSS 8 | Dog | Coagulase negative | P, Te |
| MSS 9 | Dog | S. intermedius | |
| MSS 10 | Dog | S. intermedius | |
| MSS 11 | Unknown | Coagulase negative | P, Te |
| MSS 12 | Dog | S. pseudintermedius | P |
| MSS 13 | Bird | Coagulase negative | P, Te |
| MSS 14 | Dog | S. intermedius | P |
| MSS 15 | Dog | S. intermedius | P, Te |
| MSS 16 | Pig | Coagulase negative | P |
| MSS 17 | Pig | S. aureus | Cl, E |
| MSS 18 | Dog | S. intermedius | P |
| MSS 19 | Dog | Coagulase negative | E |
| MSS 20 | Dog | S. pseudintermedius | Cl, P, Te |
| MRSA 1 | Human | S. aureus | Enr, E, Gn, O, P |
| MRSA 2 | Human | S. aureus | Gn, O, P, Tm |
| MRSA 3 | Human | S. aureus | E, Enr, O, P |
| MRSA 4 | Human | S. aureus | E, Enr, O, P |
| MRSA 5 | Human | S. aureus | E, Enr, Gn, O, P, Te |
| MRSA 6 | Human | S. aureus | E, Enr, O, P, Tm |
| MRSA 7 | Human | S. aureus | E, Enr, Gn, O, P, Tm |
| MRSA 8 | Human | S. aureus | E, Gn, O, P, Te, Tm |
| MRSA 9 | Human | S. aureus | E, O, P |
| MRSA 10 | Human | S. aureus | E, Enr, O, P |
| MRSA 11 | Human | S. aureus | O, P |
| MRSA 12 | Human | S. aureus | E, O, P, Te |
| MRSA 13 | Human | S. aureus | E, O, P |
| MRSA 14 | Human | S. aureus | E, O, P |
| MRSA 15 | Human | S. aureus | E, O, P |
| MRSA 16 | Human | S. aureus | O, P, Te |

FIGURE 1

| Compound | Ampicillin | LP 1088 | LP 1369 | LP 4525 | LP 6315 | LP 9666 |
|---|---|---|---|---|---|---|
| $MIC_{50}$ | 0.5 | 1 | 1 | 0.5 | 2 | 8 |
| $MIC_{90}$ | 16 | 2 | 2 | 1 | 4 | 64 |
| MIC Range | 0.25 – 32 | 0.5 – 4 | 0.5 – 2 | 0.25 – 1 | 2 – 8 | 2 – >128 |

Figure 5

| Compound | Ampicillin | LP 1088 | LP 1369 | LP 4525 | LP 6315 | LP 9666 |
|---|---|---|---|---|---|---|
| $MIC_{50}$ | 128 | 1 | 1 | 0.5 | 4 | 32 |
| $MIC_{90}$ | >128 | 2 | 1 | 0.5 | 4 | 64 |
| MIC Range | 8 – >128 | 1 – 2 | 0.5 – 2 | 0.25 – 1 | 2 – 16 | 4 – 128 |

| Compound | LP 1088 | LP 1369 | LP 4525 | LP 6315 | LP 9666 |
|---|---|---|---|---|---|
| $MBC_{50}$ | >128 | 64 | >128 | >128 | >128 |
| $MBC_{90}$ | >128 | >128 | >128 | >128 | >128 |
| MBC Range | 4 – >128 | 4 – >128 | 64 – >128 | 64 – >128 | 128 – >128 |

| Compound | LP 1088 | LP 1369 | LP 4525 | LP 6315 | LP 9666 |
|---|---|---|---|---|---|
| $MBC_{50}$ | >128 | >128 | >128 | 128 | >128 |
| $MBC_{90}$ | >128 | >128 | >128 | >128 | >128 |
| MBC Range | 128 – >128 | 64 – >128 | 4 – >128 | 4 – >128 | 128 – >128 |

| | Growth Control | Ampicillin 1xMIC | Ampicillin 4xMIC | LP 1369 1xMIC | LP 1369 4xMIC | LP 1369 8xMIC |
|---|---|---|---|---|---|---|
| ATCC 49775 | 3.23 | -6.4 | -6.4 | -1.94 | -2.18 | -2.16 |
| MRSA 9 | 4.11 | -6.41 | N/A | -0.84 | -2.82 | -2.52 |

|  | Growth Control | Ampicillin 1xMIC | Ampicillin 4xMIC | LP 6315 1xMIC | LP 6315 4xMIC | LP 6315 8xMIC |
|---|---|---|---|---|---|---|
| ATCC 49775 | 3.23 | -6.4 | -6.4 | -1.49 | -2.47 | -2.42 |
| MRSA 9 | 4.11 | -6.41 | N/A | -0.64 | -3.13 | -2.86 |

| Adelaide # | GLY | SITE OF ISOLATION | Species | BREED | MRSP / MSSP | mec gene Pert | mecA by RT-PCR Adl | Cefoxitin ZD (mm) | Cefoxitin ZD, Adl (mm) | oxacillin ZD (mm) | oxacillin ZD,Adl (mm) | oxacillin Etest MIC (mg/L) |
|---|---|---|---|---|---|---|---|---|---|---|---|---|
| S1P1 | 191 | AXILLA | S. pseudintermedius | | MRSP | POS | POS | 0 | 0 | 0 | 0 | >256 |
| S2P2 | 193 | TISSUE | S. pseudintermedius | Shar pei X | MRSP | POS | POS | 21 | 21 | 0 | 0 | >256 |
| S3P3 | 194 | SKIN SWAB | S. pseudintermedius | Mastiff X | MRSP | POS | POS | 21 | 24 | 0 | 0 | >256 |
| S4P4 | 214 | SKIN SWAB | S. pseudintermedius | CKCS | MRSP | POS | POS | 29 | 20 | 0 | 0 | 2 |
| S5P5 | 215 | SKIN SWAB | S. pseudintermedius | Shar pei | MRSP | POS | POS | 26 | 30 | 0 | 0 | 4 |
| S6P6 | 218 | PAW SWAB | S. pseudintermedius | Dachshund | MRSP | POS | POS | 22 | 26 | 0 | 0 | >256 |
| S7P7 | 219 | SKIN SWAB | S. pseudintermedius | British Bulldog | MRSP | POS | POS | 21 | 19 | 0 | 0 | >256 |
| S8P8 | 220 | SKIN SWAB | S. pseudintermedius | British Bulldog | MRSP | POS | POS | 21 | 22 | 0 | 0 | >256 |
| S9P9 | 96 | SKIN SWAB | S. pseudintermedius | Akita | MRSP | POS | POS | 23 | 26 | 0 | 0 | 4 |
| S10P10 | 190 | SKIN SWAB | S. pseudintermedius | Akita | MRSP | POS | POS | 21 | 25 | 0 | 0 | >256 |
| S11P11 | 187 | TISSUE | S. pseudintermedius | Bull terrier | MSSP | POS | POS | 22 | 21 | 0 | 0 | >256 |
| S12P12 | 188 | SKIN SWAB | S. pseudintermedius | Great Dane | MRSP | POS | POS | 24 | 24 | 13 | 16 | 1.5 |
| S13P13 | 189 | R EAR SWAB | S. pseudintermedius | CKCS | MSSP | NEG | NEG | 36 | 40 | 26 | 36 | 0.125 |
| S14P14 | 185 | TISSUE | S. pseudintermedius | Labrador Retriever | MSSP | NEG | NEG | 34 | 32 | 22 | 29 | 0.25 |
| S15P15 | 191 | TISSUE | S. pseudintermedius | Maltese X | MSSP | NEG | NEG | 33 | 34 | 22 | 25 | 0.25 |
| S16P16 | 194 | SKIN SWAB | S. pseudintermedius | Maltese | MSSP | NEG | NEG | 38 | 42 | 26 | 34 | 0.19 |
| S17P17 | 195 | SKIN SWAB | S. pseudintermedius | Shar pei X | MSSP | NEG | NEG | 36 | 38 | 22 | 26 | 0.25 |
| S18P18 | 196 | TISSUE | S. pseudintermedius | JRT | MSSP | NEG | NEG | 25 | 40 | 22 | 30 | 0.25 |
| S19P19 | 197 | SKIN SWAB | S. pseudintermedius | Labrador Retriever | MSSP | NEG | NEG | 36 | 38 | 25 | 32 | 0.25 |
| S20P20 | 198 | SKIN SWAB | S. pseudintermedius | Fox Terrier | MSSP | NEG | NEG | 38 | 36 | 23 | 30 | 0.25 |
| S21P21 | 199 | R EAR SWAB | S. pseudintermedius | Labrador Retriever | MSSP | NEG | NEG | 36 | 40 | 27 | 37 | 0.125 |
| S22P22 | 200 | SKIN SWAB | S. pseudintermedius | Maltese | MSSP | NEG | NEG | 34 | 35 | 21 | 26 | 0.25 |
| S23P23 | 203 | | | | | | POS | 29 | 26 | 13 | 14 | 1.5 |

Figure 21

| | mecA by RT-PCR | Penicillin | Ampicillin | Amoxicillin | Erythromycin | Gentamycin | Clindamycin | Ciprofloxacin |
|---|---|---|---|---|---|---|---|---|
| S1P1 | POS | R | R | R | R | R | S | R |
| S2P2 | POS | R | R | R | R | R | I | R |
| S3P3 | POS | R | R | R | R | R | R | R |
| S4P4 | POS | R | R | R | R | R | R | R |
| S5P5 | POS | R | R | R | R | R | R | R |
| S6P6 | POS | R | R | R | R | R | R | R |
| S7P7 | POS | R | R | R | R | R | R | R |
| S8P8 | POS | R | R | S | R | R | R | R |
| S9P9 | POS | R | R | R | R | R | R | R |
| S10P10 | POS | R | R | R | R | R | I | S |
| S11P11 | POS | R | R | S | S | S | S | R |
| S12P12 | POS | R | R | S | S | R | S | S |
| S13P13 | NEG | R | R | S | S | S | S | S |
| S14P14 | NEG | R | R | S | S | S | S | S |
| S15P15 | NEG | R | R | S | S | S | S | S |
| S16P16 | NEG | R | R | S | S | S | S | S |
| S17P17 | NEG | R | R | S | S | S | S | S |
| S18P18 | NEG | R | R | S | S | S | S | S |
| S19P19 | NEG | R | R | S | S | S | S | S |
| S20P20 | NEG | R | R | S | S | S | S | S |
| S21P21 | NEG | S | S | S | S | S | S | S |
| S22P22 | NEG | R | R | S | S | S | S | S |
| S23P23 | POS | R | R | S | R | S | I | S |

Figure 22

| | mecA by RT-PCR | Cephalothin | Chloramphenicol | Tetracycline | Oxytetracycline | Vancomycin | Cefotetan | Maxifloxacin | Rifampin |
|---|---|---|---|---|---|---|---|---|---|
| S1P1 | POS | R | S | R | R | R | S | S | S |
| S2P2 | POS | S | R | S | S | R | S | I | S |
| S3P3 | POS | S | R | I | R | S | R | S | S |
| S4P4 | POS | I | R | R | R | S | S | S | S |
| S5P5 | POS | S | R | R | R | S | S | S | S |
| S6P6 | POS | S | R | I | R | R | S | S | S |
| S7P7 | POS | R | R | R | R | S | S | S | S |
| S8P8 | POS | I | R | I | I | S | S | S | S |
| S9P9 | POS | S | R | R | R | S | S | S | S |
| S10P10 | POS | S | S | S | S | S | S | S | S |
| S11P11 | POS | S | S | R | R | S | S | S | S |
| S12P12 | POS | S | S | S | S | S | S | S | S |
| S13P13 | NEG | S | S | S | I | S | S | S | S |
| S14P14 | NEG | S | S | S | S | S | S | S | S |
| S15P15 | NEG | S | S | S | S | S | S | S | S |
| S16P16 | NEG | S | S | S | I | S | S | S | S |
| S17P17 | NEG | S | S | S | S | S | S | S | S |
| S18P18 | NEG | S | S | S | S | S | S | S | S |
| S19P19 | NEG | S | S | R | I | S | S | S | S |
| S20P20 | NEG | S | S | S | S | S | S | S | S |
| S21P21 | NEG | S | S | S | S | S | S | S | S |
| S22P22 | NEG | S | S | S | S | S | S | S | S |
| S23P23 | POS | S | S | S | S | S | S | S | S |

Figure 22 cont.

|  | Column1 | AMP | LP 1369 | LP 4525 | LP6315 |
|---|---|---|---|---|---|
| 1 | S1P1 | 128 | 1 | 0.5 | 2 |
| 2 | S2P2 | 128 | 0.5 | 0.25 | 1 |
| 3 | S3P3 | 128 | 0.5 | 0.5 | 2 |
| 4 | S4P4 | 128 | 0.5 | 0.25 | 1 |
| 5 | S5P5 | 16 | 0.5 | 0.1 | 1 |
| 6 | S6P6 | 64 | 0.5 | 0.25 | 1 |
| 7 | S7P7 | 128 | 0.5 | 0.25 | 1 |
| 8 | S8P8 | 128 | 0.5 | 0.25 | 1 |
| 9 | S9P9 | 32 | 0.5 | 0.25 | 1 |
| 10 | S10P10 | 64 | 1 | 0.25 | 1 |
| 11 | S11P11 | 128 | 0.5 | 0.25 | 1 |
| 12 | S12P12 | 32 | 0.5 | 0.25 | 1 |
| 13 | S13P13 | 0.25 | 0.5 | 0.1 | 1 |
| 14 | S14P14 | 1 | 1 | 0.25 | 2 |
| 15 | S15P15 | 4 | 0.5 | 0.25 | 1 |
| 16 | S16P16 | 0.25 | 0.5 | 0.25 | 1 |
| 17 | S17P17 | 1 | 0.25 | 0.1 | 1 |
| 18 | S18P18 | 4 | 0.25 | 0.25 | 1 |
| 19 | S19P19 | 0.5 | 0.5 | 0.25 | 1 |
| 20 | S20P20 | 4 | 0.5 | 0.25 | 1 |
| 21 | S21P21 | 0.1 | 0.5 | 0.25 | 2 |
| 22 | S22P22 | 8 | 0.5 | 0.25 | 2 |
| 23 | S23P23 | 32 | 0.5 | 0.25 | 1 |

| Column1 | AMP | LP 1369 | LP 4525 | LP6315 |
|---|---|---|---|---|
| MIC50 (µg/ml) | 32 | 0.5 | 0.25 | 1 |
| MIC90 (µg/ml) | 128 | 1 | 0.25 | 2 |
| MIC mode (µg/ml) | 128 | 0.5 | 0.25 | 1 |
| MIC range (µg/ml) | 0.1-128 | 0.25-1 | 0.1-0.25 | 1-2 |

Figure 23

| | MIC | | | MBC | | |
|---|---|---|---|---|---|---|
| Compound | MIC$_{50}$ | MIC$_{90}$ | MIC Range | MBC$_{50}$ | MBC$_{90}$ | MBC Range |
| LP1088 | 1 | 2 | 0.25-4 | 128 | x | 4-x |
| LP1369 | 2 | 4 | 0.5-8 | 64 | x | 2-x |
| LP4525 | 0.25 | 1 | 0.25-2 | 128 | x | 2-x |
| LP6315 | 0.5 | 4 | 0.25-8 | 128 | x | 4-x |
| LP9666 | 32 | 128 | 1-x | x | x | 64-x |
| Ampicillin | 0.25 | 0.25 | 0.25-0.5 | N/A | N/A | N/A |

Note: 'x' indicates confluent growth

| | MIC | | | MBC | | |
|---|---|---|---|---|---|---|
| Compound | MIC$_{50}$ | MIC$_{90}$ | MIC Range | MBC$_{50}$ | MBC$_{90}$ | MBC Range |
| LP1088 | 1 | 2 | 1-4 | x | x | 4-x |
| LP1369 | 1 | 4 | 0.5-8 | x | x | 2-x |
| LP4525 | 0.5 | 1 | 0.25-1 | 64 | x | 2-x |
| LP6315 | 4 | 4 | 1-4 | 128 | x | 4-x |
| LP9666 | 32 | 128 | 8-128 | x | x | 64-x |
| Ampicillin | 0.25 | 0.5 | 0.25-0.5 | N/A | N/A | N/A |

Note: 'x' indicates confluent growth

|  | MIC | | | MBC |
|---|---|---|---|---|
| Compound | $MIC_{50}$ | $MIC_{90}$ | MIC Range | Range |
| LP1088 | 2 | 4 | 0.5-4 | 4-x |
| LP1369 | 2 | 8 | 0.5-8 | 32-x |
| LP4525 | 0.5 | 1 | 0.25-1 | 8-x |
| LP6315 | 2 | 8 | 0.25-8 | 32-x |
| LP9666 | 64 | 128 | 4-128 | x |
| Ampicillin | 0.25 | 0.25 | - | N/A |

Note: 'x' indicates confluent growth

Figure 27

|  | MIC | | | MBC | | |
|---|---|---|---|---|---|---|
| Compound | $MIC_{50}$ | $MIC_{90}$ | MIC Range | $MBC_{50}$ | $MBC_{90}$ | MBC Range |
| LP1088 | 0.5 | 1 | 0.25-2 | x | x | 64-x |
| LP1369 | 2 | 4 | 2-4 | x | x | 64-x |
| LP4525 | 0.25 | 0.25 | 0.25-2 | 64 | 128 | 16-x |
| LP6315 | 0.25 | 0.5 | 0.25-0.5 | 128 | 128 | 8-x |
| LP9666 | 32 | 64 | 4-128 | x | x | x |
| Ampicillin | 0.25 | 0.25 | - | N/A | N/A | N/A |

Note: 'x' indicates confluent growth

Figure 28

|  | MIC | | | MBC |
|---|---|---|---|---|
| Compound | $MIC_{50}$ | $MIC_{90}$ | MIC Range | Range |
| LP1088 | 1 | 1 | 0.25-1 | 8-x |
| LP1369 | 2 | 4 | 0.5-4 | 32-128 |
| LP4525 | 0.25 | 0.25 | - | 4-x |
| LP6315 | 0.25 | 0.25 | - | 4-128 |
| LP9666 | 4 | 32 | 1-32 | x |
| Ampicillin | 0.5 | 0.5 | 0.25-0.5 | N/A |

Note: 'x' indicates confluent growth

Figure 29

| Farm | Cow | Quarter | Gram stain | Catalase test | Coagulase | Esculin | CAMP | Level of Haemolysis | Lancefield Group |
|---|---|---|---|---|---|---|---|---|---|
| MAM | 865 | LR | Positive | Positive | Positive | | | γ-haemolytic | - |
| MAM | 940 | RR | Positive | Negative | | Negative | Negative | γ-haemolytic | Ungroupable |
| MAM | 954 | RR2 | Positive | Positive | Negative | | | γ-haemolytic | - |
| MAM | 954 | RR1 | Positive | Positive | Positive | | | β-haemolytic | - |
| BEV | 978 | RR1 | Positive | Positive | Negative | | | α-haemolytic | - |
| MAM | 1041 | RF1 | Positive | Positive | Positive | | | β-haemolytic | - |
| MAM | 1041 | RF2 | Positive | Positive | Positive | | | β-haemolytic | - |
| MAM | 1051 | RF1 | Positive | Positive | Positive | | | γ-haemolytic | - |
| MAM | 1060 | LR | Positive | Positive | Negative | | | γ-haemolytic | - |
| MAM | 1092 | LR | Positive | Positive | Positive | | | β-haemolytic | - |
| MAM | 1096 | RF | Positive | Positive | Positive | | | β-haemolytic | - |
| MAM | 1155 | LR | Positive | Positive | Positive | | | γ-haemolytic | - |
| MAM | 1155 | LF | Positive | Positive | Positive | | | γ-haemolytic | - |
| MAM | 1194 | LF | Positive | Positive | Negative | | | γ-haemolytic | - |
| MAM | 1196 | LF | Positive | Positive | Positive | | | β-haemolytic | - |
| MAM | 1222 | RF | Positive | Positive | Negative | Negative | | γ-haemolytic | - |
| MAM | 1232 | LF | Positive | Positive | Positive | | | | - |
| MAM | 1232 | LR | Positive | Positive | Positive | | | | - |
| MAM | 1251 | RF | Positive | Positive | Positive | | | β-haemolytic | - |
| MAM | 1271 | RF1 | Negative | Negative | | | Negative | α-haemolytic | - |
| MAM | 1271 | RF | Positive | Positive | Negative | | | γ-haemolytic | - |
| MAM | 1271 | RF2 | Positive | Positive | Negative | | | γ-haemolytic | - |
| MAM | 1283 | LF2 | Positive | Negative | | Positive | Negative | α-haemolytic | Ungroupable |
| MAM | 1283 | LF1 | Positive | Positive | | | | γ-haemolytic | - |
| BEV | 1304 | RR | Positive | Positive | | | | α-haemolytic | - |
| BEV | 1337 | FR2 | Positive | Negative | | Negative | Negative | β-haemolytic | B |
| BEV | 1337 | FL | Positive | Negative | | Negative | Negative | β-haemolytic | B |

Figure 30

| | | | | | | | | | |
|---|---|---|---|---|---|---|---|---|---|
| BEV | 1337 | FR1 | Positive | Negative | - | Positive | Negative | α-haemolytic | Ungroupable |
| BEV | 1346 | FR | Positive | Negative | - | Negative | Negative | β-haemolytic | B |
| BEV | 1346 | RR1 | Positive | Negative | - | Negative | Negative | β-haemolytic | B |
| BEV | 1346 | RR | Positive | Negative | - | Negative | Negative | | B |
| BEV | 1346 | FL | Positive | Negative | - | Negative | Negative | β-haemolytic | B |
| BEV | 1346 | RL | Positive | Negative | - | Negative | Negative | β-haemolytic | B |
| BEV | 1537 | FL | Positive | Positive | Positive | - | - | γ-haemolytic | - |
| BEV | 1591 | RF1 | Positive | Negative | - | Negative | - | α-haemolytic | Ungroupable |
| BEV | 1765 | RR | Positive | Positive | Negative | - | - | α-haemolytic | - |
| BEV | 1765 | RR1 | Positive | Negative | - | Negative | Negative | β-haemolytic | B |
| BEV | 2448 | RL | Negative | Positive | - | - | - | - | - |
| BEV | 2530 | FLW | Positive | Positive | Negative | - | - | γ-haemolytic | - |
| BEV | 2825 | FR | Negative | Positive | - | - | - | - | - |
| BEV | 2825 | RR | Negative | Positive | Negative | - | - | γ-haemolytic | - |
| BEV | 3071 | RL2 | Positive | Negative | - | Negative | Negative | β-haemolytic | B |
| BEV | 3078 | RRL2 | Positive | Negative | - | Negative | Negative | β-haemolytic | B |
| BEV | 3179 | RL | Positive | Negative | - | Negative | Negative | β-haemolytic | B |
| BEV | 3956 | RL | Positive | Negative | - | - | Negative | β-haemolytic | B |
| BEV | 4027 | RR | Positive | Positive | Negative | - | - | γ-haemolytic | - |
| BEV | 6019 | FR1 | Positive | Negative | - | Negative | Negative | α-haemolytic | Ungroupable |
| BEV | 6121 | FL | Positive | Positive | Negative | - | - | γ-haemolytic | - |
| BEV | 6154 | RL | Positive | Negative | - | Negative | Negative | α-haemolytic | Ungroupable |
| BEV | 6175 | FL | Positive | Negative | - | Positive | Negative | α-haemolytic | Ungroupable |
| CTRL | 6533 | Control strain | Positive | Positive | Positive | - | - | - | - |

Figure 30 cont.

| Farm | Cow | Quarter | Cellular morphology | Additional morphology comments | Size of singe cells | Diagnosis |
|---|---|---|---|---|---|---|
| MAM | 865 | LR | Cocci | Very round | Medium | S. aureus |
| MAM | 940 | RR | Cocci | Lancet shaped | Small | S. uberis |
| MAM | 954 | RR2 | Cocci | Round, clustered | Medium | Coagulase negative Staph |
| MAM | 954 | RR1 | Cocci | Round, clustered | Medium | S. aureus |
| BEV | 978 | RR1 | Rod | Chains | Large | Bacillus spp. |
| MAM | 1041 | RF1 | Cocci | Clustered | Medium | S. aureus |
| MAM | 1041 | RF2 | Cocci | Round | Medium | S. aureus |
| MAM | 1051 | RF1 | Cocci | Round | Medium | S. aureus |
| MAM | 1060 | LR | Cocci | Round, clustered | Medium | Coagulase negative Staph |
| MAM | 1092 | LR | Cocci |  | Small | S. aureus |
| MAM | 1096 | RF | Cocci | Small noticable filaments protruding from each cluster | Medium | S. aureus |
| MAM | 1155 | LR | Cocci | Very round | Medium | S. aureus |
| MAM | 1155 | LF | Cocci | Grape-like | Medium | S. aureus |
| MAM | 1194 | LF | Cocci | Small, round | Medium | Coagulase negative Staph |
| MAM | 1196 | LF | Cocci | Grape-like | Small | S. aureus |
| MAM | 1222 | RF | Cocci |  | Small | Coagulase negative Staph |
| MAM | 1232 | LF | Cocci |  | Small | S. aureus |
| MAM | 1232 | LR | Cocci | Round, clustered | Medium | S. aureus |
| MAM | 1251 | RF | Cocci | Lancet shaped | Medium | S. aureus |
| MAM | 1271 | RF1 | Cocci | Round, grape-like | Small | Unidentified Gm negative |
| MAM | 1271 | RF | Cocci | Small, round | Small | Coagulase negative Staph |
| MAM | 1271 | RF2 | Cocci | Highly clustered cocci | Small | Coagulase negative Staph |
| MAM | 1283 | LF2 | Cocci | Very small | Small | S. uberis |
| MAM | 1283 | LF1 | Cocci | Grape-like, clustered | Medium | S. aureus |
| BEV | 1304 | RR | Rod | Very small, oval/rod shaped, arranged in a palisade. | Small | S. aureus |

Figure 30 cont.

| | | | | | |
|---|---|---|---|---|---|
| BEV | 1337 | FR2 | Cocci | Very round | Medium | S. agalactiae |
| BEV | 1337 | FL | Cocci | | Small | S. agalactiae |
| BEV | 1337 | FR1 | Cocci | Round | Medium | S. uberis |
| BEV | 1346 | FR | Cocci | Lancet shaped | Small | S. agalactiae |
| BEV | 1346 | RR1 | Cocci | Lancet shaped | Medium | S. agalactiae |
| BEV | 1346 | RR | Cocci | Lancet shaped | Small | S. agalactiae |
| BEV | 1346 | FL | Cocci | Lancet shaped | Small | S. agalactiae |
| BEV | 1346 | RL | Cocci | Round | Small | S. agalactiae |
| BEV | 1537 | FL | Flat diplococci | Lancet shaped, very clustered | Medium | S. aureus |
| BEV | 1591 | RF1 | Cocci | Lancet shaped | Small | S. uberis |
| BEV | 1765 | RR | Cocci | Small, round | Small | Coagulase negative Staph |
| BEV | 1765 | RR1 | Cocci | | | S. agalactiae |
| BEV | 2448 | RL | Rod | Short, fat rod | Small | Unidentified Gm negative |
| BEV | 2530 | FLW | Cocci | | | Coagulase negative Staph |
| BEV | 2825 | FR | Cocci | Lancet shaped | Small | Unidentified Gm negative |
| BEV | 2825 | RR | Cocci | Lancet shaped | Small | Unidentified Gm negative |
| BEV | 3071 | RL2 | Cocci | | | S. agalactiae |
| BEV | 3078 | RRL2 | Cocci | Lancet shaped | Medium | S. agalactiae |
| BEV | 3179 | RL | Cocci | | Small | S. agalactiae |
| BEV | 3956 | RL | Cocci | Lancet shaped | Small | S. agalactiae |
| BEV | 4027 | RR | Hyphae and buds | Coccus irregular shape | | Unidentified yeast |
| BEV | 6019 | FR1 | Cocci | Lancet shaped | Medium | S. uberis |
| BEV | 6121 | FL | Cocci | | | Coagulase negative Staph |
| BEV | 6154 | RL | Cocci | Lancet shaped | Small | S. uberis |
| BEV | 6175 | FL | Cocci | Very small, round | Small | S. uberis |
| CTRL | 6533 | Control strain | Cocci | Round, grape-like | Large | S. aureus |

Figure 30 cont.

| MIC | | Compound | | | | | |
|---|---|---|---|---|---|---|---|
| Cow | Quarter | Amp | LP1088 | LP1369 | LP4525 | LP6315 | LP9666 |
| 865 | LR | | | | | | |
| 940 | RR | | | | | | |
| 954 | RR1 | 0.25 | 2 | 1 | 0.5 | 2 | 64 |
| 954 | RR2 | 0.25 | 2 | 1 | 0.5 | 4 | x |
| 978 | RR1 | | | | | | |
| 1041 | RF1 | 0.5 | 2 | 1 | 0.5 | 4 | 128 |
| 1041 | RF2 | 0.25 | 1 | 0.5 | 0.25 | 2 | 32 |
| 1051 | RF1 | 0.25 | 2 | 1 | 0.5 | 4 | 16 |
| 1060 | LR | | | | | | |
| 1092 | LR | 0.25 | 1 | 0.5 | 0.5 | 4 | 16 |
| 1096 | RF | 0.25 | 1 | 0.5 | 0.25 | 4 | 16 |
| 1155 | LF | 0.25 | 1 | 0.5 | 0.25 | 4 | 64 |
| 1155 | LR | 0.25 | 4 | 4 | 1 | 1 | 32 |
| 1194 | LF | 0.25 | 4 | 8 | 1 | 2 | x |
| 1196 | LF | 0.25 | 1 | 1 | 0.25 | 4 | 64 |
| 1222 | RF | 0.25 | 0.5 | 2 | 0.25 | 0.25 | 16 |
| 1232 | LF | 0.5 | 1 | 1 | 0.5 | 2 | 128 |
| 1232 | LR | 0.25 | 1 | 0.5 | 0.25 | 2 | 8 |
| 1251 | RF | 0.25 | 1 | 1 | 0.5 | 2 | 64 |
| 1271 | RF1 | | 0.5 | 1 | 0.25 | 0.25 | 8 |
| 1271 | RF | | | | | | |
| 1271 | RF2 | | | | | | |
| 1283 | LF2 | 0.5 | 1 | 1 | 0.25 | 0.25 | 1 |
| 1283 | LF1 | | 0.25 | 0.5 | 0.25 | 0.25 | 2 |
| 1337 | FR1 | | 0.25 | 0.5 | 0.25 | 0.25 | 16 |
| 1337 | FR2 | 0.25 | 2 | 2 | 0.25 | 0.25 | 4 |
| 1337 | FL | | 1 | 4 | 0.25 | 0.5 | 32 |
| 1346 | FR | | 0.5 | 4 | 0.25 | 0.25 | 128 |
| 1346 | RR1 | | 0.5 | 2 | 0.25 | 0.25 | 16 |
| 1346 | RR | | 0.25 | 2 | 2 | 0.25 | 4 |
| 1346 | FL | | 1 | 2 | 0.25 | 0.25 | 16 |
| 1346 | RL | | 0.5 | 2 | 0.25 | 0.25 | 32 |
| 1537 | FL | 0.5 | 2 | 4 | 0.5 | 0.25 | 16 |
| 1591 | RF1 | | | | | | |
| 1765 | RR | 0.25 | 2 | 4 | 0.25 | 0.25 | 4 |
| 1765 | RR1 | | 1 | 4 | 0.25 | 0.5 | 64 |
| 2530 | FLW | 4 | x | x | x | x | x |
| 3071 | RL2 | | 0.5 | 2 | 0.25 | 0.25 | 16 |
| 3078 | RRL2 | | 0.5 | 2 | 0.25 | 0.5 | 32 |
| 3179 | RL | | 1 | 2 | 0.25 | 0.25 | 32 |
| 3956 | RL | | 0.5 | 2 | 0.25 | 0.25 | 8 |
| 4027 | RR | x | x | x | x | x | x |
| 6019 | FR1 | | 0.25 | 1 | 0.25 | 0.25 | 2 |
| 6121 | FL | 0.25 | 2 | 0.5 | 0.25 | 1 | 128 |
| 6154 | RL | | 0.5 | 2 | 0.25 | 0.25 | 32 |
| 6175 | FL | 0.5 | 1 | 2 | 0.25 | 0.25 | 2 |
| 1304 | RR | | | | | | |
| 1591 | RR | | | | | | |
| 6533 | S. aureus control strain | 0.25 | 1 | 1 | 0.25 | 2 | 8 |

Note: 'x' indicates confluent growth.

Figure 31

| MBC | | Compound | | | | |
|---|---|---|---|---|---|---|
| Cow | Quarter | LP1088 | LP1369 | LP4525 | LP6315 | LP9666 |
| 865 | LR | | | | | |
| 940 | RR | | | | | |
| 954 | RR1 | 128 | x | x | 128 | x |
| 954 | RR2 | x | x | 128 | x | x |
| 978 | RR1 | 64 | 16 | 32 | 128 | 128 |
| 1041 | RF1 | 128 | x | 64 | 128 | x |
| 1041 | RF2 | 8 | x | 8 | 64 | 64 |
| 1051 | RF1 | x | x | x | x | x |
| 1060 | LR | 4 | x | 128 | 32 | x |
| 1092 | LR | x | x | 128 | x | x |
| 1096 | RF | x | x | 128 | 128 | x |
| 1155 | LF | 128 | 128 | 128 | 128 | x |
| 1155 | LR | x | 64 | 128 | 64 | x |
| 1194 | LF | x | x | 64 | x | x |
| 1196 | LF | x | x | 32 | x | x |
| 1222 | RF | 128 | 32 | 32 | 32 | x |
| 1232 | LF | 64 | 128 | 16 | 32 | x |
| 1232 | LR | 128 | x | 64 | 64 | x |
| 1251 | RF | 4 | 2 | 2 | 4 | x |
| 1271 | RF1 | 64 | 64 | 32 | 8 | x |
| 1271 | RF | 128 | x | 32 | 128 | x |
| 1271 | RF2 | | | | | |
| 1283 | LF2 | 32 | 64 | 8 | 16 | x |
| 1283 | LF1 | 128 | 64 | 64 | 64 | x |
| 1337 | FR1 | x | 128 | x | 64 | x |
| 1337 | FR2 | 64 | 64 | 16 | 16 | x |
| 1337 | FL | x | 128 | 128 | 128 | x |
| 1346 | FR | x | 128 | 64 | 128 | x |
| 1346 | RR1 | 128 | 128 | 64 | 128 | x |
| 1346 | RR | 64 | 64 | 16 | 32 | x |
| 1346 | FL | x | 128 | 128 | 128 | x |
| 1346 | RL | x | 128 | 64 | 128 | x |
| 1537 | FL | 64 | 32 | 32 | 16 | x |
| 1591 | RF1 | | | | | |
| 1765 | RR | 16 | 64 | 8 | 32 | x |
| 1765 | RR1 | 64 | 64 | 32 | 8 | x |
| 2530 | FLW | 128 | x | x | x | x |
| 3071 | RL2 | x | 128 | 128 | 64 | x |
| 3078 | RRL2 | x | 128 | 64 | 128 | x |
| 3179 | RL | x | 128 | 128 | x | x |
| 3956 | RL | x | 128 | 64 | 64 | x |
| 4027 | RR | | x | x | x | x |
| 6019 | FR1 | 128 | 64 | 32 | 32 | x |
| 6121 | FL | 128 | 32 | 64 | 128 | x |
| 6154 | RL | x | 128 | 64 | 128 | x |
| 6175 | FL | 16 | 32 | 4 | 4 | x |
| 1304 | RR | | | | | |
| 1591 | RR | | | | | |
| 6533 | S. aureus control strain | | | | | |

Figure 32

| Cow | Quarter | Group | Pre-infection culture results(CFU/ml) | Post-Infection culture results(CFU/ml) | Post-Treatment culture results(CFU/ml) | Interpretation |
|---|---|---|---|---|---|---|
| 101 | Front right | IVP1 | 0 | | 0 | Control |
| 101 | Front left | IVP1 | 0 | S. uberis (>1x10$^5$) | S. uberis(6x10$^4$) | Cure (partial) |
| 101 | Rear right | IVP1 | 0 | S. uberis (>1x10$^5$) | S. uberis(4.6x10$^3$) | Cure (partial) |
| 101 | Rear left | IVP1 | 0 | | 0 | Control |
| 109 | Front right | IVP1 | 0 | S. uberis (4x10$^4$) | contaminated | Cure |
| 109 | Front left | IVP1 | 0 | | Coryne spp. (3x10$^3$) | Control |
| 109 | Rear right | IVP1 | 0 | | contaminated | Control |
| 109 | Rear left | IVP1 | 0 | | S. uberis (>1x10$^5$) | Failure |
| 114 | Front right | IVP1 | 0 | | 0 | Control |
| 114 | Front left | IVP1 | 0 | S. uberis (>1x10$^5$) | S. uberis (>1x10$^5$) | Failure |
| 114 | Rear right | IVP1 | 0 | S. uberis (>1x10$^5$) | S. uberis (4x10$^4$) | Cure (partial) |
| 114 | Rear left | IVP1 | 0 | | 0 | Control |
| 107 | Front right | IVP2 | 0 | | 0 | Control |
| 107 | Front left | IVP2 | S. uberis (30x10$^4$) | S. uberis(1x10$^2$) | 0 | Cure |
| 107 | Rear right | IVP2 | 0 | S. uberis (>1x10$^5$) | 0 | Cure |
| 107 | Rear left | IVP2 | 0 | | 0 | Control |

FIGURE 36

| 108 | Front right | IVP2 | 0 | | contaminated | Control |
| 108 | Front left | IVP2 | 0 | S. uberis($2.6 \times 10^3$) | contaminated | Cure |
| 108 | Rear right | IVP2 | 0 | S. uberis($3.4 \times 10^3$) | CNS ($4.8 \times 10^3$) | Cure |
| 108 | Rear left | IVP2 | 0 | | contaminated | Control |
| 113 | Front right | IVP2 | 0 | S. uberis ($>1 \times 10^5$) | No clinical resoln. | No clinical resoln. |
| 113 | Front left | IVP2 | 0 | | No clinical resoln. | No clinical resoln. |
| 113 | Rear right | IVP2 | 0 | | No clinical resoln. | No clinical resoln. |
| 113 | Rear left | IVP2 | 0 | S. uberis ($>1 \times 10^5$) | No clinical resoln. | No clinical resoln. |
| 102 | Front right | Ref | 0 | | Coryne spp. ($2 \times 10^3$) | Control |
| 102 | Front left | Ref | 0 | S. uberis ($>1 \times 10^5$) | 0 | Cure |
| 102 | Rear right | Ref | 0 | S. uberis ($>1 \times 10^5$) | 0 | Cure |
| 102 | Rear left | Ref | 0 | | 0 | Control |
| 103 | Front right | Ref | 0 | S. uberis ($>1 \times 10^5$) | 0 | Cure |
| 103 | Front left | Ref | 0 | | S. uberis($1 \times 10^2$) | New infection |
| 103 | Rear right | Ref | 0 | S. uberis ($>1 \times 10^5$) | 0 | Cure |
| 103 | Rear left | Ref | 0 | S. uberis ($>1 \times 10^5$) | Bacillus spp. ($1 \times 10^2$) | Cure + contamination |
| 104 | Front | Ref | 0 | S. | 0 | Cure |

FIGURE 36 (continued)

| | right | | | uberis(2.4x10³) | | |
|---|---|---|---|---|---|---|
| 104 | Front left | Ref | 0 | | Coryne spp (2.4x10²) | Control + minor infection |
| 104 | Rear right | Ref | 0 | | 0 | Control |
| 104 | Rear left | Ref | 0 | Contaminated | 0 | Infection Failure |
| 111 | Front right | Ref | 0 | | No clinical resoln. | No clinical resoln. |
| 111 | Front left | Ref | 0 | S. uberis (>1x10⁵) | No clinical resoln. | No clinical resoln. |
| 111 | Rear right | Ref | CNS (1x10⁴) | S. uberis (>1x10⁵) | No clinical resoln. | No clinical resoln. |
| 111 | Rear left | Ref | 0 | | No clinical resoln. | No clinical resoln. |

FIGURE 36 (continued)

METHODS OF TREATING MICROBIAL INFECTIONS, INCLUDING MASTITIS

TECHNICAL FIELD

This invention relates to methods of treatment and prevention of mastitis in a subject, intramammary veterinary antimicrobial compositions when used therein, and intramammary veterinary compositions when used therein.

BACKGROUND ART

Infection in both human and veterinary medicine is often caused by infection with bacteria of the *Staphylococcus* genus. Staphylococci are commensals of healthy mammals and birds and may be found on the skin and in associated glands, the nares, and transiently in the gastrointestinal tract as well as on the mucous membranes of the upper respiratory and lower urogenital tracts. While many species of *Staphylococcus* do not cause disease, certain species are capable of opportunistic pathogenicity. Two major pathogenic species of *Staphylococcus* of medical and veterinary significance are *Staphylococcus aureus* and *Staphylococcus pseudintermedius*. *Staphylococcus aureus* is associated with mastitis, skin and post-operative wound infections, while *Staphylococcus pseudintermedius* is commonly associated with pyogenic skin and post-operative wound infections in dogs and cats. *Staphylococcus pseudintermedius* has been identified as the main pathogenic species of veterinary significance in the *Staphylococcus pseudintermedius* group (SIG), which includes the strains *Staphylococcus intermedius*, *Staphylococcus pseudintermedius*, and *Staphylococcus delphini*.

Treatment of Bacteria with Antibiotics

The treatment of *Staphylococcus* bacteria can be difficult, particularly when subjects are infected with antibiotic-resistant strains. Bacterial infection by *Staphylococcus* is usually treated by the administration of β-lactam antimicrobials, a class of antimicrobials that target penicillin binding proteins (PBPs) which function in bacterial cell wall biosynthesis. These antimicrobials have bactericidal activity and function by inhibiting biosynthesis of the bacterial cell wall, resulting in high internal osmotic pressure, causing the bacteria to lyse. However, the use, overuse and misuse of antimicrobials in the treatment of bacterial infections has resulted in the emergence of antimicrobial resistant bacteria, to which the *Staphylococcus* genus is particularly prone. Resistance mechanisms in some species of *Staphylococcus* bacteria include the secretion of β-lactamase enzymes capable of hydrolysing the β-lactam ring of (β-lactam antimicrobials. To address this form of resistance, β-lactamase inhibitors, such as clavulanic acid are typically co-administered together with β-lactam antimicrobials, or synthetic analogues of penicillin, such as methicillin and cloxacillin, that are not substrates of β-lactamase, can be used.

Recently, even combination treatment with a β-lactam antimicrobial and a β-lactamase inhibitor has proved ineffective against antibiotic resistant strains of *Staphylococcus*. The emergence of methicillin-resistant *Staphylococcus aureus* isolates (MRSA) has effectively prevented the use of methicillin and other β-lactam antimicrobials that are not inactivated by β-lactamases. MRSA isolates have now been found to possess the mecA or mecC resistance gene which encodes mutated penicillin binding proteins or PBPs and confers resistance to penicillin, as well as to its analogues, and other β-lactam antimicrobials, including most cephalosporins and carbapenems. The issue of MRSA is often encountered in hospitals where MRSA bacterial isolates have been transferred to patients, as hospital-acquired MRSA (HA-MRSA) which is often maintained within hospitals through the contamination of hospital equipment and colonisation of staff. Unfortunately, patients who are immunosuppressed, have wounds or other trauma, are predisposed to easily contract MRSA infections, as well as infections with other species of staphylococci. This has caused many hospitals to implement anti-MRSA measures so as to reduce the incidence of HA-MRSA infections. A more recent concern has been the emergence of MRSA strains outside of hospitals, referred to as community-acquired MRSA (CA-MRSA). These strains are often even more virulent than HA-MRSA strains and may cause necrotising fasciitis. Most recently, livestock-associated MRSA (LA-MRSA) strains (for example sequence type [ST] 398 in Europe and ST9 in Asia) have been described as an emerging infection in pigs, poultry, cattle (including dairy cattle) and other livestock species.

In addition to MRSA, methicillin-resistance has also been observed in other species of staphylococci. For example, many strains of non-pathogenic, coagulase-negative species of *Staphylococcus* (MR-CNS) and *Staphylococcus pseudintermedius* (MRSP) are known to be methicillin-resistant. Other resistant species with different mechanisms of resistance include the Gram negative MDR *Pseudomonas aeruginosa*, and MDR *Escherichia coli* and *Enterobacter* species and the Gram positive vancomycin resistant Enterococcci (VRE) and penicillin and macrolide resistant *Streptococcus* spp.

Bovine Mastitis

An example of a major production-limiting disease of animals that requires treatment and prevention with antibiotics is bovine mastitis. Mastitis is the most frequent reason for antibiotic use in farm animals and constitutes a substantial cost to the dairy industry to eliminate infections and to prevent new cases of intramammary infection. Mastitis affects one or more of the four quarters of the bovine mammary gland or udder and can adversely affect the health of affected cows. Pathogens enter the mammary gland via the teat canal when the teat sphincter is relaxed following milking. In Australasia and elsewhere, the most common pathogens causing mastitis include *Streptococcus uberis*, *Staphylococcus aureus*, coagulase-negative staphylococci, *Streptococcus dysgalactiae* and *Streptococcus agalactiae*. Mastitis caused by MRSA is an emerging cause of lost productivity in dairy cattle that may potentially spread worldwide with some strains identified in dairy cattle (such as ST398) able to colonise, infect and cause disease in humans. Few products currently available for the treatment of mastitis in dairy cattle are effective against MRSA and no new antibacterials have been developed and registered for over 20 years, leading to an urgent need for new drugs and intramammary delivery systems to improve microbiological and clinical outcomes. Much of the historical failure to manage mastitis is due to an unmet need for validated intramammary delivery systems, systems that are safe to the animal and reliably and reproducibly efficacious against common mastitis pathogens.

Mastitis treatment is typically administered at two different stages in the cow's lactation cycle: the dry cow (DC) stage and the milking or lactating cow (LC) stage. Lactating cow therapy is administered to cows when the cows are in milk, while dry cow therapy is administered to cows when they are dried off at the end of lactation. Dry cow therapy is administered in order to remove those infections accumulated during the lactation stage, to prevent carry over to the next lactation, and to reduce the number of new infections contracted during the dry period. Mastitis treatment is often administered through the teat canal into the udder by intramammary injection or infusion.

Dry Cow Therapy

Dry cow treatment may be carried out by antimicrobial infusions or the introduction of a teat sealant. To prevent new infections during the dry period, the cow's natural defence mechanism includes the formation of a natural keratin plug which seals the teat. The keratin plug provides an effective barrier to the ingress of bacteria from the teat canal during the dry period. In most cows, the formation of the keratin plug occurs progressively over the first couple of weeks after the last milking and commencement of the dry period. Some cows do not form a keratin plug which pre-disposes them to acquiring infections during the dry period. Traumatic damage to the end of the teat can also seriously affect the ability of the teat canal to seal.

One approach for the treatment of bovine mastitis is the intramammary infusion of an antimicrobial formulation into the teat canal and the teat cistern. This standard technique is described in the textbook by Roger Blowey and Peter Edmondson (2010) entitled *Mastitis control in dairy herds* ($2^{nd}$ edition) and in particular the section entitled "Treatment and Dry Cow Therapy", CAB International, Wallingford, United Kingdom, 2010 at pages 196 to 197. The antimicrobial formulation is administered via a syringe that is partially inserted into the teat canal and the antibiotic is massaged up the teat and into and throughout the gland cistern.

Delay in or outright failure to naturally form a complete keratin plug during the dry period puts the cow at risk of experiencing new mastitis infections. One method of supplementing the teat's natural defences, and to ensure that the canal is sealed efficiently throughout the entire dry period, is by the use of an internal teat sealant. The use of an internal teat sealant was described in the mid 1970s by Meaney, W. J. "Dry period teat seal." *Vet Rec.* 99(2) (1976) 30.

The applicant is aware of two types of teat seal available to reduce dry period infections: the external film sealant, which provides a flexible barrier film over the teat end for up to 7 days, and the internal teat canal seal. The external seal is no longer commonly used, although it can be used in the late dry period if no internal seal has been administered. The internal seal is by far the most effective and the most commonly used. Most commonly the internal teat seal is a bismuth salt in a base that is infused into the teat canal at drying off. It has no antibacterial properties and hence strict hygiene during administration is essential. However, inclusion of antimicrobial substances within the internal teat seal composition can treat existing infections and enhance the likelihood of prevention of new infections. Effective dry cow treatment requires intramammary preparations that allow sustained and effective intramammary concentrations of antibacterial agents throughout the dry period. For example, the persistence of insoluble salts of penicillin (especially cloxacillin benzathine) formulated in a gel of aluminium monostearate and diluted in mineral oil (for example, see "Smith, A., F. K. Neave, et al. (1967) *Journal of Dairy Research* 34(01): 47-57").

Lactating Cow Therapy

Formulation of lactating cow preparations seeks to balance two opposing factors. The formulation must provide effective concentrations of the antibacterial substance throughout the mammary gland wherever the infecting agents are present (ie the site of infection) for as long as possible even in the face of continued milking twice or more frequently each day while minimising the period that milk must be withheld due to persistence of unacceptable concentrations of milk residues after the final infusion has been administered. In general, preparations for use in lactating cows provide high concentrations for hours or days and are formulated in quick release aqueous or oil (mineral or vegetable) bases.

The emergence of resistance to antibiotics has increased the need to provide alternative compounds capable of inhibiting multi-resistant bacterial strains, such as MRSA and MRSP.

Polyether Ionophores

Carboxyl polyethers, also known as polyether antibiotics or polyether ionophores, form electrically neutral complexes with monovalent or divalent cations, catalysing electrically silent exchanges of cations or protons across a variety of biological membranes. These compounds have been reported as showing a high degree of promise for the potential control of drug-resistant bacterial and protozoal infections however their use is severely limited by their high toxicity. These molecules function by rendering cell or intracellular membranes permeable to cations which are normally asymmetrically distributed across biological membranes thereby forming steep concentration gradients. Examples of polyether ionophores include lasalocid, monensin, narasin, salinomycin, semduramicin, maduramicin and laidlomycin.

However, the acute toxicity of these compounds due to their erythrocyte lysing activity and cardiac toxicity has effectively prevented their use in vivo. The main obstacle to the use of polyether ionophores as drugs to control human diseases is the issue of toxicity. In one example, as reported by Naujokat and Steinhart (2012, *J Biomed Biotechnol* 950658), considerable toxicity of salinomycin was reported in humans. In this case, the accidental inhalation and swallowing of about 1 mg/kg salinomycin by a 35-year-old male human, resulted in severe acute and chronic salinomycin toxicity with acute nausea together with photophobia, leg weakness, tachycardia and blood pressure elevation and a chronic (day 2 to day 35) creatine kinase elevation, myoglobinuria, limb weakness, muscle pain, and mild rhabdomyolysis. The European Food Safety Authority has recently published risk assessment data declaring an acceptable daily intake (ADI) of 5 μg/kg salinomycin for humans, since daily intake of more than 500 μg/kg salinomycin by dogs leads to neurotoxic effects, such as myelin loss and axonal degeneration (Naujokat and Steinhart, 2012, supra). In another example, Liu (1982, *Polyether Antibiotics. Naturally Occurring Acid Ionophores. Volume* 1. *Biology*. J. W. Westley. New York, Marcel Dekker Inc: 43-102) cites the high oral and parenteral toxicity of polyether ionophores is the likely reason why there has been no report on the in vivo antimicrobial activity of polyether ionophores.

The only current applications for polyether ionophores of which the applicant is aware, is their application as orally administered agents in veterinary medicine as controls of coccidiosis and for growth promotion.

Furthermore, not all polyether ionophores have shown significant activity against gram-positive bacteria such as *Staphylococcus aureus* and most do not have broad-spectrum activity against gram-negative bacteria. In view of the considerable toxicity in mammals, as reported by Naujokat and Steinhart (2012 supra), salinomycin has only been used as a coccidistat and growth promoter in livestock, and is not regarded as a suitable candidate for human drug development.

There remains a need for alternative antimicrobials in the treatment of infection by multi-resistant bacteria, such as MRSA and MRSP. However, as reported by the Infectious Diseases Society of America and the European Centre for Disease Control and Prevention, few new drugs are being developed that offer promisina results over existing treatments, and even fewer of these are specifically administered for the treatment of staphylococci (Gilbert et al. 2010, *Clinical Infectious Diseases,* 50(8):1081-1083).

The object of the present invention is to overcome some or all of the shortcomings of the prior art.

The discussion of the background art set out above is intended to facilitate an understanding of the present invention only. The discussion is not an acknowledgement or admission that any of the material referred to is or was part of the common general knowledge as at the priority date of the application.

SUMMARY OF INVENTION

According to one aspect of the invention, there is provided a method of treating mastitis in a subject, the method including the step of administering a therapeutically effective amount of a polyether ionophore, or a therapeutically acceptable salt thereof, to the mammary gland of the subject.

According to another aspect of the invention, there is provided a method of preventing mastitis in a subject, the method including the step of administering a therapeutically effective amount of a polyether ionophore, or a therapeutically acceptable salt thereof, to the mammary gland of the subject.

According to another aspect of the invention, there is provided the use of a polyether ionophore, or a therapeutically acceptable salt thereof, in the manufacture of a medicament for the treatment or prevention of mastitis in a subject.

The administration may be by intramammary administration, such as by intramammary injection or infusion via the teat canal.

Further features of the invention provide for the polyether ionophore, or the therapeutically acceptable salt thereof, to be selected from the group comprising monensin (also known as A-3823A), narasin A (also known as A-28086A), narasin B (also known as A-28086B), narasin D (also known as A-28086D), lasalocid, salinomycin, and maduramicin, alborixin (also known as S-14750A, CP-38,986), laidlomycin (also known as AB-78), lenoremycin (also known as A-130A, Ro21-6150), A-130B, A-130C, dianemycin (also known as A-150 (M5-16183), A-204A, A-204B, lonomycin (also known as A-218), deoxylaidlomycin (also known as A-712), calcimycin (also known as A-23187), septamycin (also known as BL-580α and A-28695A), A-28695B, K-41A (also known as A-32887), septamycin (also known as BL-580α$^b$), BL-580β, BL-580δ, BL-580Z, carriomycin, calmycin$^b$ (also known as A-23187), cationomycin, chloronoboritomycin A (also known as X-14766A), etheromycin (also known as CP-38,295, C 20-12, T-40517), deoxy-salinomycin (also known as SY-1), deoxy-epi-salinomycin (SY-2), deoxy-narasin, deoxy-epi-narasin, dianemycon$^b$ (also known as M5-16183, A-150), emericid (also known as lonomycin A and DE 3938), duamycin (also known as nigericin, helixin C, and azalomycin M), gridorixin, ionomycin, K-41B, lasalocid A (X-537A), lasalocid B, lasalocid C, lasalocid D, lasalocid E, iso-lasalocid A, leuseramycin, lomomycin B, lomomycin C, lysocellin, M-139603, monensin B, monensin C, monensin D, mutalomycin, noboritomycin A, noboritomycin B, RP 30504, RP 37454, salinomycin, salinomycin All, SY-4, SY-5, SY-8, tetronomycin, TM-531B, TM-531C, X-206, X-14547A, X-14667A, X-14667B, X-14868A, X-14868B, X-14868C, X-14868D, 5057, 6016.

Preferably the polyether ionophore is selected from the group comprising salinomycin; lasalocid; narasin; maduramicin; monensin, laidlomycin, and semduramicin.

The subject may be bovine, ovine, caprine, other ruminant species, camelids or equidae (including horses, donkeys and zebra). The subject may be human.

The polyether ionophore is administered to the mammary gland (two or four of which form the udder in a ruminant, or a breast in a human) of the subject at a dose selected from the group comprising 5 mg/gland to 2,000 mg/gland, preferably 20 mg/gland to 900 mg/gland, more preferably 40 mg/gland to 600 mg/gland, most preferably preferably 50 mg/gland to 500 mg/gland. For example, the polyether ionophore is be administered to the mammary gland of the subject at a dose selected from the group comprising 50 mg/gland, 60 mg/gland, 70 mg/gland, 80 mg/gland, 90 mg/gland, 100 mg/gland, 110 mg/gland, 120 mg/gland, 130 mg/gland, 140 mg/gland, 150 mg/gland, 160 mg/gland, 170 mg/gland, 180 mg/gland, 190 mg/gland, 200 mg/gland, 210 mg/gland, 220 mg/gland, 230 mg/gland, 240 mg/gland, 250 mg/gland, 260 mg/gland, 270 mg/gland, 280 mg/gland, 290 mg/gland, 300 mg/gland, 310 mg/gland, 320 mg/gland, 330 mg/gland, 340 mg/gland, 350 mg/gland, 360 mg/gland, 370 mg/gland, 380 mg/gland, 390 mg/gland, 400 mg/gland, 410 mg/gland, 420 mg/gland, 430 mg/gland, 440 mg/gland, 450 mg/gland, 460 mg/gland, 470 mg/gland, 480 mg/gland, 490 mg/gland, and 500 mg/gland.

In one embodiment, the polyether ionophore is administered to the subject at a dose range selected from the group comprising: 20 mg/teat canal to 900 mg/teat canal; and 50 mg/teat canal to 600 mg/teat canal.

In one embodiment of the invention, the polyether ionophore is administered to each mammary gland via the teat canal. For example, the polyether ionophore is administered via the teat canal using an intramammary device, such as a syringe. This is the preferred route in the treatment of mastitis in ruminants, such as bovines, as well as camelids and equids. In another embodiment, the polyether ionophore is administered to the subject via topical application to the surface of mammary gland, or by injection through the skin of the subject directly into the mammary gland or via the lactiferous ducts. For example, in the treatment of mastitis in humans, the ionophore is administered via topical application to the surface of the mammary gland or by infusion into the lactiferous ducts.

In one embodiment of the invention, the polyether ionophore is administered to the subject using a dosing regimen selected from the group consisting of: three times daily; two times daily; daily; every second day; once weekly; once fortnighty, once monthly, once per dry period, or twice per dry period. Preferably, the polyether ionophore is administered via the teat canal to each infected quarter or half of the subject's mammary gland (such as an udder), immediately following milking (or expressing milk to feed offspring). For example, if the subject is milked twice daily, the polyether ionophore is administered immediately after each milking. In a preferred embodiment, the polyether ionophore is administered to the subject during lactation twice daily, immediately after each milking for 2 days, 3 days, 7 days, 14 days, 21 days and one month, or until the signs of mastitis are no longer detectable; or, in the case of application to bovines, to cows when they are dried off at the end of lactation, or to heifers prior to first calving.

In one embodiment of the invention, the polyether ionophore is administered to the subject at a total dosage per teat canal (in ruminants) or per breast (in humans) selected from the group consisting of: between 1 mg to 1000 mg; between 10 mg and 500 mg; between, 10 mg and 400 mg; between 10 mg and 300 mg; between 10 mg and 200 mg; between 10 mg and 100 mg; and between 50 mg and 100 mg. Preferably, the polyether ionophore is administered to the subject at a total quantity per dose of 150 mg, 300 mg or 600 mg.

In one embodiment of the invention, the polyether ionophore is administered to the udder or breast of the subject. In one example, the polyether ionophore is administered to each quarter or half of the udder of the subject. In one example, the polyether ionophore is administered to the subject at a total dosage quantity per udder quarter (or udder half or per breast, dependent on anatomical differences between animal species) selected from the group consisting of: between 1 mg to 1000 mg; between 10 mg and 500 mg; between, 10 mg and 400 mg; between 10 mg and 300 mg; between 10 mg and 200 mg; between 10 mg and 100 mg; and between 50 mg and 100 mg. More preferably, the dose per quarter is 75 mg, 150 mg, 300 mg or 600 mg. In one embodiment, the dose administered per udder quarter (or udder half or per breast) is selected from the group comprising: 1 mg, 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 600 mg. In one example, the total dose per udder (four quarters or two halves) or both breasts is selected from these doses multipled by the number of mammary glands.

In one embodiment, the concentration of residual ionophore in the subject's milk after treatment is a range selected from the group consisting of: between 1 and 200 mg/L after 12 hours; between 0.1 and 5 mg/L after 24 hrs; between 0.01 and 2 mg/L after 48 hours; between 0.0001 and 1 mg/L after 72 hrs. Preferably, the concentration is selected from the group consisting of: less than 200 mg/L after 12 hours; less than 5 mg/L after 24 hours; less than 1 mg/L after 48 hours and less than 0.5 mg/l after 72 hours. Alternatively, the concentration is selected from the group consisting of: less than 10 mg/L after 12 hours; less than 1 mg/L after 24 hours; less than 0.1 mg/L after 48 hours and less than 0.01 mg/l after 72 hours. Alternatively, the concentration is selected from the group consisting of: less than 1 mg/L after 12 hours; less than 0.1 mg/L after 24 hours; less than 0.01 mg/L after 48 hours and less than 0.001 mg/l after 72 hours. Alternatively, the concentration is selected from the group consisting of: less than 0.1 mg/L after 12 hours; less than 0.01 mg/L after 24 hours; less than 0.001 mg/L after 48 hours and less than 0.0001 mg/l after 72 hours.

The microbe may be a prokaryote or a eukaryotic. Preferably, the microbe causing the mastitis is a bacterial agent selected from the group comprising, but not limited to, *Staphylococcus* spp, *Streptocccus* spp, *Bacillus* spp, *Enterococcus* spp, *Listeria* spp, *Mycoplasma* spp, and anaerobic bacteria. The bacterial agent may be selected from the group comprising, but not limited to, *Staphylococcus epidermidis, Staphylococcus simulans, Staphylococcus fells, Staphylococcus xylosus, Staphylococcus chromogenes, Staphylococcus wameri, Staphylococcus haemolyticus, Staphylococcus sciuri, Staphylococcus saprophyticus, Staphylococcus hominis, Staphylococcus caprae, Staphylococcus cohnii* subsp. *cohnii, Staphylococcus cohnii* subsp. *urealyticus, Staphylococcus capitis* subsp. *capitis, Staphylococcus capitis* subsp. *urealyticus, Staphylococcus hyicus, Staphylococcus aureus, Staphylococcus pseudintermedius, Staphylococcus delphini, Staphylococcus schleiferi* subsp. *coagulans, Staphylococcus aureus* subsp. *anaerobius, Streptococcus uberis, Streptococcus agalactiae, Streptococcus dysgalactiae, Streptococcus pyogenes, Streptococcus bovis, Streptococcus equi* subsp. *Zooepidemicus, Streptococcus equinus, Bacillus melaninogenicus, Bacillus pumilus, Bacillus licheniformis, Bacillus cereus, Bacillus subtilis, Bacillus anthracis, Enterococcus faecium, Enterococcus faecalis, Enterococcus durans, Listeria monocytogenes, Clostridium perfringens, Actinomyces bovis, Propionibacterium acnes, Propionibacterium granulosum, Eubacterium, Peptococcus indolicus, Peptostreptococcus anaerobius,* and *Mycoplasma bovis*.

More preferably, the bacterial agent is selected from a group comprising *Staphylococcus aureus, Staphylococcus epidermidis, Streptococcus uberis, Streptococcus agalactiae, Streptococcus dysgalactiae* and *Propionibacterium acnes*.

Most preferably, the bacterial agent is an antibiotic-sensitive strain or an antibiotic-resistant strain. Examples of antibiotic-resistant strains include MRSA and tetracycline resistant *Streptococcus* spp. In a preferred embodiment, the bacterial agent is MRSA.

In one embodiment, the bacterial agent is selected from the group comprising, but not limited to, coagulase-negative staphylococci (CNS). Examples of coagulase-negative staphylococci (CNS) include *Staphylococcus epidermidis* (isolated from bovine mastitis), *Staphylococcus simulans* (isolated from bovine mastitis or feline dermatitis), *Staphylococcus fells* (isolated from feline dermatitis), *Staphylococ-*

*cus xylosus* (isolated from bovine mastitis or bovine dermatitis), *Staphylococcus chromogenes* (isolated from bovine mastitis or caprine dermatitis), *Staphylococcus warneri* (isolated from caprine colonisation), *Staphylococcus haemolyticus* (isolated from caprine colonisation), *Staphylococcus sciuri* (isolated from porcine exudative epidermatitis), *Staphylococcus saprophyticus* (isolated from caprine colonisation), *Staphylococcus hominis* (isolated from porcine colonisation), *Staphylococcus caprae* (isolated from caprine colonisation), *Staphylococcus cohnii* subsp. *cohnii* (isolated from caprine colonisation), *Staphylococcus cohnii* subsp. *urealyticus* (isolated from caprine colonisation), *Staphylococcus capitis* subsp. *capitis* (isolated from bovine mastitis), *Staphylococcus capitis* subsp. *urealyticus* (isolated from bovine mastitis), and *Staphylococcus hyicus* (isolated from porcine exudative epidermatitis and bovine colonisation).

In another embodiment, the bacterial agent is selected from coagulase-positive staphylococci. For example, the bacterial agent may be selected from the group comprising, but not limited to *Staphylococcus aureus* (isolated from human, equine, canine and feline colonisation, bovine and ovine mastitis, and many species dermatitis and post-operative wound infection), *Staphylococcus pseudintermedius* (canine pyoderma, canine and feline colonisation, *Staphylococcus delphini* (dolphin suppurative skin lesions), *Staphylococcus schleiferi* subsp. *coagulans* (Canine otitis externa, canine, feline colonisation), and *Staphylococcus aureus* subsp. *anaerobius* (ovine lymphadenitis). In a most preferred embodiment, the bacterial agent is *Staphylococcus aureus*, which may be obtained from many lineages, many host adapted, including livestock associated MRSA of sequence type (ST) or clonal complex (CC) 398 or ST9; various human community associated CA-MRSA and hospital associated HA-MRSA).

In another embodiment, the bacterial agent is from the *Streptococcus* genus. For example, the bacterial agent may be selected from the group comprising, but not limited to, *Streptococcus uberis, Streptococcus agalactiae, Streptococcus dysgalactiae, Streptococcus pyogenes, Streptococcus bovis, Streptococcus equi* subsp. *zooepidemicus*, and *Streptococcus equinus*. The bacteria may be isolated from bovine mastitis.

In another embodiment, the bacterial agent is from the *Bacillus* genus. For example, the bacterial agent may be selected from the group comprising, but not limited to, *Bacillus melaninogenicus, Bacillus pumilus, Bacillus licheniformis, Bacillus cereus, Bacillus subtilis*, and *Bacillus anthracis*. The bacteria may be isolated from bovine mastitis.

In another embodiment, the bacterial agent is from the *Enterococcus* genus. For example, the bacterial agent may be selected from the group comprising, but not limited to, *Enterococcus faecium, Enterococcus faecalis*, and *Enterococcus durans*. The bacteria may be isolated from bovine mastitis.

In another embodiment, the bacterial agent is from the *Listeria* genus. For example, the bacterial agent may be *Listeria monocytogenes*. The bacteria may be isolated from bovine mastitis.

In another embodiment, the bacterial agent is anaerobic. For example, the bacterial agent may be selected from the group comprising, but not limited to, *Clostridium perfringens, Actinomyces bovis, Propionibacterium acnes, Propionibacterium granulosum, Eubacterium, Peptococcus indolicus*, and *Peptostreptococcus anaerobius*. The bacteria may be isolated from bovine mastitis.

In another embodiment, the microbe is of *Mycoplasma* genus. For example, the microbe may be *Mycoplasma bovis*. The bacterial agent may be isolated from bovine mastitis.

In a preferred embodiment, the microbe is *Staphylococcus aureus*. In most preferred embodiment, the microbe is MRSA.

It will be understood that polyether ionophores described herein are typically effective against gram-positive bacteria and a number of anaerobic bacteria, as well as fungi. The sensitivity of a microbe to the polyether ionophores described herein varies, dependent on the individual strain, but in general, gram-positive cocci and bacilli, as were some anaerobes such as *Clostridium, Eubacterium, Propionibacterium, Mycobacterium*, and *Streptomyces* are also susceptible. Fungi and yeasts, such as *Sclerotinia sclerotiorum, Monila laxa, Phomopsis mali, Botrytis cineria, Trichthecium roseum*, and *Verticillium albo-atrum* may also exhibit sensitivity to the polyether ionophores described herein.

According to another aspect of the invention, there is provided an intramammary pharmaceutical antimicrobial composition comprising a therapeutically effective amount of a polyether ionophore, or a therapeutically acceptable salt thereof. The intramammary veterinary antimicrobial composition of the invention may be used in the treatment of mastitis in humans.

According to another aspect of the invention, there is provided an intramammary veterinary antimicrobial composition comprising a therapeutically effective amount of a polyether ionophore, or a therapeutically acceptable salt thereof.

The intramammary veterinary antimicrobial composition of the invention may be used in the treatment of mastitis in bovines.

The antimicrobial composition of the invention may be formulated to treat mastitis in dry cows or to treat mastitis in lactating cows. Formulations for the treatment of mastitis in dry cows may further comprise excipients intended for gelling or otherwise solidifying the formulation and sealing the teat canal. Formulations of the treatment of mastitis in lactating cows may further comprise excipients intended for rapid release such that a formulation that is not retained in the mammary gland of the lactating cow.

In one embodiment, the intramammary antimicrobial composition comprises impurities, wherein the quantity of impurities as a percentage of the total weight of the composition is selected from the group consisting of: less than 20% impurities (by total weight of the composition); less than 15% impurities; less than 10% impurities; less than 8% impurities; less than 5% impurities; less than 4% impurities; less than 3% impurities; less than 2% impurities; less than 1% impurities: less than 0.5% impurities; less than 0.1% impurities. In one embodiment, the intramammary antimicrobial composition comprises microbial impurities or secondary metabolites, wherein the quantity of microbial impurities as a percentage of the total weight of the composition is selected from the group consisting of: less than 5%; less than 4%; less than 3%; less than 2%; less than 1%; less than 0.5%; less than 0.1%; less than 0.01%; less than 0.001%. In one embodiment, the intramammary antimicrobial composition is sterile and stored in a sealed and sterile container. In one embodiment, the intramammary antimicrobial composition contains no detectable level of microbial contamination.

The composition of the invention may comprise a further antimicrobial agent. The further antimicrobial agent may be an antifungal agent.

In one embodiment, the antifungal agent is selected from the group comprising, but not limited to, Echinocandins (Anidulafungin, Caspofungin, Micafungin), Polyenes (Amphotericin B, Candicidin, Filipin, Fungichromin, Hachimycin, Hamycin, Lucensomycin, Mepartricin, Natamycin, Nystatin, Pecilocin, Perimycin, Griseofulvin, Oligomycins, Pyrrolnitrin, Siccanin, and Viridin. The antifungal agent may be a synthetic compound selected from the group comprising, but not limited to, Allylamines (Butenafine, Naftifine, Terbinafine) Imidazoles (Bifonazole, Butoconazole, Chlormidazole, Cloconazole, Clotrimazole, Econazole, Fenticonazole, Flutrimazole, Isoconazole, Ketoconazole, Lanoconazole, Miconazole, Neticonazole, Omoconazole, Oxiconazole Nitrate, Sertaconazole, Sulconazole, Tioconazole), Thiocarbamates (Liranaftate, Tolciclate, Tolindate, Tolnaftate), Triazoles (Fluconazole, Isavuconazole, Itraconazole, Posaconazole, Ravuconazole, Saperconazole, Terconazole, Voriconazole), Acrisorcin, Amorolfine, Bromosalicylchloranilide, Buclosamide, Calcium Propionate, Chlorphenesin, Ciclopirox, Cloxyquin, Coparaffinate, Exalamide, Flucytosine, Haloprogin, Hexetidine, Loflucarban, Nifuratel, Potassium Iodide, Propionic Acid, Pyrithione, Salicylanilide, Sodium Propionate, Sulbentine, Tenonitrozole, Triacetin, Undecylenic Acid, and Zinc Propionate.

In another embodiment, the antifungal agent is selected from the group comprising, but not limited to, Amorolfine, Amphotericin B, Anidulafungin, Bifonazole, Bromochlorosalicylanilide, Butenafine Hydrochloride, Butoconazole Nitrate, Caspofungin Acetate, Chlormidazole Hydrochloride, Chlorphenesin, Ciclopirox, Climbazole, Clotrimazole, Cloxiquine, Croconazole Hydrochloride, Eberconazole Nitrate, Econazole, Enilconazole, Fenticonazole Nitrate, Fluconazole, Flucytosine, Flutrimazole, Fosfluconazole, Griseofulvin, Isoconazole, Itraconazole, Ketoconazole, Lanoconazole, Liranaftate, Luliconazole, Mepartricin, Micafungin Sodium, Miconazole, Naftifine Hydrochloride, Natamycin, Neticonazole Hydrochloride, Nifuroxime, Nystatin, Omoconazole Nitrate, Oxiconazole Nitrate, Parconazole Hydrochloride, Pentamycin, Pirocotone olamine, Posaconazole, Propionic Acid, Pyrrolnitrin, Ravuconazole, Sertaconazole Nitrate, Siccanin, Sodium Parachlorobenzoate, Sulconazole Nitrate, Terbinafine, Terconazole, Tioconazole, Tolciclate, Tolnaftate, Triacetin, Trimetrexate Glucuronate, Undecenoic Acid, and Voriconazole The composition of the invention may comprise an antibiotic adjunct selected from the group comprising, but not limited to, β-Lactamase Inhibitors (Clavulanic Acid, Sulbactam, Sultamicillin, Tazobactam), Renal Dipeptidase Inhibitors (Cilastatin), and Renal Protectant (Betamipron).

In one embodiment, the composition of the invention comprises a further antibiotic selected from the group comprising, but not limited to, Aminoglycosides (Amikacin, Arbekacin, Bambermycins, Butirosin, Dibekacin, Dihydrostreptomycin, Fortimicins, Gentamicin, Isepamicin, Kanamycin, Micronomicin, Neomycin, Netilmicin, Paromomycin, Ribostamycin, Sisomicin, Spectinomycin, Streptomycin, Tobramycin), Amphenicols (Azidamfenicol, Chloramphenicol, Thiamphenicol) Ansamycins (Rifamide, Rifampin, Rifamycin SV, Rifapentine, Rifaximin), β-Lactams, Carbacephems (Loracarbef) Carbapenems (Biapenem, Doripenem, Ertapenem, Imipenem, Meropenem, Panipenem), Cephalosporins (Cefaclor, Cefadroxil, Cefamandole, Cefatrizine, Cefazedone, Cefazolin, Cefcapene, Cefdinir, Cefditoren, Cefepime, Cefetamet, Cefixime, Cefmenoxime, Cefodizime, Cefonicid, Cefoperazone, Ceforanide, Cefoselis, Cefotaxime, Cefotiam, Cefozopran, Cefpimizole, Cefpiramide, Cefpirome, Cefpodoxime, Cefprozil, Cefroxadine, Cefsulodin, Ceftaroline, Ceftazidime, Cefteram, Ceftezole, Ceftibuten, Ceftizoxime, Ceftobiprole Medocaril, Ceftriaxone, Cefuroxime, Cefuzonam, Cephacetrile, Cephalexin, Cephaloglycin, Cephaloridine, Cephalothin, Cephapirin, Cephradine, Pivcefalexin), Cephamycins (Cefbuperazone, Cefmetazole, Cefminox, Cefotetan, Cefoxitin), Monobactams (Aztreonam, Carumonam), Oxacephems (Flomoxef, Moxalactam), Penems (Faropenem, Ritipenem), Penicillins (Amdinocillin, Amdinocillin Pivoxil, Amoxicillin, Ampicillin, Apalcillin, Aspoxicillin, Azidocillin, Azlocillin, Bacampicillin, Carbenicillin, Carindacillin, Clometocillin, Cloxacillin, Cyclacillin, Dicloxacillin, Epicillin, Fenbenicillin, Floxacillin, Hetacillin, Lenampicillin, Metampicillin, Methicillin Sodium, Mezlocillin, Nafcillin, Oxacillin, Penamecillin, Penethamate Hydriodide, Penicillin G, Penicillin G Benzathine, Penicillin G Procaine, Penicillin N, Penicillin O, Penicillin V, Phenethicillin Potassium, Piperacillin, Pivampicillin, Propicillin, Quinacillin, Sulbenicillin, Sultamicillin, Talampicillin, Temocillin, Ticarcillin), Lincosamides (Clindamycin, Lincomycin), Macrolides (Azithromycin, Cethromycin, Clarithromycin, Dirithromycin, Erythromycin, Erythromycin Acistrate, Erythromycin Estolate, Erythromycin Glucoheptonate, Erythromycin Lactobionate, Erythromycin Propionate, Erythromycin Stearate, Fidaxomicin, Josamycin, Leucomycin, Midecamycins, Miokamycin, Oleandomycin, Primycin, Rokitamycin, Rosaramicin, Roxithromycin, Spiramycin, Telithromycin, Troleandomycin), Polypeptides (Amphomycin, Bacitracin, Bacitracin Zinc, Capreomycin, Colistin, Dalbavancin, Daptomycin, Enduracidin, Enviomycin, Fusafungine, Gramicidin(s), Gramicidin S, Iseganan, Oritavancin, Polymyxin, Quinupristin, Ramoplanin, Ristocetin, Teicoplanin, Telavancin, Thiostrepton, Tuberactinomycin, Tyrocidine, Tyrothricin, Vancomycin, Viomycin), Tetracyclines (Chlortetracycline, Clomocycline, Demeclocycline, Doxycycline, Guamecycline, Lymecycline, Meclocycline, Methacycline, Minocycline, Oxytetracycline, Pipacycline, Rolitetracycline, Tetracycline, Tigecycline), Others (Cycloserine, Dalfopristin, Fosfomycin, Fusidic Acid, Mupirocin, Pristinamycin, Retapamulin and Virginiamycin).

In another embodiment, the composition of the invention further comprises a synthetic antibiotic selected from the group comprising, but not limited to, 2,4-Diaminopyrimidines (Brodimoprim, Iclaprim, Tetroxoprim, Trimethoprim), Nitrofurans (Furaltadone, Furazolium Chloride, Nifuratel, Nifurfoline, Nifurpirinol, Nifurtoinol, Nitrofurantoin) Oxazolidinones (Linezolid), Peptides (Omiganan, Pexiganan), Quinolones and Analogs (Balofloxacin, Besifloxacin, Cinoxacin, Ciprofloxacin, Clinafloxacin, Enoxacin, Finafloxacin, Fleroxacin, Flumequine, Garenoxacin, Gatifloxacin, Gemifloxacin, Grepafloxacin, Lomefloxacin, Miloxacin, Moxifloxacin, Nadifloxacin, Nalidixic Acid, Norfloxacin, Ofloxacin, Oxolinic Acid, Pazufloxacin, Pefloxacin, Pipemidic Acid, Piromidic Acid, Prulifloxacin, Rosoxacin, Rufloxacin, Sitafloxacin, Sparfloxacin, Tosufloxacin, Trovafloxacin), Sulfonamides (Acetyl Sulfamethoxypyrazine, Chloramine-B, Chloramine-T, ninbln-rAminP T, Mafenide, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadoxine, Sulfaethidole, Sulfaguanidine, Sulfaguanole, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfannetrole, Sulfamidochrysoidine, Sulfamoxole, Sulfanilamide, N4-Sulfanilylsulfanilamide, Sulfanilylurea, N-Sulfanilyl-3,4-xylamide, Sulfaperine, Sulfaphenazole, Sulfaproxyline, Sulfapyrazine, Sulfapyridine, Sulfathiazole, Sulfathiourea, Sulfisomidine, Sulfisoxazole), Sulfones (Acediasulfone, Dapsone, Glucosulfone Sodium, Succisulfone, Sulfanilic Acid, p-Sulfanilylbenzylamine, Sulfoxone Sodium, Thiazolsulfone), Clofoctol, Methenamine, Metronidazole, Nitroxoline, Taurolidine, and Xibornol.

In another embodiment, the composition of the invention further comprises an antibiotic selected from the group comprising, but not limited to, Acediasulfone Sodium, Amikacin, Aminosalicylic Acid, Amoxicillin, Ampicillin, Apramycin, Arbekacin Sulfate, Arsanilic Acid, Aspoxicillin, Astromicin Sulfate, Avilamycin, Avoparcin, Azidamfenicol, Azidocillin Sodium, Azithromycin, Azlocillin, Aztreonam, Bacampicillin Hydrochloride, Bacitracin, Balofloxacin, Bambermycin, Baquiloprim, Bekanamycin Sulfate, Benethamine Penicillin, Benzathine Benzylpenicillin, Benzathine Phenoxymethylpenicillin, Benzylpenicillin, Besifloxacin, Betamipron, Biapenem, Brodimoprim, Capreomycin Sulfate, Carbadox, Carbenicillin Sodium, Carindacillin Sodium, Carumonam Sodium, Cefaclor, Cefadroxil, Cefalexin, Cefalonium, Cefaloridine, Cefalotin Sodium, Cefamandole, Cefapirin Sodium, Cefatrizine, Cefazolin, Cefbuperazone, Cefcapene Pivoxil Hydrochloride, Cefdinir, Cefditoren Pivoxil, Cefepime Hydrochloride, Cefetamet, Cefixime, Cefmenoxime Hydrochloride, Cefmetazole, Cefminox Sodium, Cefodizime Sodium, Cefonicid Sodium, Cefoperazone Sodium, Ceforanide, Cefoselis Sulfate, Cefotaxime Sodium, Cefotetan, Cefotiam Hydrochloride, Cefovecin Sodium, Cefoxitin Sodium, Cefozopran Hydrochloride, Cefpiramide, Cefpirome Sulfate, Cefpodoxime Proxetil, Cefprozil, Cefquinome Sulfate, Cefradine, Cefsulodin Sodium, Ceftaroline Fosamil Acetate, Ceftazidime, Cefteram Pivoxil, Ceftezole Sodium, Ceftibuten, Ceftiofur, Ceftizoxime Sodium, Ceftobiprole Medocaril, Ceftriaxone Sodium, Cefuroxime, Cethromycin, Chloramphenicol, Chloroxine, Chlorquinaldol, Chlortetracycline, Ciclacillin, Cilastatin Sodium, Cinoxacin, Ciprofloxacin, Clarithromycin, Clavulanic Acid, Clemizole Penicillin, Clindamycin, Clioquinol, Clofazimine, Clofoctol, Clometocillin Potassium, Cloxacillin, Colistin Sulfate, Co-tetroxazine, Co-trifamole, Co-trimoxazole, Cycloserine, Dalbavancin, Danofloxacin Mesilate, Dapsone, Daptomycin, Delamanid, Demeclocycline, Dibekacin Sulfate, Dicloxacillin, Difloxacin Hydrochloride, Dihydrostreptomycin Sulfate, Dirithromycin, Doripenem, Doxycycline, Enoxacin, Enrofloxacin, Ertapenem Sodium, Erythromycin, Ethambutol Hydrochloride, Ethionamide, Etimicin Sulfate, Faropenem Sodium, Fidaxomicin, Fleroxacin, Flomoxef Sodium, Florfenicol, Flucloxacillin, Flumequine, Flurithromycin Ethyl Succinate, Formosulfathiazole, Fosfomycin, Framycetin Sulfate, Ftivazide, Furaltadone Hydrochloride, Furazidin, Fusafungine, Fusidic Acid, Gamithromycin, Garenoxacin Mesilate, Gatifloxacin, Gemifloxacin Mesilate, Gentamicin Sulfate, Gramicidin, Gramicidin S, Halquinol, Ibafloxacin, Iclaprim, Imipenem, Isepamicin, Isoniazid, Josamycin, Kanamycin Acid Sulfate, Kitasamycin, Latamoxef Disodium, Levofloxacin, Lincomycin, Linezolid, Lomefloxacin Hydrochloride, Loracarbef, Lymecycline, Mafenide, Magainins, Mandelic Acid, Marbofloxacin, Mecillinam, Meclocycline, Meleumycin, Meropenem, Methacycline, Methenamine, Meticillin Sodium, Mezlocillin, Micronomicin Sulfate, Midecamycin, Minocycline, Morinamide, Moxifloxacin Hydrochloride, Mupirocin, Nadifloxacin, Nafcillin Sodium, Nalidixic Acid, Neomycin, Netilmicin Sulfate, Nifuroxazide, Nifurpirinol, Nifurtoinol, Nifurzide, Nisin, Nitrofurantoin, Nitrofurazone, Nitroxoline, Norfloxacin, Norvancomycin Hydrochloride, Novobiocin, Ofloxacin, Oleandomycin Phosphate, Orbifloxacin, Oritavancin, Ormetoprim, Oxacillin Sodium, Oxolinic Acid, Oxytetracycline, Panipenem, Pazufloxacin Mesilate, Pefloxacin Mesilate, Penethamate Hydriodide, Pheneticillin Potassium, Phenoxymethylpenicillin, Phthalylsulfacetamide, Phthalylsulfathiazole, Pipemidic Acid, Piperacillin, Pirlimycin Hydrochloride, Piromidic Acid, Pivampicillin, Pivmecillinam, Polymyxin B Sulfate, Pradofloxacin, Pristinamycin, Procaine Benzylpenicillin, Propicillin Potassium, Protionamide, Prulifloxacin, Pyrazinamide, Quinupristin/Dalfopristin, Ramoplanin, Retapamulin, Ribostamycin Sulfate, Rifabutin, Rifampicin, Rifamycin Sodium, Rifapentine, Rifaximin, Rokitamycin, Rolitetracycline, Rosoxacin, Roxithromycin, Rufloxacin Hydrochloride, Sarafloxacin Hydrochloride, Sisomicin Sulfate, Sitafloxacin, Sparfloxacin, Spectinomycin, Spiramycin, Streptomycin, Succinylsulfathiazole, Sulbactam, Sulbenicillin Sodium, Sulfabenzamide, Sulfacarbamide, Sulfacetamide, Sulfachlorpyridazine, Sulfachrysoidine, Sulfaclozine, Sulfadiazine, Sulfadiazine Silver, Sulfadicramide, Sulfadimethoxine, Sulfadimidine, Sulfadoxine, Sulfafurazole, Sulfaguanidine, Sulfamerazine, Sulfamethizole, Sulfamethoxazole, Sulfamethoxypyridazine, Sulfamethylthiazole, Sulfametopyrazine, Sulfametrole, Sulfamonomethoxine, Sulfamoxole, Sulfanilamide, Sulfapyridine, Sulfaquinoxaline, Sulfathiazole, Sulfathiazole Silver, Sulfatroxazole, Sulfisomidine, Sultamicillin, Taurolidine, Tazobactam Sodium, Teicoplanin, Telavancin, Telithromycin, Temocillin, Terizidone, Tetracycline, Tetroxoprim, Thenoic Acid, Thiamphenicol, Thioacetazone, Thiostrepton, Tiamulin, Ticarcillin Monosodium, Tigecycline, Tildipirosin, Tilmicosin, Tobramycin, Tosufloxacin, Trimethoprim, Troleandomycin, Tulathromycin, Tylosin, Tylvalosin Tartrate, Tyrothricin, Valnemulin, Vancomycin, Virginiamycin, and Xibornol.

Preferably, the composition of the invention comprises a further antibiotic selected from the group comprising, but not limited to, penicillin G, penethamate, cloxacillin, nafcillin, ampicillin, amoxycillin, clavulanic acid, gentamicin, streptomycin, neomycin, framycetin, tetracyclines, tilmicosin and pirlimycin.

The composition of the invention may further comprise an excipient selected from the group comprising, but not limited to, binders and compression aids, coatings and films, colouring agents diluents and vehicles disintegrants, emulsifying and solubilising agents, flavours and sweeteners, repellents, glidants and lubricants, plasticisers, preservatives, propellants, solvents, stabilisers, suspending agents and viscosity enhancers. In an embodiment of the invention, the composition further comprises citric acid, It will be understood that such excipients may result in any change of the pH of the composition.

The composition may be in the form of a teat sealant comprising a polyether ionophore as described herein, together with gelling substance such as those commonly used in the art. For example, bismuth subnitrate 65% (w/w) in a paraffin oil gel base, or bismuth subnitrate, liquid paraffin, aluminium stearate and a gel base.

According to a further aspect of the invention there is provided a therapeutic device when used in treatment of mastitis in the subject, the device comprising an intramammary injector and a composition of the invention comprising a therapeutically effective amount of a polyether ionophore, or a therapeutically acceptable salt thereof.

According to a further aspect of the invention there is provided a veterinary device when used in treatment of mastitis in the subject, the device comprising an intramammary injector and a composition of the invention comprising a therapeutically effective amount of a polyether ionophore, or a therapeutically acceptable salt thereof.

Preferably, the device is adapted for immediate, sustained or controlled release of the ionophore.

In a further aspect, the invention is the use of a polyether ionophore, or a therapeutically acceptable salt thereof, in the manufacture of medicament for the treatment or prevention of mastitis in a subject. Preferably, the use comprises administering a therapeutically effective amount of a polyether ionophore, or a therapeutically acceptable salt thereof, to the mammary gland of a subject. Preferably, the polyether ionophore is administered to the subject in a dose in the range of 20 mg/teat canal to 900 mg/ teat canal or 50 mg/ teat canal to 600 mg/ teat canal.

In a further aspect, the invention is a method, a composition, a device, or a use, substantially as described herein with reference to the accompanying examples and figures.

In a further aspect, the invention is the composition according to claim 14, the device according to claim 24, and the use according to claim 27, substantially as described herein with reference to the accompanying examples and figures.

Terms used herein will have their customary meanings in the art unless specified. As set out herein, the following terms refer to the polyether ionophores indicated:

In regards to the Examples and Figures, LP 1088 refers to Salinomycin; LP 1369 refers to Lasalocid; LP 4525 refers to Narasin; LP 6315 refers to Maduramicin; and LP 9666 refers to Monensin.

As used herein, the term lasalocid, (also known as Avatec, Bovatec, Antibiotic X-537A, Ionophore X-4537A, and Ro 2-2985, CAS registry number 25999-31-9 (acid), 25999-20-6 (Na salt)) refers to a compound having the following chemical structure:

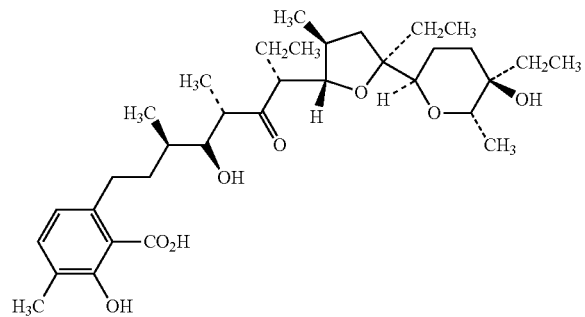

As used herein, the term monensin, (also known as Coban, Rumensin, Monensic acid, and A 3823A, CAS registry number 17090-79-8 (acid), 22373-78-0 (Na salt)) refers to a compound having the following chemical structure:

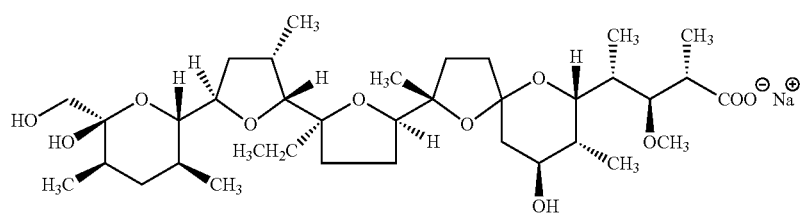

As used herein, the term salinomycin, (also known as Coxistac, Posistac, Salocin, Ovicox, AHR-3096, K-364, and K-748364A, CAS registry number 53003-10-4 (acid), 55721-31-8 (Na salt)) refers to a compound having the following chemical structure:

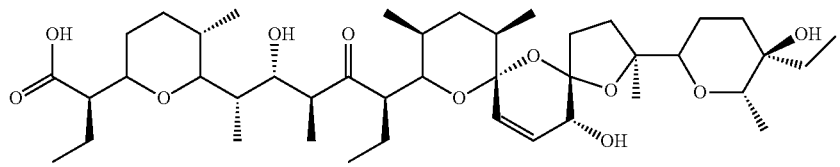 [SMILES: CC[C@@H](C(=O)O)C1CC[C@H](C)C([C@@H](C)[C@H](O)[C@H](C)C(=O)[C@H](CC)C2O[C@]3(C=C[C@@H](O)[C@]4(CC[C@@](C)(C5CC[C@](O)(CC)[C@H](C)O5)O4)O3)[C@H](C)C[C@@H]2C)O1]

As used herein, the term narasin, (also known as Monteban, 4-methylsalinomycin, Compound 79891, A-28086 factor A, C-7819B, CAS registry number 55134-13-9 (acid)) refers to a compound having the following chemical structure:

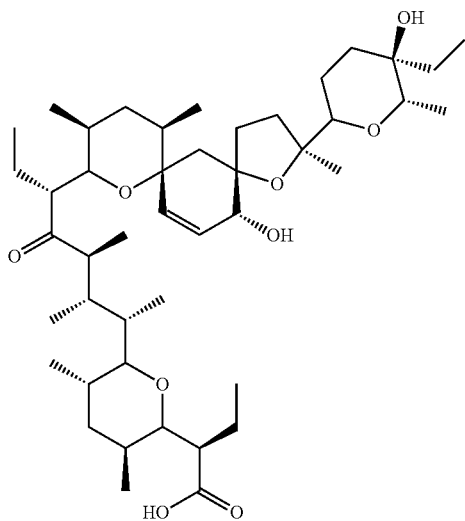 [SMILES: CC[C@@H](C(=O)O)C1OC([C@@H](C)[C@H](C)[C@H](C)C(=O)[C@H](CC)C2O[C@]3(C=C[C@@H](O)[C@]4(CC[C@@](C)(C5CC[C@](O)(CC)[C@H](C)O5)O4)C3)[C@H](C)C[C@@H]2C)[C@@H](C)C[C@@H]1C]

As used herein, the term maduramicin refers to a compound having the following chemical structure (represented below as maduramicin ammonium):

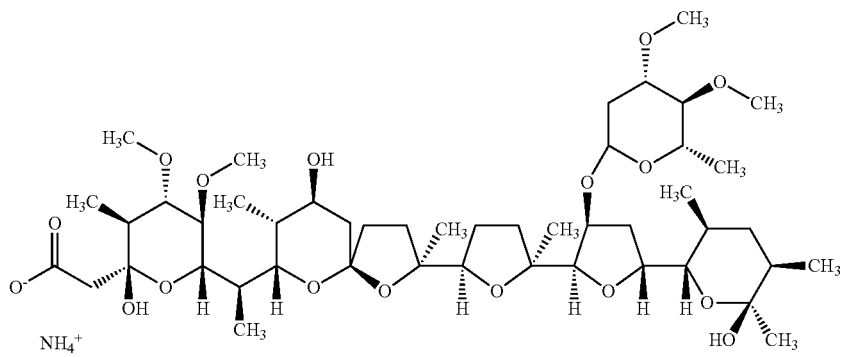 [SMILES: CO[C@@H]1[C@@H](OC)[C@H](C)[C@@](O)(CC(=O)[O-])O[C@H]1[C@H](C)[C@H]1O[C@@]2(CC[C@@](C)([C@H]3CC[C@@](C)([C@@H]4O[C@@H]([C@H]5O[C@](C)(O)[C@H](C)C[C@@H]5C)C[C@@H]4OC4C[C@H](OC)[C@@H](OC)[C@H](C)O4)O3)O2)C[C@H](O)[C@H]1C ; [NH4+]]

standard procedures known in the art. Intramammary application of the compositions of the invention is expected to result in treatment and prevention of mastitis in a subject by way of exposure to a polyether ionophore, with minimal systemic absorption via the mammary/blood barrier of the subject. In this way, therapeutically effective amounts of a polyether ionophore may be applied in the treatment of mastitis without exposing the subject to substantially toxic doses of the substance.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

Figures 6, 7, 8:
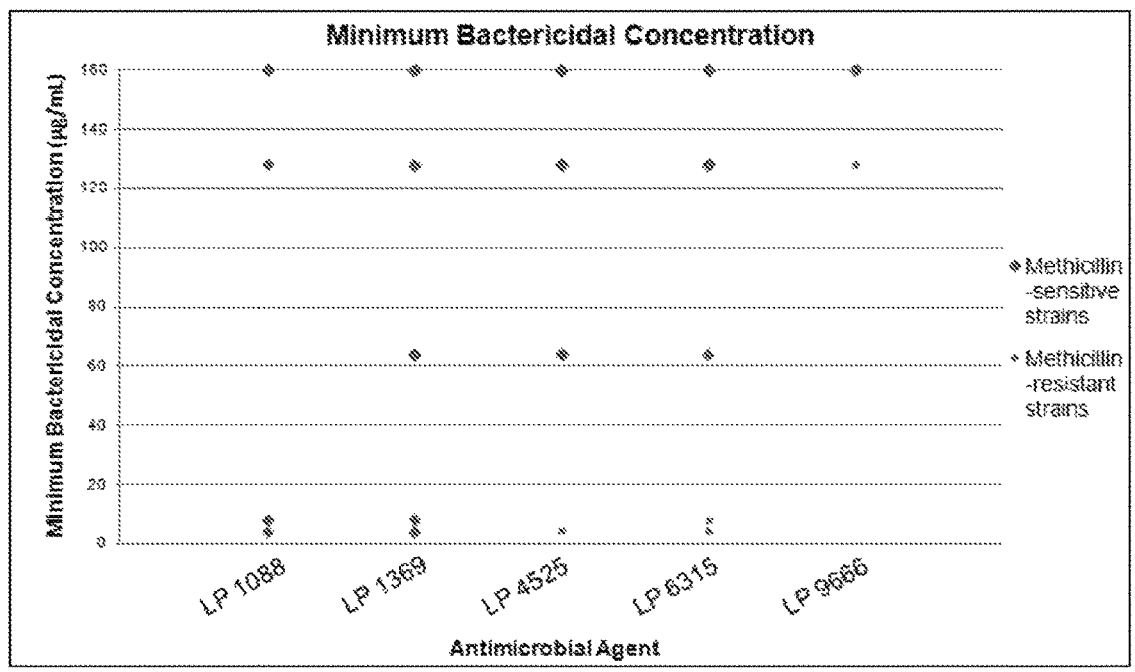
Figures 9, 10:
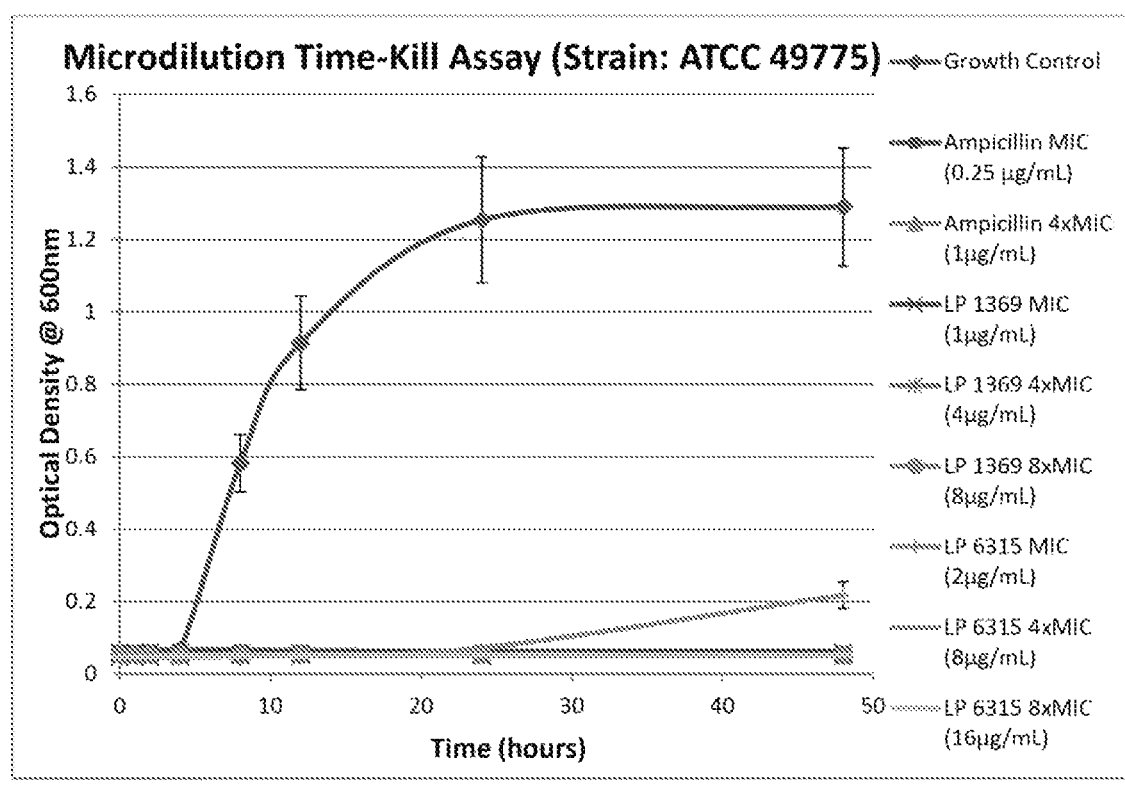
Figure 11:
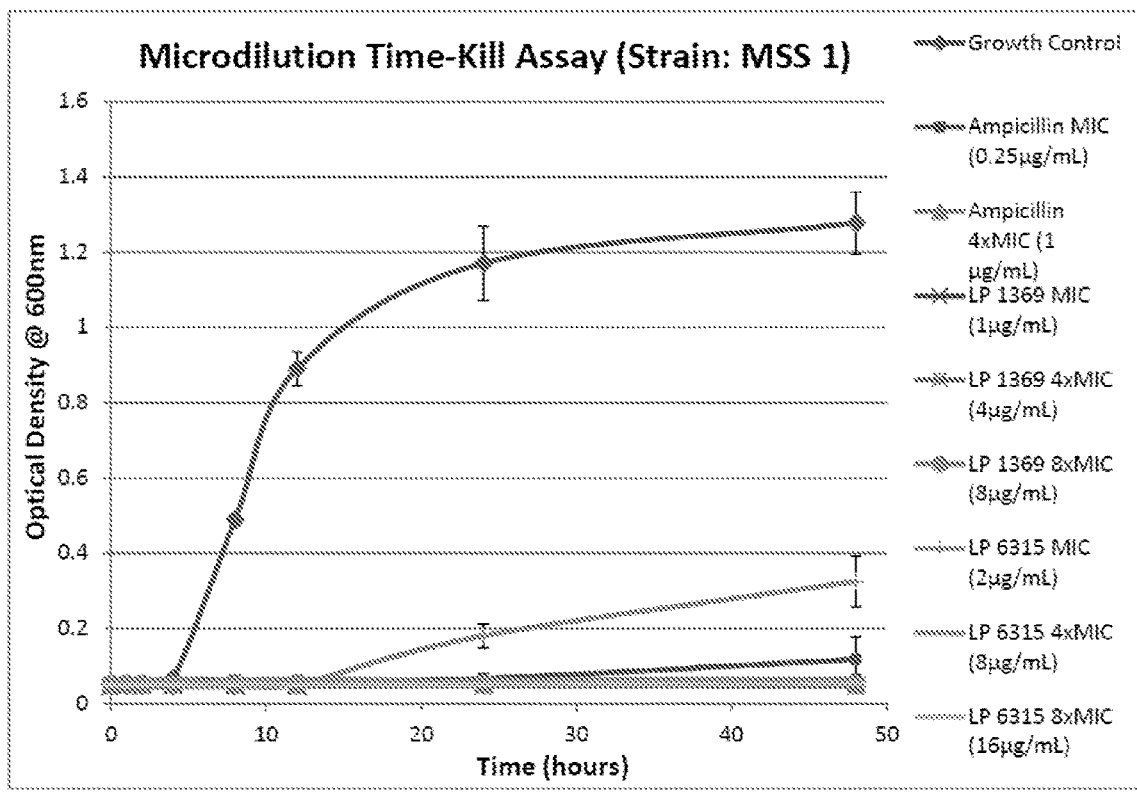
Figure 12:
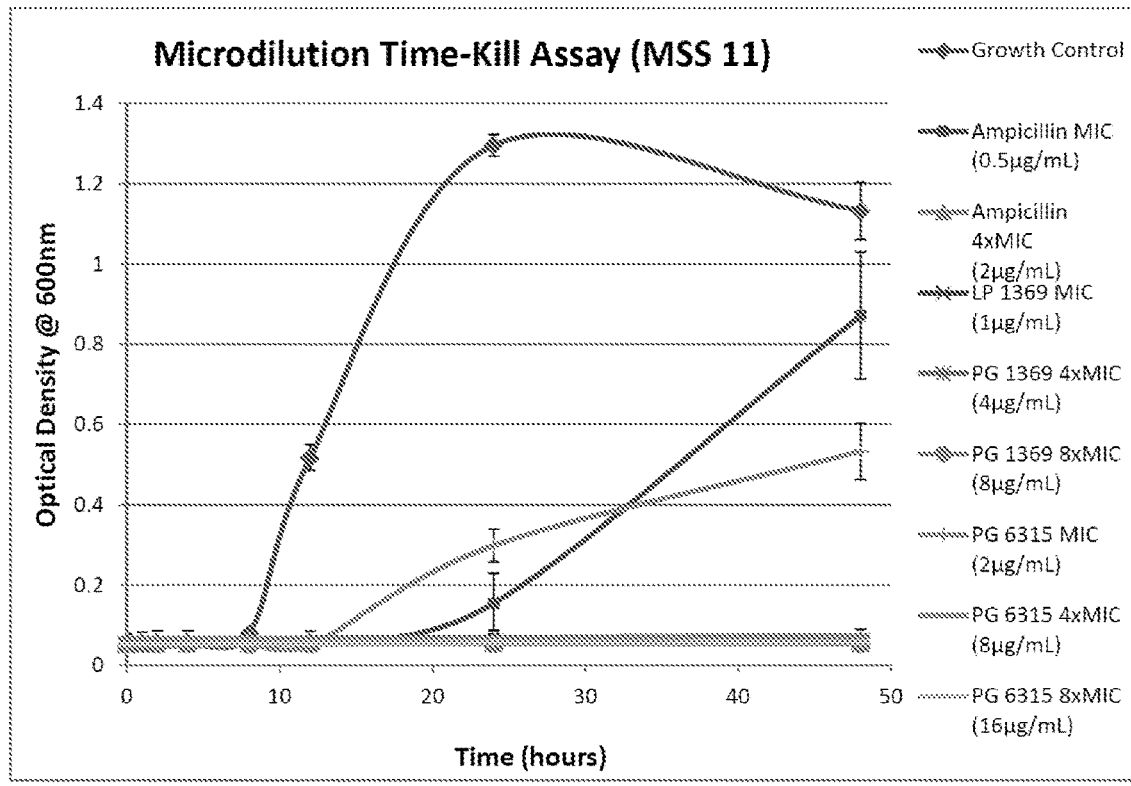
Figure 13:
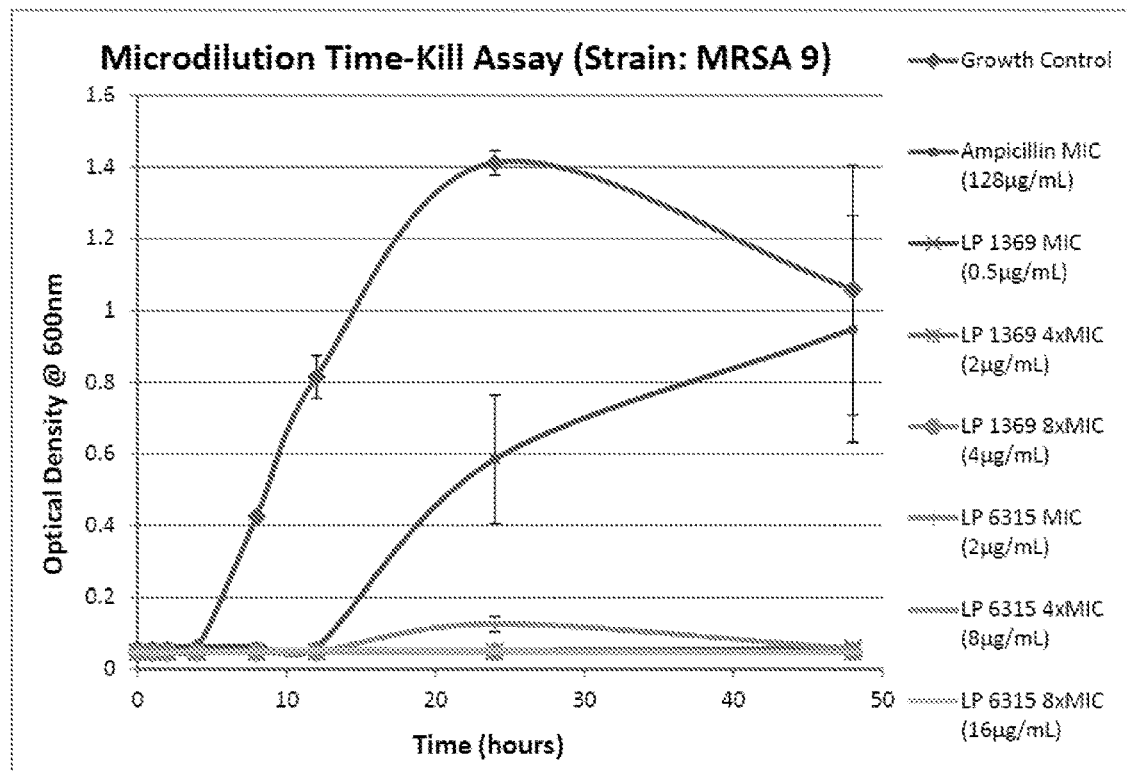
Figure 14:
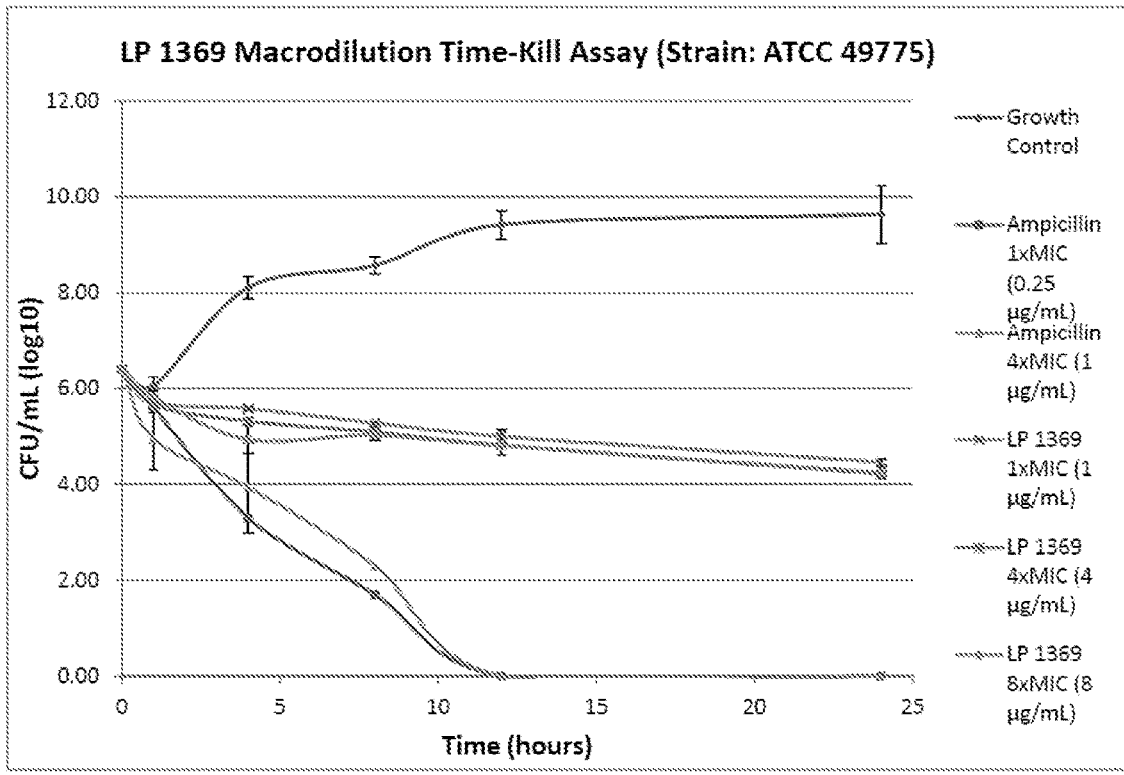
Figures 15, 16:
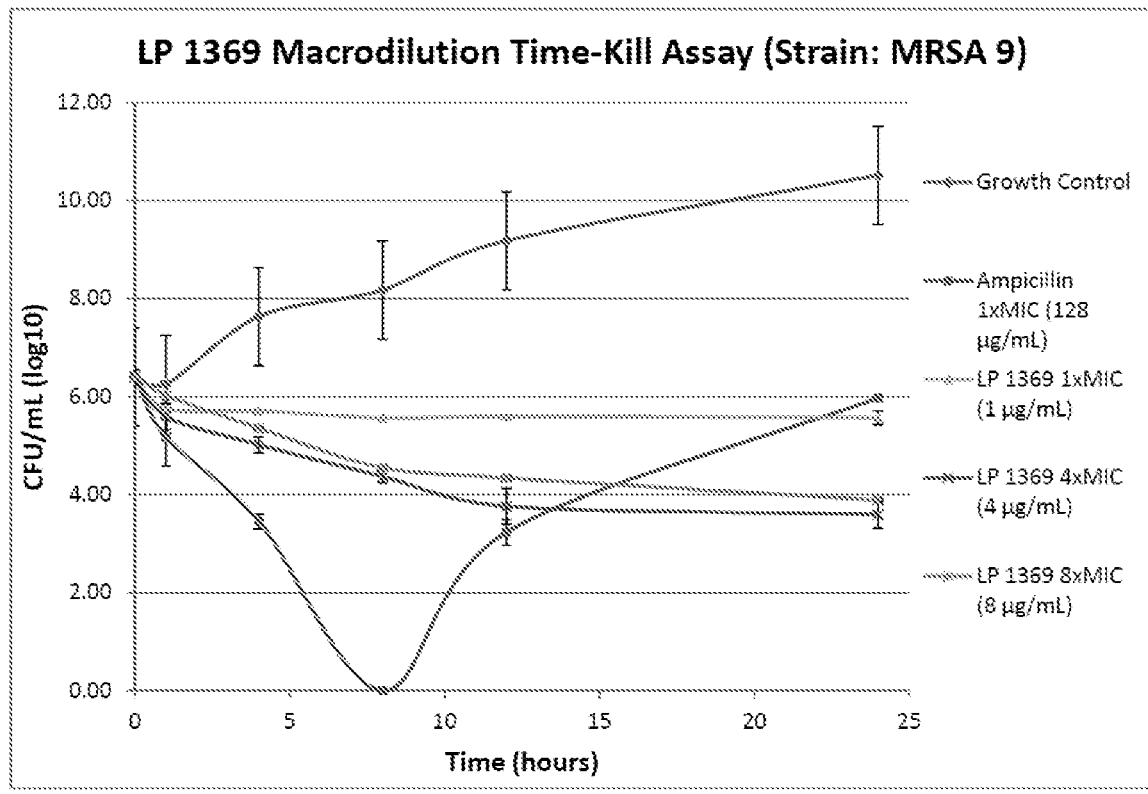
Figure 17:
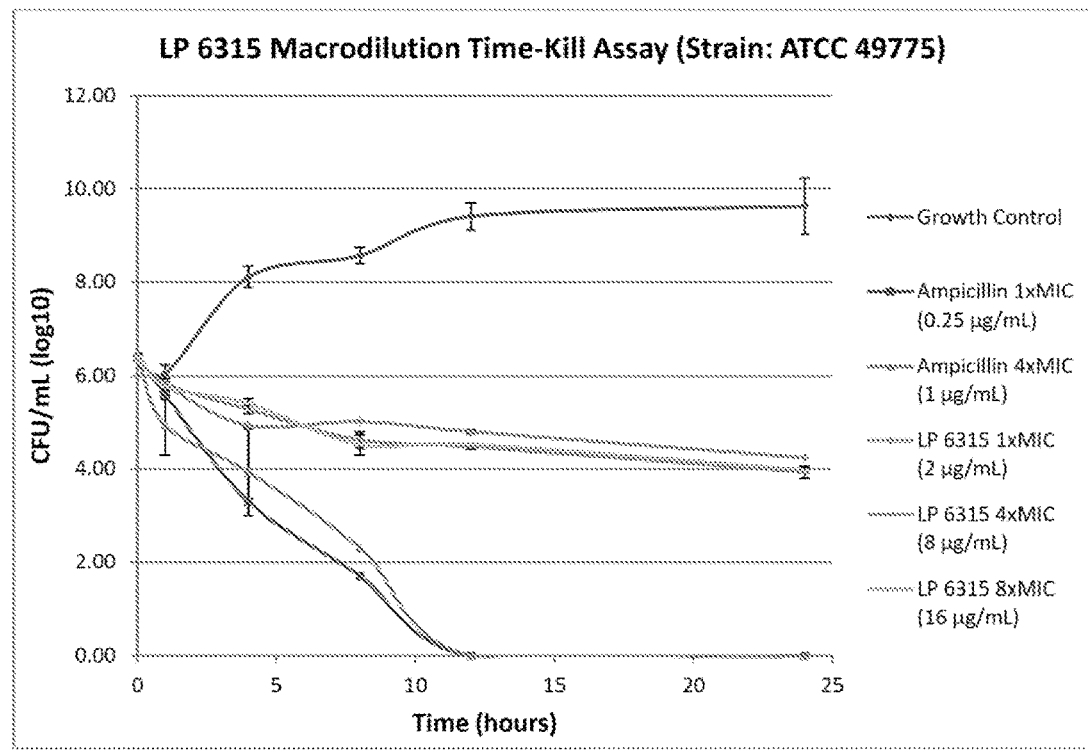
Figure 18:
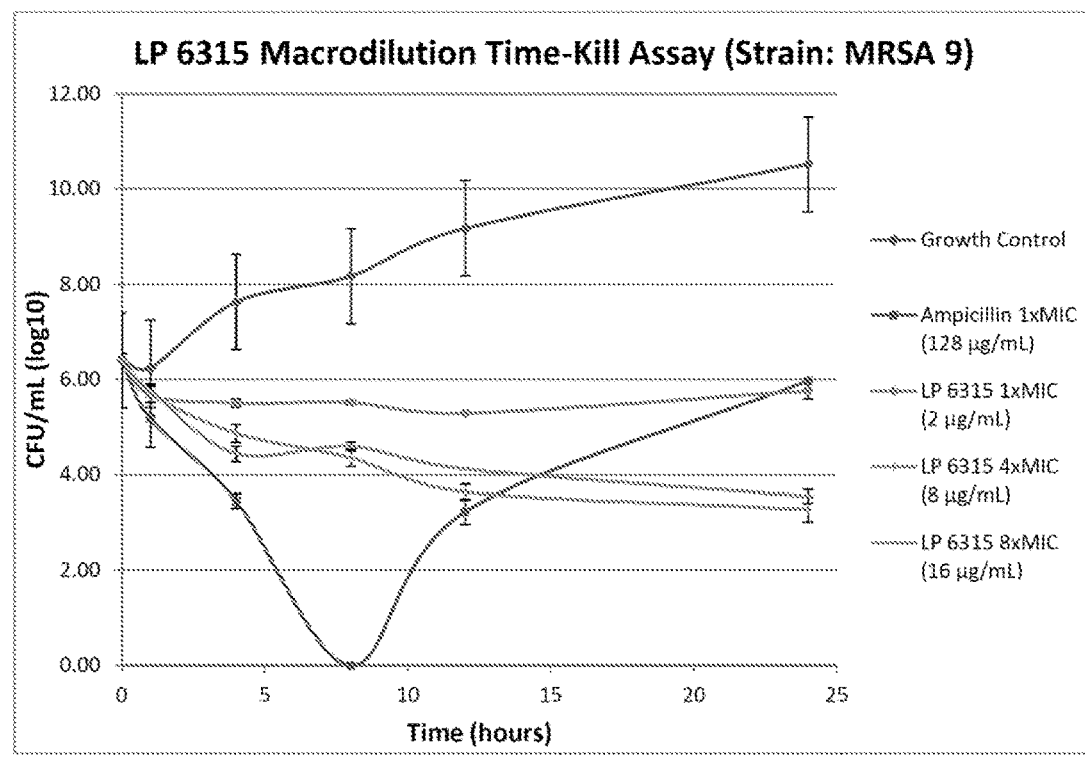
Figures 19, 20:
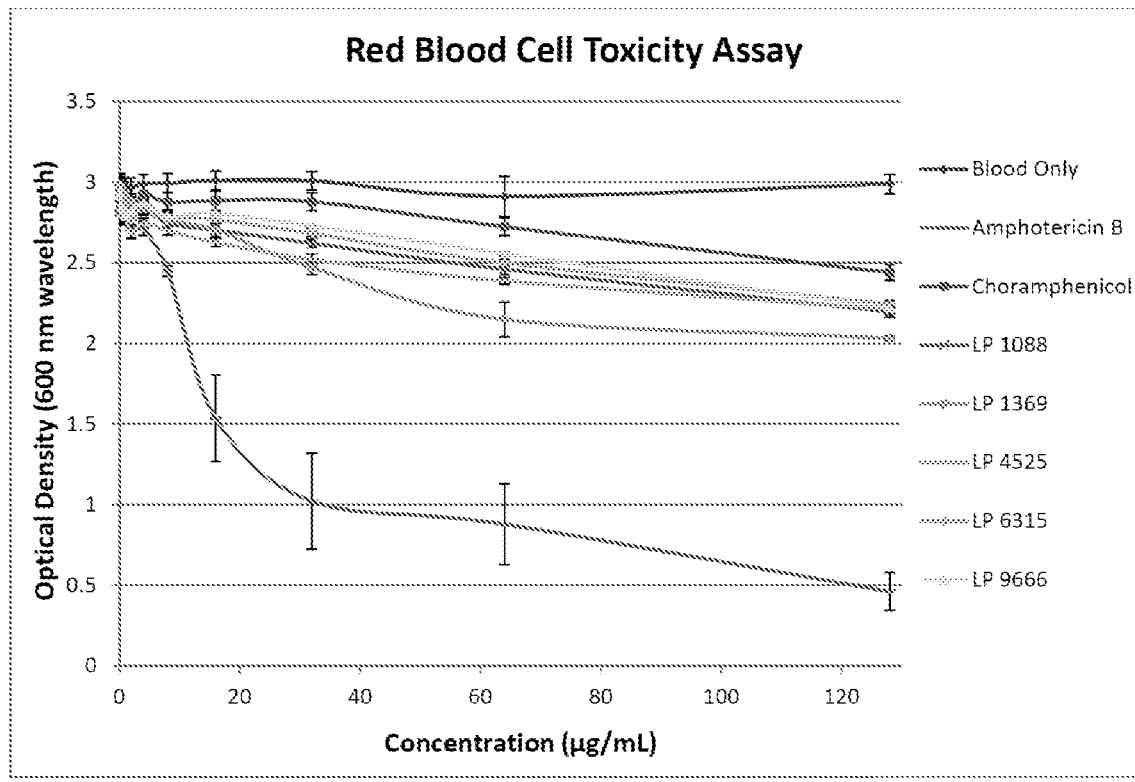
Figures 24, 25, 26:
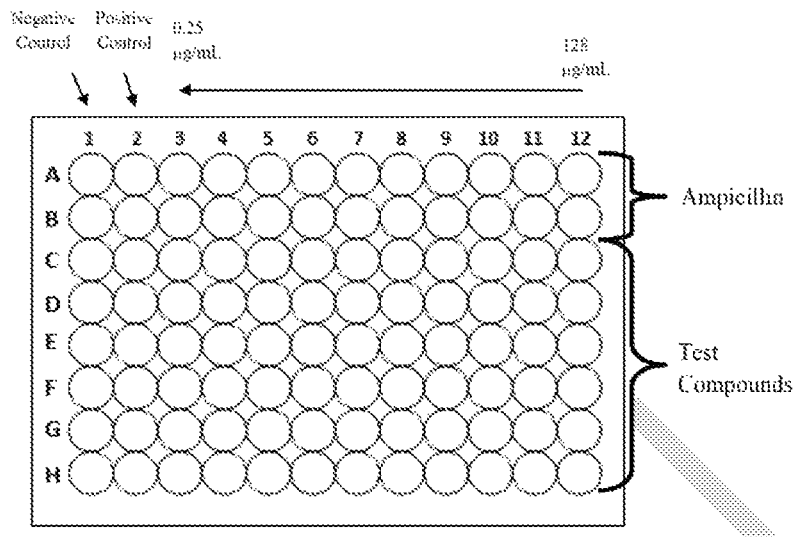
Figure 33:
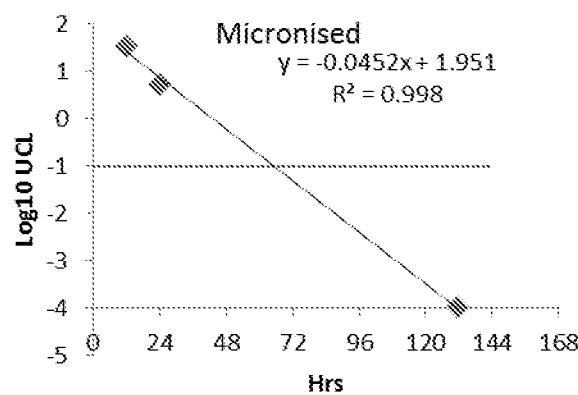
Figure 34:
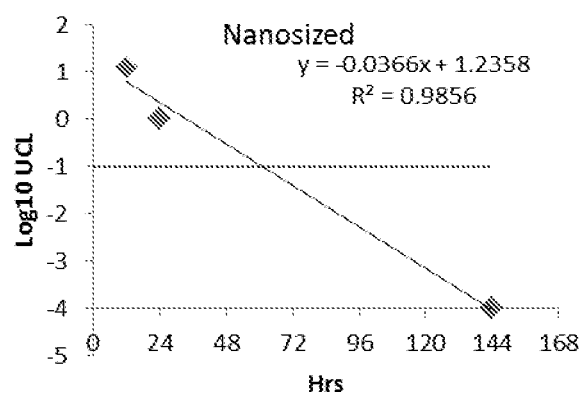
Figure 35:
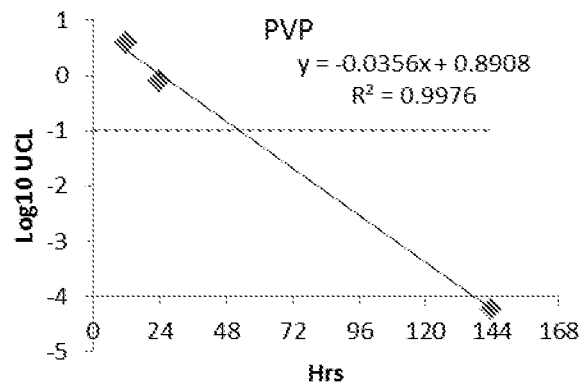
Figure 37:
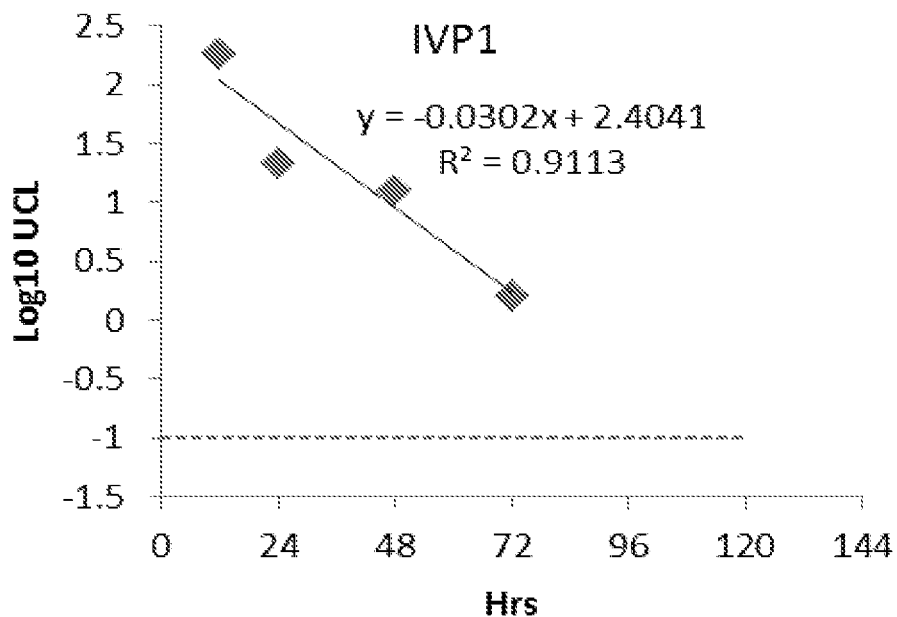
Figure 38:
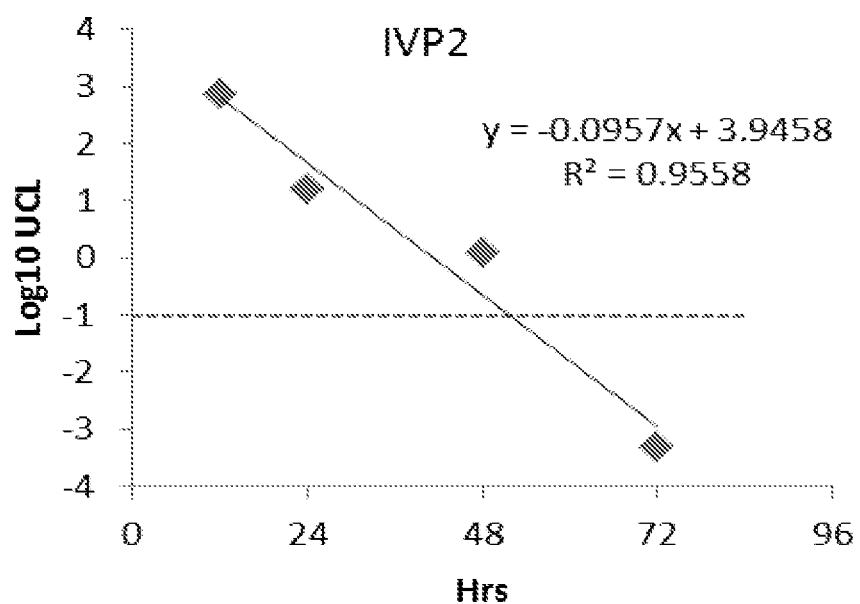

It is an advantage of the invention that the compositions described are applied in a method of treating and preventing mastitis. Intramammary application may be carried out using intramammary injectors or teat sealants according to FIG. 5 shows a table illustrating the $MIC_{50}$, $MIC_{90}$ and MIC ranges for the methicillin-sensitive isolates for ampicillin and the five test compounds according to Example 1;

FIG. 6 shows a table illustrating the $MIC_{50}$, $MIC_{90}$ and MIC ranges for the methicillin-resistant isolates for ampicillin and the five test compounds according to Example 1;

FIG. 7 shows a graph of the minimum bactericidal concentrations for individual isolates separated into methicillin-sensitive and methicillin-resistant strains; values shown as higher than 128 μg/mL represent strains where no MBC value was obtained within the range of concentrations tested (0.25-128 μg/mL) according to Example 1;

FIG. 8 shows a table showing the $MBC_{50}$, $MBC_{90}$ and MBC ranges for the methicillin-sensitive isolates for the five test compounds according to Example 1;

FIG. 9 shows a table illustrating the $MBC_{50}$, $MBC_{90}$ and MBC ranges for the methicillin-resistant isolates for the five test compounds according to Example 1;

FIG. 10 shows a graph illustrating the optical density measurements obtained for the microdilution time-kill assay of ATCC 49775 over 48 hours using various concentrations of ampicillin, LP 1369 and LP 6315 compared to a growth curve according to Example 1;

FIG. 11 shows a graph illustrating the optical density measurements obtained for the microdilution time-kill assay of MSS 1 over 48 hours using various concentrations of ampicillin, LP 1369 and LP 6315 compared to a growth curve according to Example 1;

FIG. 12 shows a graph illustrating the optical density measurements obtained for microdilution time-kill assay of MSS 11 over 48 hours using various concentrations of ampicillin, LP 1369 and LP 6315 compared to a growth curve according to Example 1;

FIG. 13 shows a graph illustrating the optical density measurements obtained for microdilution time-kill assay of MRSA over 48 hours using various concentrations of ampicillin, LP 1369 and LP 6315 compared to a growth curve according to Example 1;

FIG. 14 shows a graph illustrating the number of viable colonies (log10) of ATCC 49775 over 24 hours compared to introduction to one, four and eight times the MIC of LP 1369, one and four times the MIC of ampicillin according to Example 1;

FIG. 15 shows a graph illustrating the number of viable colonies (log10) of MRSA 9 over 24 hours compared to introduction to one, four and eight times the MIC of LP 1369, one and four times the MIC of ampicillin according to Example 1;

FIG. 16 shows a table setting out the change in number of CFU/mL (log10) for ATCC 49775 and MRSA 9 over 24 hours in various concentrations of ampicillin or LP 1369 compared to a growth control according to Example 1;

FIG. 17 shows a graph illustrating the number of viable colonies (log10) of ATCC 49775 over 24 hours compared to introduction to one, four and eight times the MIC of LP 6315, one and four times the MIC of ampicillin according to Example 1;

FIG. 18 shows a graph illustrating the number of viable colonies (log10) of MRSA 9 over 24 hours compared to introduction to one, four and eight times the MIC of LP 6315, one and four times the MIC of ampicillin according to Example 1;

FIG. 19 shows a table illustrating the change in number of CFU/mL (log10) for ATCC 49775 and MRSA 9 over 24 hours in various concentrations of ampicillin or LP 6315 compared to a growth control according to Example 1;

FIG. 20 shows a graph illustrating the optical density readings obtained for the red blood cell toxicity assay for each test compound at various concentrations as well as positive and negative controls and blood only readings according to Example 1; and FIG. 21 is a table setting out the isolate collection and the dog breed source following biochemical identification of the *Staphylococcus pseudintermedius* isolates including resistance profile according to Example 2;

FIG. 22 is a table setting out the resistance profile of the *Staphylococcus pseudintermedius* isolates collected according to Example 2;

FIG. 23 is a table setting out the MIC profile of ampicillin and LP compounds of the *Staphylococcus pseudintermedius* isolates collected according to Example 2;

FIG. 24 is a diagrammatic representation showing the 96 well microtitre tray layout for Minimum Inhibitory Concentration Testing according to Example 3;

FIG. 25 is a table showing the $MIC_{50}$, $MIC_{90}$, MIC range and $MBC_{50}$, $MBC_{90}$, and MBC range of each compound tested according to Example 3;

FIG. 26 is a table showing the $MIC_{50}$, $MIC_{90}$, MIC range and $MBC_{50}$, $MBC_{90}$, and MBC range of each compound tested against 14 *Staphylococcus aureus* isolates according to Example 3;

FIG. 27 is a table showing the $MIC_{50}$, $MIC_{90}$, MIC range and $MBC_{50}$, $MBC_{90}$, and MBC range of each compound tested against six coagulase-negative *Staphylococcus aureus* isolates according to Example 3;

FIG. 28 is a table showing the $MIC_{50}$, $MIC_{90}$, MIC range and $MBC_{50}$, $MBC_{90}$, and MBC range of each compound tested against 12 *Staphylococcus agalactiae* isolates according to Example 3;

FIG. 29 is a table showing the $MIC_{50}$, $MIC_{90}$, MIC range and $MBC_{50}$, $MBC_{90}$, and MBC range of each compound tested against six *Staphylococcus uberis* isolates according to Example 3;

FIG. 30 is a table showing the profiles of the bovine mastitis isolates according to Example 3;

FIG. 31 is a table showing the MICs of individual bovine mastitis isolates according to Example 3;

FIG. 32 is a table showing the MBCs of individual bovine mastitis isolates according to Example 3;

FIG. 33 is a graph showing the weighted UCLs of the concentration of LP1369 in milk at 3 milkings for cows treated at a single occasion with microsized;

FIG. 34 is a graph showing the weighted UCLs of the concentration of LP1369 in milk at 3 milkings for cows treated at a single occasion with nanosized;

FIG. 35 is a graph showing the weighted UCLs of the concentration of LP1369 in milk at 3 milkings for cows treated at a single occasion with PVP;

FIG. 36 is a table presenting the results of the microbial results of milk samples collected at pre-infection, post-infection and post-treatment as discussed in Examples 7 and 8;

FIG. 37 is a graph showing weighted Upper Confidence Limit of the concentration of LP1369 in milk at 4 milkings for quarters treated on 6 occasions (consecutive milkings) with IVP1; and FIG. 38 is a graph showing Weighted UCLs of the concentration of LP1369 in milk at 4 milkings for non-treated quarters in cows treated in two other quarters on 6 occasions (consecutive milkings) with IVP2

DESCRIPTION OF EMBODIMENTS

General

Before describing the present invention in detail, it is to be understood that the invention is not limited to particular exemplified methods or compositions disclosed herein. It is also to be understood that the terminology used herein is for the purpose of describing particular embodiments of the invention only, and is not intended to be limiting.

All publications referred to herein, including patents or patent applications, are incorporated by reference in their entirety. However, applications that are mentioned herein are referred to simply for the purpose of describing and disclosing the procedures, protocols, and reagents referred to in the publication which may have been used in connection with the invention. The citation of any publications referred to herein is not to be construed as an admission that the invention is not entitled to antedate such disclosure by virtue of prior invention.

In addition, the carrying out of the present invention makes use of, unless otherwise indicated, conventional microbiological techniques within the skill of the art. Such conventional techniques are known to the skilled worker.

As used herein, and in the appended claims, the singular forms "a", "an", and "the" include the plural unless the context clearly indicates otherwise.

Unless otherwise indicated, all technical and scientific terms used herein have the same meanings as commonly understood by one of ordinary skill in the art to which this invention belongs. Although any materials and methods similar to, or equivalent to, those described herein may be used to carry out the present invention, the preferred materials and methods are herein described.

The invention described herein may include one or more ranges of values (e.g. size, concentration, dose etc). A range of values will be understood to include all values within the range, including the values defining the range, and values adjacent to the range that lead to the same or substantially the same outcome as the values immediately adjacent to that value which define the boundary of the range.

The phrase "therapeutically effective amount" as used herein refers to an amount sufficient to inhibit bacterial growth associated with bacterial carriage or mastitis. That is, reference to the administration of the therapeutically effective amount of polyether ionophores according to the methods or compositions of the invention refers to a therapeutic effect in which substantial bacteriocidal or bacteriostatic activity causes a substantial inhibition of mastitis. The term "therapeutically effective amount" as used herein, refers to a nontoxic but sufficient amount of the composition to provide the desired biological, therapeutic, and/or prophylactic result. The desired results include elimination of bacterial carriage or reduction and/or alleviation of the signs, symptoms, or causes of a disease, or any other desired alteration of a biological system. An effective amount in any individual case may be determined by one of ordinary skill in the art using routine experimentation. In relation to a pharmaceutical or veterinary composition, effective amounts can be dosages that are recommended in the modulation of a diseased state or signs or symptoms thereof. Effective amounts differ depending on the veterinary composition used and the route of administration employed. Effective amounts are routinely optimized taking into consideration various factors of a particular patient, such as age, weight, gender, etc and the area affected by disease or disease causing microorganisms.

As referred to herein, the terms "microbe" and "microbial" refers to a microscopic organism comprising either a single cell wall clusters of cells and encompasses, but is not limited to, prokaryotes such as bacteria and archaea; and forms of eukaryotes such as protozoan, fungi, algae. Preferably the terms "microbe" and "microbial" refers to prokaryotes and eukaryotes. The prokaryotes may refer to bacteria, such as *Staphylococcus* spp, *Streptocccus* spp, *Bacillus* spp, *Enterococcus* spp, *Listeria* spp, *Mycoplasma* spp, and anaerobic bacteria. The terms may refer to an antibiotic-sensitive strain or an antibiotic-resistant strain. In a preferred embodiment, the terms refer to MRSA. In another preferred embodiment, the terms refer to MRSP.

In one embodiment, the terms "microbe" and "microbial" refer to one or more of coagulase-negative staphylococci (CNS): *Staphylococcus epidermidis. Staphylococcus simulans, Staphylococcus felis, Staphylococcus xylosus, Staphylococcus chromogenes, Staphylococcus warneri, Staphylococcus haemolyticus, Staphylococcus sciuri, Staphylococcus saprophyticus, Staphylococcus hominis, Staphylococcus caprae,), Staphylococcus cohnii* subsp. *Cohnii, Staphylococcus cohnii* subsp. *urealyticus, Staphylococcus capitis* subsp. *capitis, Staphylococcus capitis* subsp. *urealyticus*, and *Staphylococcus hyicus*.

In another embodiment, the terms "microbe" and "microbial" refer to one or more of coagulase-positive staphylococci: *Staphylococcus aureus, Staphylococcus pseudintermedius, Staphylococcus delphini, Staphylococcus schleiferi* subsp. *Coagulans*, and *Staphylococcus Aureus* subsp. *anaerobius*.

In another embodiment, the bacterial agent is from the *Streptococcus* genus. For example, the bacterial agent may be selected from the group comprising, but not limited to, *Streptococcus uberis, Streptococcus agalactiae, Streptococcus dysgalactiae, Streptococcus pyogenes, Streptococcus bovis, Streptococcus equi* subsp. *Zooepidemicus*, and *Streptococcus equinus*. The bacteria may be isolated from bovine mastitis.

In another embodiment, the terms "microbe" and "microbial" refer to one or more of bacterial agent of the *Baccillus* genus: *Bacillus melaninogenicus, Bacillus pumilus, Bacillus licheniformis, Bacillus cereus, Bacillus subtilis*, and *Bacillus anthracis*.

In another embodiment, the terms "microbe" and "microbial" refer to one or more of bacterial agent of the *Enterococcus* genus: *Enterococcus faecium, Enterococcus faecalis*, and *Enterococcus durans*.

In another embodiment, the terms "microbe" and "microbial" refer to one or more of bacterial agent of the *Listeria* genus: such as *Listeria monocytogenes*.

In another embodiment, the terms "microbe" and "microbial" refer to one or more anaerobic bacteria: *Clostridium perfringens, Actinomyces bovis, Propionibacterium acnes, Propionibacterium granulosum, Eubacterium, Peptococcus indolicus*, and *Peptostreptococcus anaerobius*.

In another embodiment, the terms "microbe" and "microbial" refer to one or more species of the *Mycoplasma* genus: such as *Mycoplasma bovis*.

In another embodiment, the terms "microbe" and "microbial" refer to one or more fungi of the *Malassezia* genus.

In another embodiment, the terms "treatment" or "treating" refers to the full or partial removal of the symptoms and signs of the condition. For example, in the treatment of mastitis, the treatment completely or partially removes the signs of mastitis. Preferably in the treatment of mastitis (such as in the treatment of bovines), the treatment reduces the somatic cell count below 280,000 cells/mL (≥a linear score of 5). Preferably the treatment reduces the somatic cell count below 280,000 cells/mL (≥a linear score of 5) by a percentage selected from the group consisting of: by 10%; by 20%; by 50%; by 80%; by 90% and by 95%.

Veterinary and pharmaceutical acceptable salts include salts which retain the biological effectiveness and properties of the compounds of the present disclosure and which are not biologically or otherwise undesirable. In many cases, the compounds disclosed herein are capable of forming acid and/or base salts by virtue of the presence of amino and/or carboxyl groups or groups similar thereto. Veterinary and pharmaceutical acceptable base addition salts can be prepared from, inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as by way of example only, alkyl amines, dialkyl amines, trialkyl amines, substituted alkyl amines, di(subsrituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amines, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Veterinary and pharmaceutical acceptable acid addition salts may be prepared from inorganic and organic acids. The inorganic acids that can be used include, by way of example only, hydrochloric acid, hydrobromic acid, sulfuric acid, nitric acid, phosphoric acid, and the like. The organic acids that can be used include, by way of example only, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The veterinary and pharmaceutical acceptable salts of the compounds useful in the present disclosure can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences. 17th ed., Mack Publishing Company, Easton, Pa. (1985), p. 1418, the disclosure of which is hereby incorporated by reference. Examples of such veterinary acceptable salts are the iodide, acetate, phenyl acetate, trifluoroacetate, acryl ate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, γ-hydroxybutyrate, β-hydroxybutyrate, butyne-1,4-dioate, hexyne-1,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, merhanesulfonate, naphthalene-1-sulfonate, naphthalene-2-sulfonate, p-toluenesulfonate, xylenesulfonate, tartarate, and the like.

It will be understood that the type of microbial infections for which the methods of the invention are intended to be used in treatment include infections in the mammary gland.

Intramammary infections may result in subclinical or clinical mastitis. Subclinical mastitis encompasses an infection without apparent signs of local inflammation or systemic involvement, and may result in transient episodes of abnormal milk or udder inflammation, which are usually asymptomatic. On persistence of infection the mastitis may be termed chronic. Detection may be carried out by examination of milk for somatic cell counts (such as, for example, neutrophils) using standard tests known in the art such as the California Mastitis Test or automated methods provided by dairy herd improvement organizations. Somatic cell counts generally indicate the presence of infection. As an example, cows with a somatic cell count of ≥280,000 cells/mL (≥a linear score of 5) have a >80% chance of being infected. The causative agent of the infection may be identified by bacterial culture of milk according to standard procedures known in the art.

Clinical mastitis encompasses an inflammatory response to infection causing visibly abnormal milk. Indications of inflammation may include changes in the udder (swelling, heat, pain, redness). Mild clinical cases include local signs only. Severe clinical cases include systemic involvement (fever, anorexia, shock) and rapid onset.

The compositions described herein may be formulated for intramammary administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

The compositions described herein may be in the form of a liquid formulation. The liquid formulation may comprise a solution that includes a therapeutic agent dissolved in a solvent. Generally, any solvent that has the desired effect may be used in which the therapeutic agent dissolves and which can be administered to a subject. Generally, any concentration of therapeutic agent that has the desired effect can be used. The formulation in some variations is a solution which is unsaturated, a saturated or a supersaturated solution. The solvent may be a pure solvent or may be a mixture of liquid solvent components. In some variations the solution formed is an in situ gelling formulation. Solvents and types of solutions that may be used are well known to those versed in such drug delivery technologies.

Also contemplated herein is the intramammary delivery of the compounds according to formulations known in the art. For instance, by intramammary infusion, comprising a polyether ionophore according to the invention, a vegetable oil, an alcohol-soluble fraction of natural lecithin phospholipid material for promoting dispersion of the oil in milk, the phospholipid being selected from the group consisting of phosphatidyl choline and phosphatidyl ethanolamine and mixtures thereof and present in an amount of at least 0.25% in said oil. Such compositions may provide rapid dispersion into milk and short milkout times. Alternatively, a polyether ionophore may be dispersed in an oil consisting of a mixture of triglycerides of palmitic and stearic acid together with polyoxyethylenated cetyl alcohol and stearyl alcohol, and held in an oily medium of mineral, vegetable, synthetic or mixed extraction. Such compositions may speed up release of the antimicrobial agent in the udder, enhancing its biological potential, and reducing milkout time. The intramammary formulation may be in the form of a paste composition comprising a polyether ionophore, fumed silica, a viscosity modifier and a hydrophilic carrier.

In one embodiment, the composition of the invention is formulated for intramammary delivery by formulating the polyether ionophore as a solid dispersion formulated within a intra-mammary formulation. In one further embodiment, the polyether ionophore is dispersed within a water soluble polymer to a form a solid dispersion. The solid dispersion is then formulated into an intramammary formulation by addition to an emollient triester. Viscosity can be adjusted by the addition of a silica-based composition to increase viscosity. In one example, the polyether ionophore is dispersed within polyvinylpyrrolidone K 30 to a form a solid dispsersion. The solid dispersion is then formulated into a intramammary formulation by addition to Crodamol GTCC (which is a fully saturated emollient triester) and the viscosity is adjusted by the addition of Aerosil R972 (Aerosil R972 is a fumed silica aftertreated with dimethyldichlorosilane). The intramammary composition is then dispensed into a syringe for application into the udder of the subject.

In a further aspect, the invention is an intramammary veterinary antimicrobial composition, comprising a therapeutically effective amount of a polyether ionophore formulated in a solid dispersion further formulated into a intramammary formulation. Preferably, the composition comprises a polyether ionophore dispersed within a water soluble polymer to form a solid dispsersion. The solid dispersion is formulated in an intramammary formulation by the addition to an emollient. Viscosity can be adjusted by the addition of a viscosity increasing or decreasing agent. More preferably, the composition comprises polyether ionophore, a water soluble polymer and an emollient. More preferably, the composition comprises polyether ionophore, a water soluble polymer, an emollient and viscosity forming agent. Even more preferably, the composition comprises a polyether ionophore, polyvinylpyrrolidone K 30, Crodamol GTCC and Aerosil R972.

In a preferred embodiment, the composition is a composition selected from the group consisting of:
  (1) 600 mg of the LP1369-PVPK30 solid dispersion (150 mg LP1369+450 mg PVPK30)+7% R972+Crodamol GTCC; and
  (2) 1200 mg of the LP1369-PVPK30 solid dispersion (300 mg LP1369+900 mg PVPK30)+7% R972+Crodamol GTCC.

In one aspect, the invention is a unit dosage form selected from the group consisting of:
  75 mg Group
  Each syringe contains 300 mg of the LP1369-PVPK30 solid dispersion (75 mg LP1369+225 mg PVPK30)+7% R972+Crodamol GTCC; final volume 5 mL.
  150 mg Group
  Each syringe contains 600 mg of the LP1369-PVPK30 solid dispersion (150 mg LP1369+450 mg PVPK30)+7% R972+Crodamol GTCC; final volume 5 mL.
  300 mg Group
  Each syringe contains 1200 mg of the LP1369-PVPK30 solid dispersion (300 mg LP1369+900 mg PVPK30)+7% R972+Crodamol GTCC; final volume 5 mL.
  600 mg group (300 mg×2)
  Each syringe contains 1200 mg of the LP1369-PVPK30 solid dispersion (300 mg LP1369+900 mg PVPK30)+7% R972+Crodamol GTCC; final volume 5 mL.

Intramammary delivery systems for mastitis treatment according to the invention include deliver via the intramammary route primarily for the delivery of compositions of the invention through the teat canal into the udder and close to the site of infection. The composition of the invention may comprise nanomodified active ingredients and be provided in the form of a veterinary acceptable, hydrophilic polymer-based hydrogel intramammary delivery system capable of in-situ gelling. Alternatively, the composition of the invention may be in the form of a mucoadhesive formulation, capable of adhering to the epithelium.

The compositions of the invention may alternatively be formulated using nanotechnology drug delivery techniques such as those known in the art. Nanotechnology-based drug delivery systems have the advantage of improving bioavailability, patient compliance and reducing side effects.

The formulation of the composition of the invention includes the preparation of nanoparticles in the form of nanosuspensions or nanoemulsions, based on compound solubility. Nanosuspensions are dispersions of nanosized drug particles prepared by bottom-up or top-down technology and stabilised with suitable excipients This approach may be applied to the polyether ionophores described herein where the polyether ioinophore has poor aqueous and lipid solubility in order to enhance saturation solubility and improve dissolution characteristics. Saturation solubility will be understood to be a compound-specific constant that depends on temperature, properties of the dissolution medium, and particle size (<1-2 μm).

The composition of the invention may be provided in the form of a nansuspension. For nanosuspensions, the increase in the surface area may lead to an increase in saturation solubility. Nanosuspensions are colloidal drug delivery systems, consisting of particles below 1 μm. Compositions of the invention may be in the form of nanosuspensions including nanocrystalline suspensions, solid lipid nanoparticles (SLNs), polymeric nanoparticles, nanocapsules, polymeric micelles and dendrimers. Nanosuspensions may be prepared using a top-down approach in that larger particles may be reduced to nanometre dimensions by a variety of techniques known in the art including wet-milling and high-pressure homogenisation. Alternatively, nanosuspensions may be prepared using a bottom-up technique in that controlled precipitation of particles may be carried out from solution.

The composition of the invention may be provided in the form of a nanoemulsion. Nanoemulsions are typically clear oil-in-water or water-in-oil biphasic systems, with a droplet size in the range of 100-500 nm, and with compounds of interest present in the hydrophobic phase. The preparation of nanoemulsions may improve the solubility of the polyether ionophores described herein, leading to better bioavailability. Nanosized suspensions may include agents for electrostatic or steric stabilisation such as polymers and surfactants. Compositions in the form of SLNs may comprise biodegradable lipids such as triglycerides, steroids, waxes and emulsifiers such as soybean lecithin, egg lecithin, and poloxamers. The preparation of a SLN preparation may involve dissolving/dispersing drug in melted lipid followed by hot or cold homogenisation. If hot homogenisation is used, the melted lipidic phase may be dispersed in an aqueous phase and an emulsion prepared. This may be solidified by cooling to achieve SLNs. If cold homogenisation is used, the lipidic phase may be solidified in liquid nitrogen and ground to micron size. The resulting powder may be subjected to high-pressure homogenisation in an aqueous surfactant solution.

Compositions of the invention may be in the form of a nanoemulsion. Polyether compounds as described herein may be dissolved in oils/liquid lipid and stabilised into an emulsion formulation. Nanoemulsions may be prepared using high- and low-energy droplet reduction techniques. High-energy methods may include high-pressure homogenisation, ultrasonication and microfluidisation. If the low-energy method is used, solvent diffusion and phase inversion will generate a spontaneous nanoemulsion. Lipids used in nanoemulsions may be selected from the group comprising triglycerides, soybean oil, safflower oil, and sesame oil. Other components such as emulsifiers, antioxidants, pH modifiers and preservatives may also be added.

For mastitis treatment, the intramammary route is primarily used for the delivery of drugs through the teat canal into the udder and close to the site of infection. The composition may be formulated to include nanomodified active ingredients. Accordingly, the composition may be in the form of a hydrophilic polymer-based hydrogel intramammary delivery system, capable of in-situ gelling. Alternatively, the composition may be in the form of a mucoadhesive formulation, capable of adhering to the epithelium. Other routes of administration include topical (such as epicutaneous) and enteral (such as oral).

The composition may be in the form of a controlled-release formulation may include a degradable or non-degradable polymer, hydrogel, organogel, or other physical construct that modifies the release of the polyether ionophore. It is understood that such formulations may include additional inactive ingredients that are added to provide desirable colour, stability, buffering capacity, dispersion, or other known desirable features. Such formulations may further include liposomes, such as emulsions, foams, micelles, insoluble monolayers, liquid crystals, phospholipid dispersions, lamellar layers and the like. Liposomes for use in the invention may be formed from standard vesicle-forming lipids, generally including neutral and negatively charged phospholipids and a sterol, such as cholesterol.

Throughout this specification, unless the context requires otherwise, the word "comprise" or variations such as "comprises" or "comprising", will be understood to imply the inclusion of a stated integer or group of integers but not the exclusion of any other integer or group of integers.

EXAMPLE 1

Antibacterial Activity Against Isolates of *Staphylococcus*

Specific

As is apparent from the preceding summary of the invention, the invention relates to methods of treatment of mastitis in subjects such as bovines, ovines, caprines, other ruminant species, camelids and equines, and also humans. As is also apparent from the preceding summary of the invention, the invention also relates to compositions used in such methods of treatment of mastitis.

It will be understood that systemic exposure of a subject to be treated according to the methods of treatment of the invention, or the compositions described herein, is to be minimised in order to minimise toxic effects of exposure to therapeutically effective amounts of polyether ionophores. It will be appreciated that the mammary/blood barrier functions as a physical barrier to absorption of therapeutically effective amounts of polyether ionophores, which compounds are understood to remain localised within the tissues and fluids of the mammary gland for localised antimicrobial activity and reduced toxic effects.

Materials and Methods

Bacterial Isolate Collection and Identification

Figures 1, 2:
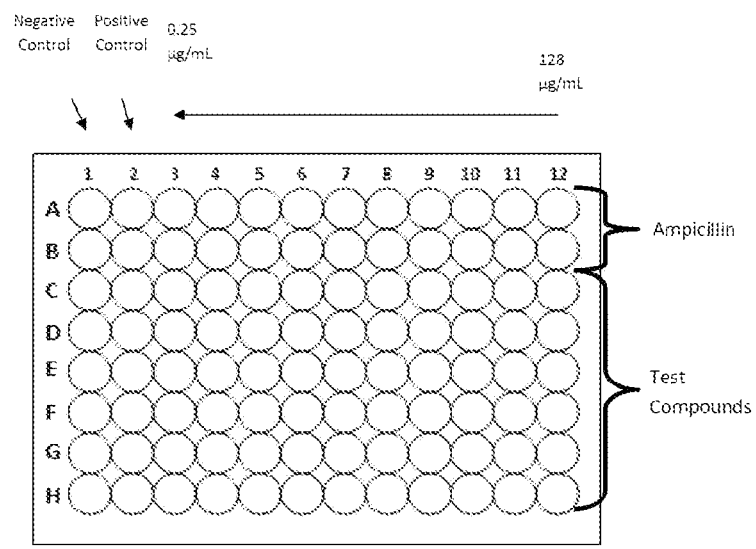
FIG. 1 is a table setting out the isolate collection and the vertebrate species source following biochemical identification of the *Staphylococcus* species including resistance profile according to Example 1.
FIG. 2 is a diagrammatic representation of the 96 well plate layout for the Minimum Inhibitory Concentration Testing according to Example 1.

Forty-two isolates of *Staphylococcus* of varying species and strain type were collected from isolate collections. Biochemical testing including coagulase, latex agglutination testing for protein A, Vogues-Proskauer tests and resistance to polymyxin B were used to identify the species of *Staphylococcus*. All isolates were also screened for resistance to various antimicrobials commonly used for the treatment of infections. This was performed using the disk diffusion method and resistance standards as outlined by the CLSI. The following antimicrobials were used: amoxicillin-clavulanic acid (30 µg), cephalothin (30 µg), clindamycin (2 µg), enrofloxacin (5 µg), erythromycin (15 µg), gentamicin (10 µg), imipenem (10 µg), oxacillin (1 µg), penicillin G (10 units), tetracycline (30 µg), 1:19 trimethoprim-sulfamethoxazole (25 µg) and vancomycin (30 µg). All strains resistant to oxacillin were found to also be resistant to amoxicillin-clavulanic acid, cephalothin and imipenem and these were determined to be methicillin-resistant strains. All isolate profiles are shown in FIG. 1.

Preparation of Antimicrobials

For each of the five test compounds, a 256 mg/mL stock solution was prepared by dissolving 2.56 grams of compound in 10 mL of dimethyl sulfoxide (DMSO). The resulting solution was then aliquoted into 500 µL volumes and stored at −80° C. until required. A 256 mg/mL stock solution of ampicillin was also prepared by dissolving 0.303 grams of ampicillin (Sigma A-0166) in 10 mL of DMSO. This solution was aliquoted and stored in the same manner as the five test compounds. When these compounds were required, a 256 µg/mL working solution was prepared by diluting 100 µL of stock solution (25.6 mg/mL) in 9.9 mL of cation adjusted Mueller Hinton Broth (CAMHB).

Minimum Inhibitory Concentration Assay

Minimum inhibitory concentration tests were performed according to CLSI Standards (CLSI 2012). 90 µL of one of the test compound solutions, or ampicillin, was added to the end column of a 96 well plate that contained 90 µL of CAMHB in each well. The solutions were then serially diluted across the row, leaving 2 columns for positive and negative controls (FIG. 2). A bacterial suspension was prepared by adding fresh colonies obtained from an overnight culture on Sheep Blood Agar (SBA) to a 9.1 g/L saline solution. This suspension was adjusted to a concentration of between $4 \times 10^8$ and $5 \times 10^8$ CFU/mL. Concentration of the suspension was determined by measuring optical density (OD) using a spectrophotometer at a wavelength of 600 nm where the correct concentration was determined to have an optical density of between 1.00 and 1.20. 1 mL of this suspension was added to 9 mL of saline before being added to all wells, excluding the negative control wells, in 10 μL volumes giving a final concentration of between $4 \times 10^5$ and $5 \times 10^5$ CFU/mL in each well. The tests were then incubated for 24 hours at 37° C. and then assessed both visually and using OD readings from a microplate reader at a wavelength of 600 nm. These tests were performed in duplicate but repeated if discrepancies were observed.

The minimum inhibitory concentration (MIC) was determined to be the lowest concentration of antibiotic that prevented growth of bacteria both visually and using OD readings. Direct statistical comparisons between the test compounds and ampicillin could not be performed in light of confidential information restrictions, such as restrictions on disclosure of information relating to the compound structure, such as molecular weight. Instead, MIC values were collated and used to determine the lowest concentration of each compound that was effective against 50% and 90% of isolates, referred to as the $MIC_{50}$ and $MIC_{90}$ respectively. These values as well as the range of MIC values were then used for direct comparisons between test compounds and for general comparisons with ampicillin.

Minimum Bactericidal Concentration Determination

Figure 3:
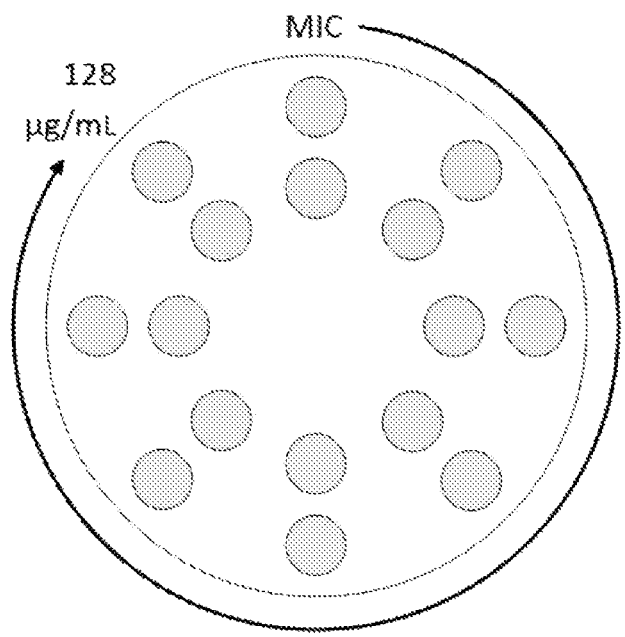
FIG. 3 is a diagrammatic representation of the Minimum Bactericidal Concentration test with shaded areas representing the placement of 10 μL volumes in duplicate and the direction of the arrow represents the increasing concentration as read clockwise around the plate according to Example 1.

Following determination of the MIC using the 96 well MIC plate, a variation of the drop plate method was used to determine minimum bactericidal concentration (MBC) for each of the test compounds. These were analysed using samples taken from the MIC plate following incubation. For each compound, a 10 μL drop of each concentration equal to or higher than the MIC was pipetted onto Sheep Blood Agar in a clockwise manner (FIG. 3). Each concentration was pipetted in duplicate with duplicates being pipetted on an inner ring of drops. The plates were incubated at 37° C. overnight and assessed the following day for growth. The MBC was defined as the concentration at which 99.9% of colonies were eradicated, which was visually assessed by a lack of growth on the agar where the drop was placed. Using these data, bactericidal activity could be suggested for some of the compounds. The MBC values for 50% and 90% of the isolates (MBC50 and MBC90) were calculated and assessed along with the MBC range in order to select compounds for further study.

Time-kill Kinetics Assay

Following assessment of MIC and MBC results, two compounds were chosen for analysis using microdilution time-kill assays, LP 1369 and LP 6315 and these were compared to ampicillin. Time-kill assays were performed according to the M26-A guidelines of the CLSI, with modifications. The test compounds and ampicillin were serial diluted in CAMHB across the rows of a 96 well plate and a bacterial suspension was prepared and added in the same manner as the MIC testing. The 96 well plates were then incubated at 37° C. for 48 hours being removed at specific time points and OD for the positive control wells as well as one, four and eight times the MIC of the compound specific to the strain being tested were assessed using a spectrophotometer at a wavelength of 600 nm. The time points assessed were 0, 1, 2, 4, 8, 12, 24 and 48 hours after the addition of the bacterial suspension to the wells. Each test compound was tested in triplicate while ampicillin was tested in duplicate and this test was independently repeated. The bacterial strains used for the microdilution assays were chosen based on bactericidal activity evident during MBC testing. One strain from each of the categories of *Staphylococcus* in the isolate collection (methicillin-sensitive, methicillin resistant and coagulase negative) were selected as well as the ATCC reference strain for comparison. These strains were strains MSS 1, MSS 11, MRSA 9 and the ATCC 49775 reference strain.

Due to the detection limit of the OD measurements, the time-kill assays were also performed in macrodilution. In 15 mL tubes, 9 mL volumes of the test compounds in CAMHB were prepared at one, four and eight times the MIC concentration and 9 mL volumes of ampicillin were prepared in CAMHB at one and four times the MIC. 1 mL of a 4 to $5 \times 10^6$ bacterial suspension (as prepared for MIC testing) was added to each of the tubes as well as a growth control tube containing only 9 mL of CAMHB. These tubes were incubated at 37° C. in an orbital shaker rotating at 100 rpm for 24 hours. At 0, 1, 4, 8, 12 and 24 hours after addition of the bacteria, 100 μL samples were removed from each tube and serial diluted in 9.1 g/L saline solution. The dilutions were then plated in duplicate onto plate count agar and incubated for 24 hours at 37° C. After incubation, viable counts were obtained from the number of colonies visible on the agar and these were used to calculate the number of CFU/mL at each time point. For the macrodilution time-kill analysis, only the ATCC 49775 reference strain and MRSA 9 were assessed in order to further investigate the antibacterial activity against methicillin-resistant strains. These macrodilution time-kill assays were independently repeated and bactericidal activity was defined as a ≥3 log decrease in the number of CFU/mL.

Eukaryotic Cell Toxicity Testing

Erythrocyte haemolysis was used in order to test the toxicity of all five compounds to eukaryotic cells. Blood samples were washed using 9.1 g/L saline solution and centrifuged at 2500 rpm for 10 minutes. This process was repeated until cellular debris and partially lysed cells were removed from solution. 2 mL of the remaining blood cells were suspended in 98 mL of 9.1 g/L saline solution to produce a 2% blood cell solution, which was dispensed in 90 μL volumes into the wells of a 96 well plate. The compound solutions as well as chloramphenicol were prepared from stock solution to a concentration of 256 μg/mL (as described above). Chloramphenicol was used as a negative control for erythrocyte lysis while a ready to use solution of amphotericin B was used as a positive control. 90 μL of the compounds and controls were added to the final well in different rows. These compounds were serially diluted across the row in order to test the different concentrations of antimicrobials. Wells containing only 2% blood solution were also used to assess variation between readings from different columns on the 96 well plates. These tests were incubated at 37° C. for one hour and then assessed for lysis both visually and using a microplate reader to measure optical density at 600 nm wavelengths. Each test was performed in duplicate and then repeated in quadruplicate in order to ensure accuracy.

Results

Figure 4:
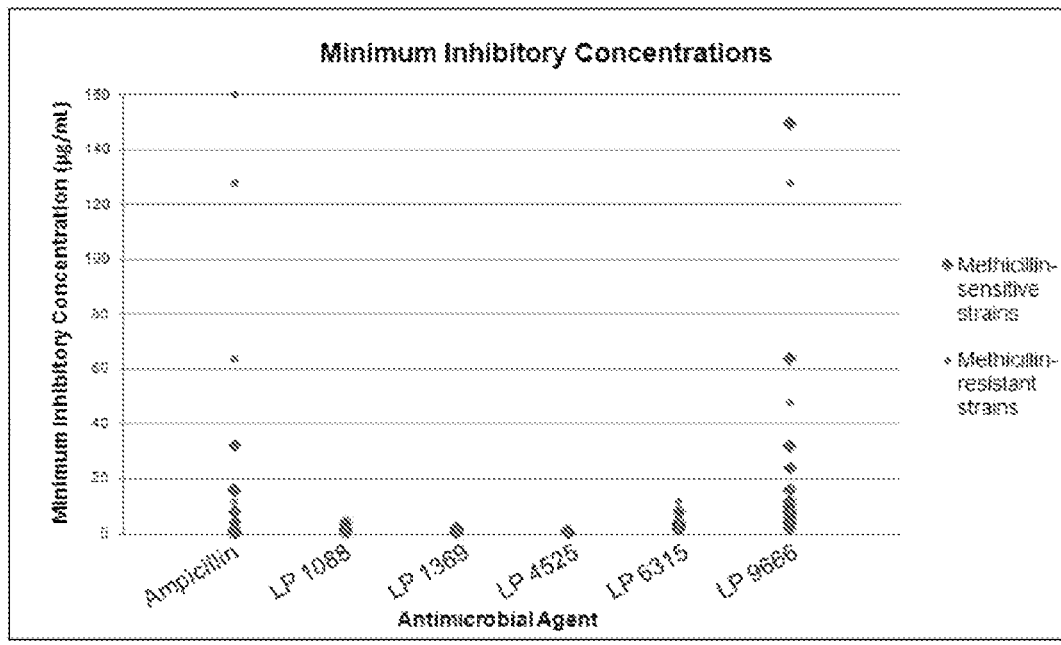
FIG. 4 shows a graph of the Minimum Inhibitory Concentrations for the individual isolates separated into methicillin-sensitive and methicillin-resistant strains; values shown as higher than 128 μg/mL represent strains where no MIC value was obtained within the range of concentrations tested (0.25-128 μg/mL) according to Example 1.

MIC testing results confirmed antibacterial activity for all test compounds in both methicillin sensitive and methicillin-resistant staphylococci. All test compounds had constantly low MIC values (below or equal to 16 µg/mL) for all strains with the exception of compound LP 9666 as shown in FIG. 4. MIC variation was demonstrated for compound LP 9666 as indicated by the high $MIC_{90}$ value and broad MIC range. While the range of MIC values was similar to that of ampicillin, there was no distinction between methicillin-resistant and methicillin-sensitive strains similar to that observed in the MIC values for ampicillin. The $MIC_{50}$, $MIC_{90}$ and MIC ranges for methicillin-sensitive *Staphylococcus* strains are shown in FIG. 5. The $MIC_{50}$ values for most of the test compounds except for LP 9666 were comparable to ampicillin while the $MIC_{90}$ values were considerably lower. This was reflected in the ranges for the test compounds across the strain collection which showed smaller ranges than ampicillin for all the test compounds except LP 9666. A similar trend was observed for methicillin-resistant isolates as shown in FIG. 6. Compounds LP 1088, 1369, 4525 and 6315 demonstrated $MIC_{50}$ and $MIC_{90}$ values considerably lower than ampicillin as well as narrow MIC ranges. However, while LP 9666 had higher MIC50 and MIC90 values than the other four test compounds, they were considerably lower than ampicillin for the methicillin-resistant strains.

All five test compounds exhibited bactericidal activity in high concentrations but compounds LP 1088, 1369, 4525 and 6315 also showed some bactericidal activity in lower concentrations. Compounds LP 1088 and 1369 exhibited bactericidal activity more consistently for methicillin-sensitive strains while compounds LP 4525 and 6315 exhibited bactericidal activity more consistently for methicillin-sensitive strains, as shown in FIG. 7.

Comparison of the $MBC_{50}$, $MBC_{90}$ and MBC ranges for the five test compounds for methicillin-sensitive and methicillin-resistant strains are shown in FIGS. 8 and 9, respectively. The $MBC_{50}$ and $MBC_{90}$ values showed that while some strain-dependent bactericidal activity was evident for the test compounds at low concentrations, most compounds were bacteriostatic for the majority of the strains tested. The greatest bactericidal activity was observed for compounds LP 1369 against methicillin-sensitive isolates and LP 6315 for methicillin-resistant isolates as these demonstrated the lowest $MBC_{50}$ values despite their similar MBC ranges.

In the microdilution time-kill assay, both compounds LP 1369 and LP 6315 prevented the growth of the ATCC reference strain over a 48 hour period compared to the growth control (FIG. 10). Some growth was observed after 48 hours for LP 6315 at the MIC but this was still significantly less than that of the growth control. Similar trends were observed for the kill kinetics assays performed for methicillin-sensitive strains MSS 1 and MSS 11 (FIGS. 11 and 12, respectively). Like the ATCC reference strain, all the compounds prevented the growth of bacteria to the levels of the growth control and, for most concentrations, prevented growth above the initial concentration. However, as with the ATCC strain, growth was observed at the MIC of LP 6315 but was observed 24 hours sooner and continued to increase for the final 24 hours. A similar trend was also observed in the MIC for ampicillin for MSS 11 but the increase in the number of bacteria in the final 24 hours was much steeper than that of the 1×MIC kill kinetics assay for LP 6315. For the time-kill assay for MRSA 9 (FIG. 13), an increase in the number of bacteria after 12 hours was evident for ampicillin and the resulting growth after 48 hours was comparable to the growth control. However, while an increase for 1×MIC of LP 6315 was evident after 24 hours, after 48 hours this growth was no longer observed.

Further time-kill assays in macrodilution showed a relatively constant decrease in the number of viable bacteria over the initial 24 hour period for both test compounds regardless of strain. FIGS. 14 and 15 show that the effect of compound LP 1369 on the number of bacteria was significant compared to the growth control for all the concentrations tested, but that this compound exhibited higher potency at four times the MIC than at eight times the concentration for both MRSA 9 and the ATCC 49775 reference strain. Total reduction in the number of bacteria was assessed, as shown in FIG. 16. As expected, ampicillin was shown to be bactericidal for both strains as the decrease in the number of viable bacteria was >3-$\log_{10}$ reduction while compound LP 1369 was found to be bacteriostatic for all concentrations as the decrease in the number of viable bacteria was <3-$\log_{10}$ reduction.

A similar trend to LP 1369 was observed in LP 6315. For the ATCC reference strain (FIG. 17), there was a constant decrease in the number of bacteria over the 24 hour period for all three concentrations of the test compound. For MRSA 9, shown in FIG. 18, all concentrations decreased the number of bacteria for the first 12 hours but an increase was observed between 12 and 24 hours for the MIC. When these reductions were quantified (FIG. 19), ampicillin was shown to be bactericidal as expected while most concentrations of LP 6315 were shown to be bacteriostatic. However, at four times the MIC, LP 6315 was observed to be bactericidal against MRSA as the decrease in colonies was >3-$\log_{10}$.

The optical density readings from the eukaryotic toxicity assays are shown below in FIG. 20. A decrease in optical density was interpreted as indicative of lysis of the red blood cells. While there was a decrease in optical density for all test compounds in concentrations of 32 µg/mL and higher, for all of the compounds except LP 1369, this decrease was not significant as the decrease was comparable to that of chloramphenicol and as no lysis of red blood cells was visually observed at these concentrations. While the level of lysis was not as high as amphotericin B for compound LP 1369, some lysis of cells was observed within the concentration range 32-128 µg/mL but this was most visually evident at 64 µg/mL.

EXAMPLE 2

Antibacterial Activity Against Skin Lesion Isolates

Isolates of *Staphylococcus pseudintermedius* were collected from skin lesions of various breeds of dogs. The presence of mec gene and the resistance profile were determined according to the materials and methods described in example 1.

FIG. 21 shows the results obtained for RT-PCR determination of mecA gene presence and resistance profile to various antibiotics. FIG. 22 shows the resistance profile of all the isolates obtained, while FIG. 23 shows the activity (individual results and MIC50, MIC90, MIC mode and MIC range) of ampicillin, LP1369, LP 4525 and LP6315 against the 23 isolates.

EXAMPLE 3

Antibacterial Activity Against Bovine Mastitis Isolates

Summary

Five antimicrobial agents, LP 1088, LP 1369, LP 4525, LP 6315 and LP 9666, were tested against 51 Australian bovine mastitis isolates, primarily pathogenic *S. aureus* species, *S. agalactiae* and *S. uberis*. LP4525 exhibited the lowest $MIC_{50}$ and $MIC_{90}$ (0.25 μg/ml and 1 μg/ml respectively). For LP1088, LP1369, LP6315 and LP9666, an $MIC_{90}$ of 2 μg/ml, 4 μg/ml, 4 μg/ml and 128 μg/ml was obtained, respectively. All tested antimicrobials elicited MBC values that suggested that these compounds are bacteriostatic against mastitis pathogens. LP4525 appears to be the most promising candidate intramammary antimicrobial agent to treat bovine mastitis cases resulting from infection with Gram-positive bacteria.

Materials and Methods

Bacterial Isolate Collection and Identification

Fifty-one dairy bovine mastitis isolates, encompassing a variety of bacterial species, were isolated from milk samples collected from dairy farms in rural South Australia by the University of Adelaide Ambulatory Clinic. Cellular morphology observed from Gram stains and catalase testing was used to differentiate *Staphylococcus, Streptococcus* and *Corynebacterium* species from Gram-negative species. Further biochemical testing including coagulase, Lancefield grouping, esculin hydrolysis and CAMP tests were used to identify the isolates to species level. Where biochemical test results were not definitive in identifying species, amplification and sequencing of the 16S ribosomal RNA gene was used to confirm the identity of the isolates.

Preparation of Antimicrobials

For each of the five test compounds, a 256 ring/ml stock solution was created by dissolving 2.56 grams of compound in 10 ml of dimethyl sulfoxide (DMSO). The resulting solution was then aliquoted into 500 μL volumes and stored at −80° C. A 256 mg/ml stock solution of ampicillin was also created by dissolving 0.303 grams of ampicillin (Sigma A-0166) in 10 ml of DMSO. This solution was aliquoted and stored in the same manner as the five test compounds. When these compounds were required, a 256 μg/ml working solution was created by diluting 100 μl of stock solution (25.6 mg/ml) in 9.9 ml of Cation-Adjusted Mueller Hinton Broth (CAMHB)

Minimum Inhibitory Concentration Assay

Minimum inhibitory concentration tests were performed in the manner outlined by the CLSI (CLSI 2012). Test compounds were dispensed into a 96-well microtitre tray containing 90 μl of CAMHB in 90 μl volumes and serial diluted to obtain a concentration gradient ranging from 128 μg/ml to 0.25 μg/ml (see FIG. 24). For *Streptococcus* species, CAMHB was replaced with a CAMHB supplement with 4% lysed-sheep blood (4% LSB:CAMHB). 4% LSB:CAMHB was prepared by mixing 5 ml sheep blood to 5 ml milliQ water, and repeated freezing at −20° C. and thawing, followed by centrifuged for 20 min at 7000 rpm. 7 ml of the supernatant was removed and added to 93 mL of CAMB.

Bacterial suspensions were prepared by emulsifying fresh colonies obtained from an overnight culture on Sheep Blood Agar (SBA) in 4 mls of 9.1 g/l physiological saline to an optical density read at 600 nm ($OD_{600nm}$) between 1.00 and 1.20. Standardised bacterial suspensions were diluted 1:10 in physiological saline and dispensed into all wells, excluding the negative control wells, in 10 μL volumes giving a final concentration of between $4 \times 10^5$ and $5 \times 10^5$ CFU/mL in each well. 96-well microtitre trays were incubated for 24 hours at 37° C. in 5% $CO_2$ and then assessed both visually and using OD readings from a microplate reader at a wavelength of 600 nm. These tests were performed in duplicate and repeated if discrepancies in MIC values were observed between replicates.

The minimum inhibitory concentration (MIC) was determined to be the lowest concentration of antibiotic that prevented growth of bacteria both visually and using OD readings. MIC values were collated and used to determine the lowest concentration of each compound effective against 50% and 90% of isolates, known as the $MIC_{50}$ and $MIC_{90}$ respectively. These values as well as the range of MIC values were then used for direct comparisons between test compounds and for general comparisons with ampicillin.

Minimum Bactericidal Concentration Determination

Following MIC determination, a variation of the drop plate method was used to determine the minimum bactericidal concentration (MBC) for each of the test compound. MBCs were determined by aliquotting a 10 82 L drop of each concentration from the microtitre plate onto SBA, which were then incubated for 16 hrs at 37° C. The MBC was defined as the concentration at which 99.9% of colonies were eradicated, which was visually assessed by a lack of growth on the agar where the drop was placed. The MBC values for 50% and 90% of the isolates ($MBC_{50}$ and $MBC_{90}$) were calculated and assessed along with the MBC range in order to select compounds for further study.

Results

Antibacterial activity against the bovine mastitis isolates was observed for all five of the test compounds, LP 1088, LP 1369, LP 4525, LP 6315 and LP 9666. LP4525 demonstrated the lowest MIC90 (1 μg/ml). The values for LP1088, LP1369 and LP6315 were one to two dilutions higher, whereas the value for LP9666 was several dilutions higher (FIG. 25). In contrast to the low $MIC_{9D}$ values obtained for 4 of the 5 compounds, the across the board high $MBC_{90}$ values indicate that all compounds appear for the most part to be bacteriostatic, although bactericidal activity at quite low concentrations above the MIC (2-8 μg/ml) was observed for some isolates. For the MICs and MBCs of individual isolates for all five compounds refer to FIG. 31 and FIG. 32.

When the MIC and MBC data was analysed according to the species of the isolates, it was evident that the $MIC_{50}$ and $MIC_{90}$ values were lower for *Streptococcus* species in comparison to the *Staphylococcus* species (FIGS. 26 to 30). However, the MIC ranges indicate that the differences between the two groups of pathogens are not significant. The MBC data was also highly variable within species, with some staphylococci and streptococci strains effectively killed at concentrations only just above the MIC (eg. for LP4525 and LP6315), but no significant difference was identified between species.

The preliminary results from this study suggest that all five compounds exhibit bacteriostatic activity with some compounds exhibiting strain-dependent bactericidal activity at high concentrations. Although all compounds exhibited some turbidity upon dilution in Cation Adjusted Mueller Hinton Broth, LP1088, LP1369, LP4525 and LP6315 all exhibited low MIC values. LP9666, however, had significantly higher $MIC_{90}$ values for each of the groups of mastitis pathogens, and this may be due to the large amount of precipitate formed when diluted in Cation Adjusted Mueller Hinton Broth. LP4525 had the most consistent MIC values for all isolates, and this is evidenced by the small MIC range. LP4525 also has a lower $MIC_{90}$ value compared to all compounds. We also found that one Gram-negative bacteria (isolate 2825 in the collection was susceptible to all five compounds.

EXAMPLE 4

Preparation of Intramammary Formulations for Example 5

Four formulations were prepared to formulate LP1369 for the animal studies in Example 5.

Composition of Formulations

Group 1: Vehicles only. Each syringe contains 7% Aerosil R972+Crodamol GTCC; final volume 5 mL Group 2: 'Microsized'. Each syringe contains 900 mg micrograde LP1369+7% Aerosil R972+Crodamol GTCC; final volume 5 mL Group 3: 'Nanosized'. Each syringe contains 900 mg nanograde LP1369+7% Aerosil R972+Crodamol GTCC; final volume 5 mL Group 4: 'PVP' (which is a solid dispersion). This is a mixture of PVP (polyvinylpyrrolidone K 30 (PVPK30, Sigma, 81420)) and LP1369. Each syringe contains 450 mg LP1369+1350 mg PVP+7% Aerosil R972+Crodamol GTCC; final volume 5 mL. Two syringes (450 mg/syringe× 2) were made for each quarter.

Preparation of Intra-mammary Formulations

Group 1: Vehicles only. Ten point five grams of Aerosil R972 was dissolved in 150 ml Crodamol GTCC (which is a fully saturated emollient triester, Chemsupply, CP209).

Group 2: Microsized LP1369 was made by passing LP1369 (>98% purity by HPLC, Bioaustralis fine chemicals, BIA-L1302) through a 75 µm sieve. Twenty seven (27) grams of LP1369 was suspended in Crodamol GTCC and 10.5 grams of R972 was added. The final volume of the suspension was made to 150 ml by Crodamol GTCC. The final concentration of LP1369 is 900 mg/5 mL.

Group 3: Nanosized compound was made by wet milling of LP1369 in Crodamol GTCC (80 mg/ml; 450 mg/5 ml) with <5 mm grinding balls for 30 min at 1000 rpm followed by homogenized for 30 min. Seven percent Aerosil R972 was added to maintain the viscosity. Two syringes (450 mg/syringe×2) were made for each quarter.

Group 4: PVP. Fifty four grams of PVP-LP1369 solid dispersion (13.5 grams of LP1369 and 40.5 grams of PVP) was suspended in Crodamol GTCC and 10.5 grams of Aerosil R972 was added. The final volume of the suspension was made to 150 ml by Crodamol GTCC. The final concentration of LP1369 is 450 mg/5 mL. Two syringes (450 mg/syringe×2) were made for each quarter.

EXAMPLE 5

A Pilot Study to Determine the Residue Depletion Profile of LP1369 in a Developmental Intra-mammary Antibiotic to be Used in Lactating Dairy Cattle Knowledge of the persistence of drug residues in milk following intramammary treatment is essential in order to determine the milk withholding period or length of time after the last treatment that milk must be discarded to reach a safe concentration. A study in cows treated with three LP1369 formulations was undertaken, monitoring the concentration in milk for 12 milkings (6 days) after administration. Data on concentrations of LP1369 in milk from 4 cows [micronized] ('Micronised'), 2 cows [nanosized] ('Nanosized') and 3 cows ('PVP'), treated at a single occasions at $1^{st}$, $2^{nd}$, and $12^{th}$ milkings after treatment, was provided by the analytical laboratory at the School of Pharmacy, University of South Australia, Adelaide, SA, Australia.

Data Analysis

Undetectable LP1369 concentrations in milk samples were set at 0.0001 mg/L. The milk concentration data was inspected using probability plots, and a log-normal distribution was found to be appropriate for all time-points. Therefore, the concentrations of LP1369 in whole milk were log-transformed before calculating means and standard deviations (weighted by the volume of milk produced by each animal) for each time point, using Microsoft Excel 2010.

Results

Cows Treated with Micronised Formulation

TABLE 1

| Milking information | Total milk volume (L) | Weighted Mean LP1369 concentration (mg/L) | Weighted Standard Deviation (mg/L) | Weighted UCL (upper confidence limit) (log scale)* |
|---|---|---|---|---|
| Milking 1 (12 hr) | 6.8 | 11.8533 | 11.949 | 1.0738 |
| Milking 2 (24 hr) | 14.3 | 2.6745 | 1.416 | 0.4276 |
| Milking 12 (144 hr) | 23.0 | 0.0001 | 0.000 | −4.0000 |

*weighted by milk yield

The UCLs on the log10 scale appear to decline linearly with time ($R^2=0.9980$). The fitted line suggests that the UCL will be below −1 (0.010 mg/L on log scale) at 65.3 hours after the last treatment when treated at a single occasion. Refer to FIG. 33.

Cows Treated with Nanosized Formulation

TABLE 2

| Milking information | Total milk volume (L) | Weighted Mean LP1369 concentration (mg/L) | Weighted SD (mg/L) | Weighted UCL (log scale)* |
|---|---|---|---|---|
| Milking 1 (12 hr) | 7.0 | 5.2121 | 3.994 | 0.7170 |
| Milking 2 (24 hr) | 9.4 | 0.4468 | 0.321 | −0.3499 |
| Milking 12 (144 hr) | 25.0 | 0.0001 | 0.000 | −4.0000 |

*weighted by milk yield

The UCLs on the log10 scale appear to decline linearly with time ($R^2=0.9856$). The fitted line suggests that the UCL will be below −1 (0.010 mg/L on log scale) at 61.1 hours after the last treatment when treated at single occasion. Refer to FIG. 34.

Cows Treated with PVP

TABLE 3

| Milking information | Total milk volume (L) | Weighted Mean LP1369 concentration (mg/L) | Weighted SD (mg/L) | Weighted UCL (log scale)* |
|---|---|---|---|---|
| Milking 1 (12 hr) | 36.1 | 1.5471 | 1.059 | 0.1895 |
| Milking 2 (24 hr) | 44.6 | 0.3748 | 0.196 | −0.4261 |
| Milking 12 (144 hr) | 56.7 | 0.0001 | 0.000 | −4.2283 | fixed as there was no population
*weighted by milk yield

The UCLs on the log10 scale appear to decline linearly with time ($R^2=0.9976$). The fitted line suggests that the UCL will be below −1 (0.010 mg/L on log scale) at 5.3 hours after the last treatment when treated at single occasion. Refer to FIG. 35.

Conclusion

A significant cost to the dairy farmer is associated with the need to discard milk from treated cows until milk concentrations reach a concentration deemed acceptable by regulatory agencies. The results of this study of LP1369 depletion have determined that a witholding period of 65.3, 61.1 and 5.3 hours, equivalent to 6, 6 and 1 milking(s) for micronised, nanosized and PVP formulations respectively, is expected to be necessary. The solid dispersion (PVP) formulation requires 5 fewer milk discardings.

EXAMPLE 6

Preparation of Intramammary Formulations for Example 7

Three Investigational Veterinary Products (IVP) were prepared to formulate LP1369 for intramammary application for the animal studies in Example 7.

TABLE 4

| | |
|---|---|
| 'IVP1' | Investigational Veterinary Product 1: LP1369 150 mg per syringe in solid dispersion |
| 'IVP2' | Investigational Veterinary Product 2: LP1369 300 mg per syringe in solid dispersion |
| 'IVP3' | Investigational Veterinary Product 2: LP1369 600 mg per syringe in solid dispersion |

Methods

The preparation of a intramammary formulation of LP1369 is a two step process. The first step is to prepare a solid dispersion of the compound, which is incorporated into an intra-mammary vehicle.

Preparation of Solid Dispersion

Eight grams of LP1369 (>98% purity by HPLC, Bioaustralis fine chemicals, BIA-L1302) and 24 grams of polyvinylpyrrolidone K 30 (PVPK30, Sigma, 81420) were added into a round bottom flask. Methanol (200 ml) was added together with stirring and sonication until LP1369 and PVPK30 were dissolved completely. Methanol was removed using a rotary evaporator at 45° C. under vacuum (~4-5 h). A solid dispersion formed around the wall of the round bottom flask and was collected, which was crushed out by a spatula and milled by a blender.

Preparation of Intra-mammary Formulations

Thirty grams of PVPK30-LP1369 (equivalent to 7.5 grams LP1369) or 60 grams of PVPK30-LP1369 (equivalent to 15 grams LP1369) solid dispersion was added into a flask. Crodamol GTCC (which is a fully saturated emollient triester, Chemsupply, CP209) was added to make a suspension (close to 250 mL, ~220 mL). Seventeen point five grams of Aerosil R972 (7% by weight) (Aerosil R972 is a fumed silica aftertreated with dimethyldichlorosilane, and was supplied by Evonik Australia Pty Ltd, catalogue number R972) was then added into the suspension to adjust the viscosity. The suspension was made to 250 mL and resulted in the following concentrations of LP1369; 150 mg/5 mL or 300 mg/5 mL.

For the 600 mg/syringe group, 120 grams of PVPK30-LP1369 (equivalent to 30 grams LP1369) solid dispersion was added into a flask. Crodamol GTCC was added to make a suspension (close to 250 mL, ~220 mL). Seventeen point five grams of Aerosil R972 (7% by weight) was then added into the suspension to adjust the viscosity. The suspension was made to 250 mL resulting in the concentration of LP1369 600 mg/5 mL. To improve flowability, the solid dispersion was diluted twice into 500 ml with another 17.5 grams of Aerosil R972 added to maintain the viscosity (final R972 7%). Two syringes (300 mg/syringe×2) were made for each quarter. Each syringe (Elm-Plastic, Düsseldorf, Germany: 8 ml Udder Injector Art. No. 808000) was filled up with 5 mL of suspensions and labelled.

Composition of Formulations 150 mg Group—IVP1

Each syringe contains 600 mg of the LP1369-PVPK30 solid dispersion (150 mg LP1369+450 mg PVPK30)+7% R972+Crodamol GTCC; final volume 5 mL 300 mg Group—IVP2

Each syringe contains 1200 mg of the LP1369-PVPK30 solid dispersion (300 mg LP1369+900 mg PVPK30)+7% R972+Crodamol GTCC; final volume 5 mL 600 mg Group (300 mg×2)—IVP3

Each syringe contains 1200 mg of the LP1369-PVPK30 solid dispersion (300 mg LP1369+900 mg PVPK30)+7% R972+Crodamol GTCC; final volume 5 mL

EXAMPLE 7

Efficacy of Investigational Veterinary Products Containing LP1369 in the Treatment of Induced *Streptococcus Uberis* Clinical Mastitis in Lactating Dairy Cows The objectives of the study were to estimate preliminary efficacy of two Investigational Veterinary Products (IVPs) containing LP1369 in the treatment of induced *Streptococcus uberis* clinical mastitis in lactating dairy cows. The specific objectives of this study were to:

(1) Test the preliminary efficacy of each IVP as a treatment of induced clinical mastitis in lactating cattle following experimental challenge via intramammary administration with a known strain of *S. uberis*.

(2) Compare the preliminary efficacy of the two IVPs in treating induced clinical mastitis in lactating cattle following experimental challenge via intramammary administration with a known strain of *S. uberis*.

(3) Compare the preliminary efficacy of the two IVPs with a commercial product in treating induced clinical mastitis in lactating cattle following experimental challenge via intramammary administration with a known strain of *S. uberis*.

The ultimate goal of the study was to provide data on the efficacy of the IVPs.

Clinical mastitis worldwide is the cause of significant losses to the dairy industry. The incidence of clinical mastitis in Australian and New Zealand dairy herds is estimated to be approximately 15% (McDougall, 1999, McDougall et al., 2007a, Petrovski et al., 2009). *Streptococcus uberis* has been reported as the predominant mastitis-causing organism in Australia (Shum et al., 2009); Petrovski 2013, unpublished) and New Zealand (Laven, 2008, McDougall, 1998, McDougall et al., 2007a, McDougall et al., 2007b). In order to test the efficacy in vivo of antibiotic treatments for mastitis, it is advantageous to treat infected cows. However, this can take a great deal of time in studies that enrol natural infections. Therefore, the use of an established mastitis challenge for lactating cows allows efficacy studies to be completed over a shorter time and with a smaller number of animals than if conducting studies with naturally occurring mastitis. The challenge model has been developed by this group previously and a single strain of *S. uberis* was selected as preferred challenge strain for further studies.

TABLE 5

| Test sites | |
| --- | --- |
| Test site for animal phase: | Dairy Research Centre<br>School of Animal and Veterinary Sciences<br>Roseworthy Campus<br>Roseworthy SA, 2371<br>Australia |
| Test site for microbiology: | Microbiology Laboratory<br>School of Animal and Veterinary Sciences<br>Roseworthy Campus<br>Roseworthy SA, 2371<br>Australia |

Experimental Design

Type and Design of the Study is the study was a non-randomised study to test the efficacy of the IVPs against clinical, induced mastitis challenge in lactating dairy cows. All cows had two contralateral quarters inoculated with a microbial suspension (i.e. Front left and Rear Right or Front Right and Rear Left). Challenged quarters were inoculated using an intramammary administration technique. Each inoculum had a volume of approximately 4 mL and contained approximately $10^6$ colony-forming units (cfu) per syringe of the known and well characterised strain of *S. uberis*.

Cows were milked using portable milking machines twice per day. Clinical examinations of the cow and each quarter were conducted every 12 hours, beginning at the first milking after challenge (hour 12), until hour 180. Prior to the milking before challenge, approximately 2 mL of milk was collected from each of the 4 quarters per cow, using an aseptic collection method for milk sampling testing. The appearance of milk secretions from each quarter was observed, using a dark-coloured plastic container or an old record for changes in consistency, and appearance. The presence of flecks or clots prompted further investigation. As signs of mastitis were detected, milk specimens were collected from the suspected-infected quarter using an aseptic collection method for milk sampling. Milk yield was recorded at each milking for each of the challenged and composite milk yield harvested from both unchallenged (e.g. FR and RL or FL and RR, together) quarters. At strategic time points, milk specimens were collected using a bucket milking system for the composite unchallenged quarters and quarter milking system for each challenged quarter every morning for somatic cell count, protein, fat and lactose percentage testing. Additionally, also at strategic time points, milk specimens were taken for HPLC and microbial inhibition residue testing, e.g. COPAN or Delvotest.

Before and after the completion of each milking, cows were observed for clinical signs associated with acute mastitis: depression, lameness and recumbency. The examination process includes visual observation and clinical examination of the animal, with focus concentrated on the udder. Individual udder quarters were inspected and palpated for clinical signs associated with mastitis, i.e. heat, swelling, redness, tenderness, and all observations were recorded.

Cows/quarters that showed signs consistent with clinical mastitis were immediately treated. As cows/quarters progressively demonstrated signs of mastitis they were treated with IVP1, IVP2, or with reference product (Noroclox LC, Norbrook). Treatment allocation of subsequent individual cows was via ongoing cycling of this pattern. If a second quarter in a single cow showed signs of mastitis at the same or subsequent milking/s, treatment was with the same IVP/Reference product as the first quarter treated for clinical mastitis in that particular cow. Therefore, the number of cows/quarters per group did vary.

TABLE 6

| | | Schedule of events |
| --- | --- | --- |
| Study Day | Hour relative to inoculation | Event |
| 0 | −1.0 | Aseptic milk sampling all cows |
| 0 | −0.5 | Milk all cows, observe treated cow, sample all cows |
| 0 | 0 | CHALLENGE ALL COWS |
| 0 | 0 to 2 | Observe all cows |
| 1 | 12 | Clinical observation, milk all cows, collection of specimens and treatment as required |
| 2 | 24 | Clinical observation, milk all cows, collection of specimens and treatment as required |
| 2 | 36 | Clinical observation, milk all cows, collection of specimens and treatment as required |
| 3 | 48 | Clinical observation, milk all cows, collection of specimens and treatment as required |
| 3 | 60 | Clinical observation, milk all cows, collection of specimens and treatment as required |
| 4 | 72 | Clinical observation, milk all cows, collection of specimens and treatment as required |
| 4 | 84 | Clinical observation, milk all cows, collection of specimens and treatment as required |
| 5 | 96 | Clinical observation, milk all cows, collection of specimens and treatment as required |
| 5 | 108 | Clinical observation, milk all cows, collection of specimens and treatment as required |
| 6 | 120 | Clinical observation, milk all cows, collection of specimens and treatment as required |

TABLE 6-continued

Schedule of events

| Study Day | Hour relative to inoculation | Event |
|---|---|---|
| 6 | 132 | Clinical observation, milk all cows, collection of specimens and treatment as required |
| 7 | 144 | Clinical observation, milk all cows, collection of specimens and treatment as required |
| 7 | 156 | Clinical observation, milk all cows, collection of specimens and treatment as required |
| 8 | 168 | Clinical observation, milk all cows, collection of specimens and treatment as required |
| 8 | 180 | Clinical observation, milk all cows, collection of specimens and treatment as required |

Materials and methods

Animals
Animal Details
Species: Bovine
Age: 2-10 years old.
Breed: Common dairy cattle (Holstein Friesian)
Type: Lactating dairy cattle
Body weight: Not applicable
Number and sex: 14 female
Identification: Cows were identified by permanent, uniquely numbered single ear tags at the farm of origin. Additionally, each cow was spray-marked on its hind leg just below the pubic bone with a unique study identification number (e.g. 1, 2, 3 . . . 14) using cans of tailpaint spray of various colours. The same unique study identification number was written on a single, colour-coordinated, plastic leg band that was applied to each cow on a hind pastern.
Source: The animals will be obtained from a commercial dairy herd.
Inclusion Criteria
Healthy cows (on clinical observation 3-4 days before purchase)
Four functional quarters (before purchase)
Known somatic cell history (no SCC above 250,000 cells/mL in the last 12 months)
Cows not treated with antimicrobials within 14 days prior to study commencement
Post-inclusion Removal (Withdrawal)
It was not expected that cows would need to be removed from the study due to its short duration. However, cows that were deemed unsuitable for continuation in the study were removed following approval from the Principal Investigator. The reason for any removal was fully documented and justified in the raw data and SR. Any cow that was removed from the study receives appropriate veterinary care. A single cow was removed due to accidental trauma to a rear leg.

Animal Maintenance and Husbandry

Cows were maintained at the test site animal phase for the duration of the study. Cows were acclimatised to the facility for a minimum 7 days before study commencement. Cows were managed under Australian feedlot/housed conditions that are consistent with good farming practice recommendations. Cows were maintained on the total mixed ration and grain-based concentrate used on the farm of origin. Mains water was available for drinking ad libitum from a clean, self-replenishing trough.

Group Allocation and Randomisation

All cows that meet the inclusion criteria were enrolled in the study. The quarter to be challenged was alternated between cows as presented in Table 7 based on the order of cows in the milking shed. The final allocation to challenge was reported in the SR.

TABLE 7

Treatment regime for each cow

| Cow order in the milking shed | Front Left | Front Right | Rear Left | Rear Right |
|---|---|---|---|---|
| 1 | Challenged | Unchallenged | Unchallenged | Challenged |
| 2 | Unchallenged | Challenged | Challenged | Unchallenged |
| 3 | Challenged | Unchallenged | Unchallenged | Challenged |
| 4 | Unchallenged | Challenged | Challenged | Unchallenged |
| 5 | Challenged | Unchallenged | Unchallenged | Challenged |
| 6 | Unchallenged | Challenged | Challenged | Unchallenged |
| 7 | Challenged | Unchallenged | Unchallenged | Challenged |
| 8 | Unchallenged | Challenged | Challenged | Unchallenged |
| 9 | Challenged | Unchallenged | Unchallenged | Challenged |
| 10 | Unchallenged | Challenged | Challenged | Unchallenged |
| 11 | Challenged | Unchallenged | Unchallenged | Challenged |
| 12 | Unchallenged | Challenged | Challenged | Unchallenged |
| 13 | Challenged | Unchallenged | Unchallenged | Challenged |
| 14 | Unchallenged | Challenged | Challenged | Unchallenged |

Challenge
Challenge Strain

The *S. uberis* strains used for the challenge was obtained from the library of strains at SAVS Microbiology Laboratory, The University of Adelaide. The selected strain was one that was well characterised and known by prior study to successfully cause clinical mastitis in the period of 36-120 hours after challenge. The strain was phenotypically identified as *S. uberis*, by means of biochemical tests according to standard microbiological methods.

Challenge Suspension

The preparation of the challenge suspension of the selected *S. uberis* strains was carried out at the Microbiology Laboratory at SAVS, The University of Adelaide. The procedure for preparation of the challenge suspension followed the laboratory's standard operating procedure.

Experimental Infection

All cows were exposed in two contra-lateral quarters (refer to Table 7) to the challenge suspensions as soon as possible after milking had finished, but not longer than 0.5 hours post-milking. Before inoculation, the teat ends of all four quarters were thoroughly cleaned using dry paper towels and alcohol-soaked cotton swabs or appropriate teat wipes. The challenge inoculum was inoculated via the intramammary route. The entire contents of one syringe was administered to each of the pre-determined, challenged quarters. After administration of the challenge suspension, the quarter was thoroughly massaged to assist dispersion of the suspension in the udder.

Treatment Regime

An accredited veterinarian or appropriately trained personnel undertook all treatments. The Principal Investigator maintained detailed records of the training session of the study personnel, test products used, and dosages administered during the study.

The cows were treated by the intramammary route as per treatment schedule. Treatments were recorded in the "Treatment Record" form.

IVP Products Administration and Frequency

Each individual cow was treated with the recommended dose of one intramammary syringe per quarter on each occasion, on six consecutive instances. For cows/quarters treated with IVP1 and IVP2, each infected quarter was treated immediately following each milking on 6 consecutive occasions, e.g. every 12 hours. The intramammary treatment was administered according to documented standard operating procedures.

Reference Product Administration and Frequency

Each individual cow was treated with the recommended dose of one intramammary syringe per quarter on each occasion, on three instances. For cows/quarters treated with the reference product, each quarter was treated immediately following milking on 3 occasions, 24-hours apart. The intramammary treatment was administered according to documented standard operating procedures.

Concomitant Treatments

The use of any other treatment related to the test product was prohibited during the study. All other treatments should be used only to avoid unnecessary suffering of the animals and need to be justified. In any case, the Principal Investigator must be informed and approve any treatment.

Observations/Measurements/Collection of Specimens

Animal Examination

A Veterinarian examined each cow prior to treatment. The examinations included general observations (specifically body conformation, posture and demeanour), taking rectal temperature and palpation of each quarter of the udders.

Body weights were not be taken during this study.

The cows were observed at least two times daily for any signs of ill health by study personnel throughout the study. Observations were recorded on a Daily Log form. In the case of adverse events (AEs) the Principal Investigator and, where necessary, a veterinarian were notified immediately. All events were recorded.

Each cow was observed for signs consistent with clinical mastitis at each milking starting with Study Day 0 Hour 0 until Study Day 8 Hour 180.

Any cows showing greater than mild signs of discomfort (higher than score 3 as described in documented standard operating procedures) were treated with anti-inflammatory pain relief (ketoprofen) at the recommended dose by the manufacturer.

The results of all observations, whether or not abnormalities are present, were recorded on the observation form.

Clinical Examination Pre-milking and Aseptic Quarter-level Milk Specimens Collection from Cows Cows were milked and clinical examinations were conducted every 12 hours beginning immediately prior to challenge inoculation (Study Day 0 Hour 0) until Study Day 8 Hour 180. At each milking, prior to quarter milking for challenged and bucket milking for unchallenged quarters, the appearance of the milk secretions was observed, using a dark-coloured plastic container, for changes consistent with mastitis including changes in consistency, appearance and/or presence of flecks or clots. As signs indicative of mastitis occurred, additional milk specimens were collected using an aseptic technique, in accordance with documented standard operating procedures.

All aseptic milk specimens were collected in duplicate.

Observation of the Milk Appearance

Once the initial observations and aseptic specimens had been completed, the appearance of the milk secretions was observed, using a dark-coloured plastic container or an old record, for changes in consistency, appearance and presence of flecks or clots. Milk appearance was assessed based on criteria described in documented standard operating procedures.

Milking

After observations of the milk appearance, cows were milked using portable milking machines. Challenged quarters were milked every 12 hours beginning immediately prior to challenge inoculation (Study Day 0 Hour 0) until Study Day 8 Hour 180 using quarter milkers. Unchallenged quarters of each cow were milked every 12 hours beginning immediately prior to challenge inoculation (Study Day 0 Hour 0) until Study Day 8 Hour 180 using bucket milking.

Milk Yields

Milk yields for challenged and unchallenged quarters were recorded at each milking separately for challenged and composite for unchallenged (e.g. FR and RL or FL and RR, together as a data point for unchallenged quarters) quarters.

Challenged- and Unchallenged- Quarters-level Milk Specimens Collection

Specimens were collected from the pooled milk from the two applicable unchallenged quarters as harvested by bucket milking or at individual quarter for challenged quarters as harvested into the quarter milkers. These specimens were representative of the milk harvested from each cow/quarter/combination of quarters according to documented standard operating procedures and were used as fresh milk analysis specimens. Such collected specimens were used for somatic cell count, protein, fat and lactose percentage testing.

After Milking Examination of the Udders/Cows

After the completion of milking, cows were observed for clinical signs associated with acute mastitis: depression, lameness, recumbency and by checking the rectal temperature. The examination process includee visual observation and clinical examination of the animal concentrated on the udder. However, upon suspicion of an animal being ill, a detailed clinical examination by a registered veterinarian, aiming to diagnose the clinical condition, was undertaken. This may have included a blood sample for appropriate tests (e.g. haematology, biochemistry) if considered necessary.

Udders and individual quarters were inspected and palpated for clinical signs associated with mastitis, i.e. heat, swelling, redness, tenderness. The description of the udder palpation scoring system were according to documented standard operating procedures.

Treatment of Quarters/Cows Diagnosed with Mastitis

As signs of mastitis (changes in milk, hot, swollen and painful udder or palpation score of ≥3 according to documented standard operating procedures) were detected, milk specimens were collected from the suspected-infected quarter using an aseptic collection of milk specimens according to documented standard operating procedures. Quarters diagnosed with mastitis were treated with IVP or reference product. The first cow/quarter showing signs of mastitis was treated with IVP1, thence progressively IVP2 and the reference product. This cycle was repeated as applicable for subsequent infected cows. If a second quarter in a single cow showed signs of mastitis at the same or consecutive milking/s, that cow was treated with the same IVP/reference product in the second quarter as the first. Therefore, the number of cows/quarters per group may vary.

If more than two quarters per cow became infected, an injectable product was used (i.e. Mamazyn) as per label recommendation (e.g. 5 g once a day on three occasions). For cows presenting with signs of acute generalised mastitis, a systemic antibiotic treatment was immediately commenced and, as required, supportive treatment (e.g. non-steroidal anti-inflammatory-ketoprofen) was given. The treatment decision was made by a registered veterinarian in consultation with the Principal Investigator. Quarters continued to be observed at each milking and treated as appropriate.

Assessment of Efficacy

Definition of Efficacy

The product was deemed efficacious if 50% of treated quarters achieved clinical cure within 5 days from initiation of treatment.

Measurement of Efficacy

Clinical Cure

Clinical cure was determined through clinical examination of the cows, udder palpations and observations of the appearance of milk. Clinical cure was defined as:

(1) Palpation score of ≤3 according to documented standard operating procedures, and/or (2) Milk score of ≤3 according to documented standard operating procedures, and/or (3) Udder returns to normal temperature, becomes non-swollen, non-painful on touch or redness has disappeared, and/or (4) The general health of the cow is scored ≤3 according to documented standard operating procedures.

Microbial Cure

The clinical cure was also be determined through microbial culture of aseptic milk samples collected prior to treatment and minimum 7 days after last treatment at quarter level. Microbial cure was defined as:

(1) Isolation of one or two colony types before treatment followed by no growth after treatment.

(2) Isolation of one or two colony types pre-treatment followed by isolation of different colony type/s after treatment.

The efficacy of the IVP/reference product was determined as:

(1) Percentage of quarters with clinical mastitis that achieved clinical cure from the total number of quarters treated with a particular IVP/reference product.

(2) Percentage of quarters with clinical mastitis that achieved microbial cure from the total number of quarters treated with a particular IVP/reference product.

References used for these methods (1) Laven, R. 2008. Clinical forum: choosing mastitis treatment in the lactating cow: selling or science? UK Vet: Livestock 13(4):29-36.

(2) McDougall, S. 1998. Efficacy of two antibiotic treatments in curing clinical and subclinical mastitis in lactating dairy cows. N. Z. Vet. J. 46(6):226-232.

(3) McDougall, S. 1999. Prevalence of clinical mastitis in 38 Waikato dairy herds in early lactation. N. Z. Vet. J. 47(4):143-149.

(4) McDougall, S., K. E. Agnew, R. Cursons, X. X. Hou, and C. R. Compton. 2007a. Parenteral treatment of clinical mastitis with tylosin base or penethamate hydriodide in dairy cattle. J. Dairy Sci. 90(2):779-789.

(5) McDougall, S., D. G. Arthur, M. A. Bryan, J. J. Vermunt, and A. M. Weir. 2007b. Clinical and bacteriological response to treatment of clinical mastitis with one of three intramammary antibiotics. N. Z. Vet. J. 55(4):161-170.

(6) Petrovski, K., C. Heuer, T. Parkinson, and N. Williamson. 2009. The incidence and aetiology of clinical bovine mastitis on 14 farms in Northland, New Zealand. N. Z. Vet. J. 57(2):109-115.

(7) Shum, L. W. C., C. S. McConnel, A. A. Gunn, and J. K. House. 2009. Environmental mastitis in intensive high-producing dairy herds in New South Wales. Aust. Vet. J. 87(12):469-475.

Results

TABLE 8

| Abbreviations | |
|---|---|
| IVP1 | Investigational Veterinary Product 1: LP1369 150 mg per syringe in solid dispersion |
| IVP2 | Investigational Veterinary Product 2: LP1369 300 mg per syringe in solid dispersion |
| REF | Reference product: Norodox containing 200 mg cloxacillin benzathine per syringe |
| UUC | Untreated Unchallenged Control: untreated and unchallenged control quarters in each treated cow |

Milk appearance before milking

TABLE 9

Average milk appearance at strip-milk test before milking score and differences per treatment group

| Treatment group | Average appearance score | SE | Difference to |
|---|---|---|---|
| IVP1 | 0.76 | 0.09 | UUC |
| IVP2 | 0.76 | 0.10 | UUC |
| REF | 0.79 | 0.07 | IVP1, IVP2, UUC |
| UUC | −0.13 | 0.06 | IVP1, IVP2, REF |

Palpation scores after milking

TABLE 10

Average palpation scores of quarters immediately after milking and differences per treatment

| Treatment group | Average palpation score | SE | Difference to |
|---|---|---|---|
| IVP1 | 1.67 | 0.11 | REF, UUC |
| IVP2 | 1.62 | 0.11 | REF, UUC |
| REF | 1 | 0.08 | IVP1, IVP2, UUC |
| UUC | 0.51 | 0.07 | IVP1, IVP2, REF |

Milk yields

TABLE 11

Average milk yields and differences per treatment group

| Treatment group | Average milk yield (L/quarter/milking) | SE | Difference to |
|---|---|---|---|
| IVP1 | 1.69 | 0.12 | IVP2, UUC |
| IVP2 | 1.38 | 0.12 | IVP1, UUC |
| REF | 1.46 | 0.09 | UUC |
| UUC | 2.28 | 0.09 | IVP1, IVP2, REF |

TABLE 12

Summary of Clinical Cures and Failures

Clinical cure

Clinical cure is determined by clinical examinations of each cow, udder palpation and observations of the appearance of the milk.
Clinical cure is defined as:

1. Palpation score of ≤3, and/or
2. Milk score of ≤3, and/or
3. Udder returns to normal temperature, becomes non-swollen, non-painful on touch or redness has disappeared, and/or
4. The general health of the cow is scored ≤3

| TREATMENT | COW | QUARTER | PALPATION SCORE | MILK SCORE | UDDER | GENERAL HEALTH SCORE | STATUS |
|---|---|---|---|---|---|---|---|
| IVP1 | 1 | F | ≤3 | ≤3 | Normal | ≤3 | Cure |
| IVP1 | 1 | H | ≤3 | ≤3 | Normal | ≤3 | Cure |
| IVP1 | 2 | F | ≤3 | ≤3 | Normal | ≤3 | Cure |
| IVP1 | 2 | H | ≤3 | ≤3 | Normal | ≤3 | Cure |
| IVP1 | 3 | F | ≤3 | ≤3 | Normal | ≤3 | Cure |
| IVP1 | 3 | H | ≤3 | ≤3 | Normal | ≤3 | Cure |
| IVP2 | 4 | F | ≤3 | ≤3 | Normal | ≤3 | Cure |
| IVP2 | 4 | H | ≤3 | ≤3 | Normal | ≤3 | Cure |
| IVP2 | 5 | F | ≤3 | ≤3 | Normal | ≤3 | Cure |
| IVP2 | 5 | H | ≤3 | ≤3 | Normal | ≤3 | Cure |
| IVP2 | 6 | F | >3 | >3 | Abnormal | >3 | FAIL |
| IVP2 | 6 | H | >3 | >3 | Abnormal | >3 | FAIL |
| Reference | 7 | F | ≤3 | ≤3 | Normal | ≤3 | Cure |
| Reference | 7 | H | ≤3 | ≤3 | Normal | ≤3 | Cure |
| Reference | 8 | F | ≤3 | ≤3 | Normal | ≤3 | Cure |
| Reference | 8 | H | ≤3 | ≤3 | Normal | ≤3 | Cure |
| Reference | 9 | F | >3 | >3 | Abnormal | >3 | FAIL |
| Reference | 9 | H | >3 | >3 | Abnormal | >3 | FAIL |

The *Streptococcus uberis* challenge in the present study provided sufficient bacterial challenge to overwhelm the commercially available reference product (Noroclox) with only 2 of 3 cows cured. Noroclox is usually expected to be fully effective under conditions of practical field challenge indicating that the challenge in this study was extreme. Despite the significant bacterial challenge, IVP1 (150 mg LP1369) and IVP2 (300 mg LP1369) performed as well as or superior to the reference product, substantiating the high level of activity provided by both formulations against this important and common cause of bovine mastitis. Refer to Table 12.

EXAMPLE 8

Determination of the Microbial Cure Effectiveness of the Treatments Presented in Example 7.

While close inspection of the health of the cow, the appearance of the udder (especially for signs of inflammation—temperature, swelling, pain, redness) and the appearance of the milk can indicate whether or not a clinical cure of mastitis has been achieved, an alternative test is that the treatment demonstrates a microbiological cure. Under appropriate conditions bacteria can invade the udder and cause mastitis. If the mastitis causing organisms are not removed from the infected udder by treatment, then they can remain as a potential sure of reinfection not only for the infected cow but also for other cows in the herd with close contact. Furthermore, the presence of bacteria in milk is not considered desirable from a milk quality and food safety perspective, even though bacteria are likely to be killed during pasteurisation. Therefore, it is highly beneficial to assess the ability of an intramammary treatment to bring about microbiological cure.

Microbiological cure of mastitis is determined through microbial culture of aseptic milk samples collected prior to treatment and a minimum of 7 days after the last treatment at quarter level. Microbial cure is defined as either (i) isolation of one or two colony types before treatment followed by no growth after treatment or (ii) isolation of one or two colony types pre-treatment followed by isolation of different colony type/s after treatment. The efficacy of the IVP/reference product is determined as the percentage of all quarters with clinical mastitis treated with a particular IVP/reference product that achieved microbiological cure.

Materials and Methods

Microbial culture results were generated from milk samples collected at pre-infection, post-infection and post-treatment. Cells containing the digit zero were found to be culture negative. Where a sample was obtained, information on organism identity and number of organisms present (CFU/ml) is presented or the sample is identified as contaminated (see FIG. 36). Remaining cells in the figure indicate the reason a sample was not collected for assessment.

Results

The results are presented in FIG. 36. The reference product (Noroclox) achieved a microbiological cure in 5 of 8 (62.5%) challenged quarters. IVP2 (300 mg LP1369) achieved a microbiological cure in 4 of 6 (66.7%) challenged quarters. IVP1 (150 mg LP1369) achieved a full or partial microbiological cure in 4 of 6 (66.7%) challenged quarters. In this induced *Streptococcus uberis*-mastitis model, the results show, together with the results presented in Example 7, IVP 1 and IVP2 provided high levels of clinical and microbial cure. These results show effective treatment of mastitis.

EXAMPLE 9

Determining the Residue Depletion Profile of LP1369 in the Treatment of Induced *Streptococcus uberis* Clinical Mastitis in Lactating Dairy Cows (Example 7)

Data on concentrations of LP1369 in milk from 6 quarters for IVP 1 and IVP 2 treated at 6 occasions (6 consecutive milkings) after treatment was provided by the analytical laboratory at the School of Pharmacy, University of South Australia, Adelaide, SA, Australia. The limit of quantification (LoQ) of the method for LP1369 in milk was 0.088 mg/L. The Maximum Residues level (MRL) for LP1369 is 0.010 mg/kg according to the APVMA, December 2013, *Agricultural and Veterinary Chemicals Code Instrument No. 4* (*MRL Standard*) 2012.

Data Analysis

In milk samples where LP1369 levels were below the LoQ, LP1369 concentration was set to 0.0001 mg/L.

The milk concentration data was inspected using probability plots, and a log-normal distribution was found to be appropriate for all time-points. Therefore, the concentrations of LP1369 in whole milk were log-transformed before calculating means and standard deviations (weighted by the volume of milk produced by each animal) for each time point, using Microsoft Excel 2010.

The determination of the depletion of any substance from milk is affected by the size of the population studied. As the number of sampled cows in this study was small, the g' factor (a factor that provides a 99% confidence interval so that results are likely to be representative of the population) was applied to the analysis. The possibility of dispersed data was minimised by fixing the g' factor for a population of 20 animals.

The following assumptions were made. The concentration of the active in milk at milking 1 (time 12 hr) was representative of the average concentrations achieved at milkings after the first, second and the last treatment. Further, the milk volume at milking 1 (time 12 hr) was representative of the average milk volume harvested at milkings after the first, second and the last treatment.

Results

TABLE 13

Quarters treated with IVP 1 (150 mg active per syringe)

| Milking information | Total milk volume (L) | Weighted Mean LP1369 concentration (mg/L) | Weighted SD (mg/L) | Weighted UCL (log scale)* |
|---|---|---|---|---|
| Milking 1 (12 hr) | 6.28 | 26.1619 | 11.3811 | 2.2594 |
| Milking 2 (24 hr) | 9.75 | 1.7359 | 3.0289 | 1.3336 |
| Milking 4 (48 hr) | 7.00 | 0.8422 | 4.3938 | 1.1010 |
| Milking 6 (72 hr) | 9.50 | 0.1153 | 0.2720 | 0.2103 |

*weighted by milk yield

As shown in FIG. 37, the UCLs on the log10 scale appear to decline linearly with time ($R^2$=0.9113). The fitted line suggests that the UCL will be below −1 (0.010 mg/L on log scale) at 112.7 hours after the last treatment when treated on 6 consecutive milkings. The extremely high UCL and long residue depletion is most likely due to aberrant result of 1/6 quarters (cow/quarter id 9 FR) being highly positive at 4th milking after the last treatment.

TABLE 14

Quarters treated (2 per cow) with IVP 2 (300 mg active per syringe)

| Milking information | Total milk volume (L) | Weighted Mean LP1369 concentration (mg/L) | Weighted SD (mg/L) | Weighted UCL (log scale)* |
|---|---|---|---|---|
| Milking 1 (12 hr) | 4.94 | 117.1022 | 102.3072 | 2.8663 |
| Milking 2 (24 hr) | 5.40 | 1.5246 | 4.7322 | 1.1895 |
| Milking 4 (48 hr) | 5.65 | 0.1376 | 0.2538 | 0.0980 |
| Milking 6 (72 hr) | 5.75 | 0.0001 | 0.0000 | −3.3010 |

*weighted by milk yield

As shown in FIG. 38, the UCLs on the log10 scale appear to decline linearly with time ($R^2$=0.9558). The fitted line suggests that the UCL will be below −1 (0.010 mg/L on log scale) at 51.7 hours after the last treatment when treated on 6 consecutive milkings.

Conclusion

The results of this study of LP1369 depletion have clearly demonstrated for the first time that LP1369 is cleared rapidly from treated quarters with mastitis. Optimisation of the intramammary formulation can take into consideration the need the maximum efficacy and minimum residence time of LP1369 in milk.

The invention claimed is:

1. A method of treating bacterial mastitis in a subject, the method consisting essentially of administering to a teat canal of the mammary gland of the subject a composition comprising a suspension of a solid dispersion of a therapeutically effective amount of a polyether ionophore selected from the group consisting of: narasin, salinomycin, lasalocid, monensin, semduramicin, maduramicin and laidlomycin, or a therapeutically acceptable salt thereof, as the sole antimicrobial agent, and a water-soluble polymer in an excipient or a gelling substance,
   wherein the bacterial mastitis is caused by a Gram-positive bacteria of the genus *Staphylococcus* or *Streptococcus*, or *Mycoplasma bovis*, and
   wherein the therapeutically effective amount is a dose in the range of 100 to 600 mg/teat canal.

2. The method according to claim 1, wherein the bacteria is selected from the group consisting of: *Staphylococcus epidermidis, Staphylococcus simulans, Staphylococcus fells, Staphylococcus xylosus, Staphylococcus chromogenes, Staphylococcus warneri, Staphylococcus haemolyticus, Staphylococcus sciuri, Staphylococcus saprophyticus, Staphylococcus hominis, Staphylococcus caprae, Staphylococcus cohnii* subsp. *cohnii, Staphylococcus cohnii* subsp. *urealyticus, Staphylococcus capitis* subsp. *capitis, Staphylococcus capitis* subsp. *urealyticus, Staphylococcus hyicus, Staphylococcus aureus, Staphylococcus pseudintermedius, Staphylococcus delphini, Staphylococcus schleiferi* subsp. *coagulans, Staphylococcus aureus* subsp. *anaerobius, Streptococcus uberis, Streptococcus agalactiae, Streptococcus dysgalactiae, Streptococcus pyogenes, Streptococcus bovis, Streptococcus equi* subsp. *Zooepidemicus, Streptococcus equinus*, and *Mycoplasma bovis*.

3. The method according to claim 2, wherein the bacteria is antibiotic resistant.

4. The method of claim 1, wherein the composition consists of the polyether ionophore, or the therapeutically acceptable salt thereof, the water-soluble polymer, and the excipient.

5. The method of claim 4, wherein the excipient is intended for rapid release.

6. The method of claim 1, wherein the composition consists of the polyether ionophore, or the therapeutically acceptable salt thereof, the water-soluble polymer, and the gelling substance.

7. The method of claim 1, wherein the gelling substance solidifies the composition or seals the teat canal.

8. A method of treating bacterial mastitis in a subject, the method comprising administering to a teat canal of the mammary gland of the subject a composition consisting of
   a suspension of a solid dispersion of a therapeutically effective amount of a polyether ionophore as the sole antimicrobial agent, wherein the polyether ionophore is selected from the group consisting of: narasin, salinomycin, lasalocid, monensin, semduramicin, maduramicin and laidlomycin, or a therapeutically acceptable salt thereof, and a water-soluble polymer in
   an excipient or gelling substance,
   wherein the bacterial mastitis is caused by a Gram-positive bacteria of the genus *Staphylococcus* or *Streptococcus*, or *Mycoplasma bovis*, and
   wherein the therapeutically effective amount is a dose in the range of 100 to 600 mg/teat canal.

9. The method of claim 8, wherein the therapeutically effective amount is a dose in the range of 150 to 600 mg/teat canal.

10. The method of claim 8, wherein the bacteria is selected from the group consisting of: *Staphylococcus epidermidis, Staphylococcus simulans, Staphylococcus fells, Staphylococcus xylosus, Staphylococcus chromogenes, Staphylococcus warneri, Staphylococcus haemolyticus, Staphylococcus sciuri, Staphylococcus saprophyticus, Staphylococcus hominis, Staphylococcus caprae, Staphylococcus cohnii* subsp. *cohnii, Staphylococcus cohnii* subsp. *urealyticus, Staphylococcus capitis* subsp. *capitis, Staphylococcus capitis* subsp. *urealyticus, Staphylococcus hyicus, Staphylococcus aureus, Staphylococcus pseudintermedius, Staphylococcus delphini, Staphylococcus schleiferi* subsp. *coagulans, Staphylococcus aureus* subsp. *anaerobius, Streptococcus uberis, Streptococcus agalactiae, Streptococcus dysgalactiae, Streptococcus pyogenes, Streptococcus bovis, Streptococcus equi* subsp. *Zooepidemicus, Streptococcus equinus*, and *Mycoplasma bovis*.

11. The method of claim 8, wherein the bacteria is antibiotic resistant.

12. The method of claim 8, wherein the excipient is intended for rapid release.

13. The method of claim 8, wherein the gelling substance solidifies the composition or seals the teat canal.

14. The method of claim 1, wherein the therapeutically effective amount is a dose in the range of 150 to 600 mg/teat canal.

15. The method of claim 1, wherein the water-soluble polymer is polyvinylpyrrolidone (PVP).

* * * * *

UNITED STATES PATENT AND TRADEMARK OFFICE
CERTIFICATE OF CORRECTION

PATENT NO. : 11,491,105 B2
APPLICATION NO. : 14/766233
DATED : November 8, 2022
INVENTOR(S) : Stephen Page et al.

It is certified that error appears in the above-identified patent and that said Letters Patent is hereby corrected as shown below:

In the Claims

At Column 51, Line 20, "fells," should be -- felis, --.

At Column 52, Line 21, "fells," should be -- felis, --.

Signed and Sealed this
Twentieth Day of June, 2023

Katherine Kelly Vidal
*Director of the United States Patent and Trademark Office*